US012592312B2

(12) United States Patent
Shelton, IV et al.

(10) Patent No.: US 12,592,312 B2
(45) Date of Patent: Mar. 31, 2026

(54) SURGICAL DATA SYSTEM AND CONTROL

(71) Applicant: Cilag GmbH International, Zug (CH)

(72) Inventors: Frederick E. Shelton, IV, Hillsboro, OH (US); Kevin Fiebig, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 939 days.

(21) Appl. No.: 17/384,337

(22) Filed: Jul. 23, 2021

(65) Prior Publication Data

US 2023/0027210 A1     Jan. 26, 2023

Related U.S. Application Data

(60) Provisional application No. 63/224,813, filed on Jul. 22, 2021.

(51) Int. Cl.
*G16H 40/20* (2018.01)
*A61B 17/00* (2006.01)
(Continued)

(52) U.S. Cl.
CPC ............. *G16H 40/20* (2018.01); *A61B 17/00* (2013.01); *A61B 18/1206* (2013.01);
(Continued)

(58) Field of Classification Search
CPC ........ G16H 40/20; G16H 10/60; G16H 15/00; G16H 20/40; G16H 30/40; G16H 40/40;
(Continued)

(56) References Cited

U.S. PATENT DOCUMENTS 6,766,373 B1    7/2004   Beadle et al.
8,565,073 B2    10/2013  Rahman et al.
(Continued)

FOREIGN PATENT DOCUMENTS

EP      3 506 287 A1    7/2019
JP      2017-504019 A5   12/2017
(Continued)

OTHER PUBLICATIONS

Hashimoto, et al., "Artificial Intelligence in Surgery: Promises and Perils", Annals of Surgery, vol. 268, No. 1, Jul. 2018, pp. 70-76.
(Continued)

*Primary Examiner* — Loren C Edwards
(74) *Attorney, Agent, or Firm* — Condo Roccia Koptiw LLP

(57)     ABSTRACT

A device to process data associated with a surgical event of a surgery may include a processor. The processor may be configured to receive multiple data streams during the surgical event. The processor may be configured to select a primary data stream based on a surgical data interface via which the primary data stream is received. The processor may be configured to select a secondary data stream based on a surgical data interface via which the second data stream is received. The processor may be configured to identify the surgical data interfaces. The processor may be configured to generate situational data associated with the primary data stream based on the secondary data stream. The situational data may indicate a medical decision-making factor of the surgical event. The primary data stream and the situational data may be sent during the surgical event.

18 Claims, 21 Drawing Sheets

(51) Int. Cl.

| | |
|---|---|
| *A61B 18/12* | (2006.01) |
| *A61B 34/00* | (2016.01) |
| *A61B 34/10* | (2016.01) |
| *A61B 34/20* | (2016.01) |
| *A61B 34/30* | (2016.01) |
| *A61B 34/32* | (2016.01) |
| *A61B 90/00* | (2016.01) |
| *G05B 13/02* | (2006.01) |
| *G06F 3/14* | (2006.01) |
| *G06F 3/16* | (2006.01) |
| *G06F 9/48* | (2006.01) |
| *G06F 9/54* | (2006.01) |
| *G06F 13/40* | (2006.01) |
| *G06F 16/21* | (2019.01) |
| *G06F 16/28* | (2019.01) |
| *G06N 20/00* | (2019.01) |
| *G06Q 10/30* | (2023.01) |
| *G06T 11/60* | (2006.01) |
| *G08B 5/22* | (2006.01) |
| *G10L 15/22* | (2006.01) |
| *G16H 10/60* | (2018.01) |
| *G16H 15/00* | (2018.01) |
| *G16H 20/40* | (2018.01) |
| *G16H 30/40* | (2018.01) |
| *G16H 40/40* | (2018.01) |
| *G16H 40/63* | (2018.01) |
| *G16H 40/67* | (2018.01) |
| *G16H 50/20* | (2018.01) |
| *G16H 50/70* | (2018.01) |
| *H04L 1/22* | (2006.01) |
| *H04L 41/12* | (2022.01) |
| *H04L 65/80* | (2022.01) |
| *H04L 67/12* | (2022.01) |
| *H04L 67/125* | (2022.01) |
| *H04N 5/272* | (2006.01) |
| *H04N 7/15* | (2006.01) |
| *A61B 8/06* | (2006.01) |
| *A61B 18/00* | (2006.01) |
| *G06F 21/62* | (2013.01) |
| *G06F 40/169* | (2020.01) |
| *G16H 30/20* | (2018.01) |
| *H02J 7/00* | (2006.01) |

(52) U.S. Cl.
CPC ............. *A61B 34/10* (2016.02); *A61B 34/20* (2016.02); *A61B 34/25* (2016.02); *A61B 34/30* (2016.02); *A61B 34/32* (2016.02); *A61B 90/08* (2016.02); *A61B 90/37* (2016.02); *G05B 13/0265* (2013.01); *G06F 3/14* (2013.01); *G06F 3/1423* (2013.01); *G06F 3/167* (2013.01); *G06F 9/4881* (2013.01); *G06F 9/542* (2013.01); *G06F 13/4068* (2013.01); *G06F 16/211* (2019.01); *G06F 16/284* (2019.01); *G06F 16/285* (2019.01); *G06N 20/00* (2019.01); *G06Q 10/30* (2013.01); *G06T 11/60* (2013.01); *G08B 5/22* (2013.01); *G10L 15/22* (2013.01); *G16H 10/60* (2018.01); *G16H 15/00* (2018.01); *G16H 20/40* (2018.01); *G16H 30/40* (2018.01); *G16H 40/40* (2018.01); *G16H 40/63* (2018.01); *G16H 40/67* (2018.01); *G16H 50/20* (2018.01); *G16H 50/70* (2018.01); *H04L 1/22* (2013.01); *H04L 41/12* (2013.01); *H04L 65/80* (2013.01); *H04L 67/12* (2013.01); *H04L 67/125* (2013.01); *H04N 5/272*

(2013.01); *H04N 7/15* (2013.01); *A61B 8/06* (2013.01); *A61B 2017/00221* (2013.01); *A61B 2018/00702* (2013.01); *A61B 2018/00994* (2013.01); *A61B 2034/2072* (2016.02); *A61B 2034/254* (2016.02); *A61B 2090/364* (2016.02); *A61B 2090/365* (2016.02); *A61B 2090/373* (2016.02); *G06F 21/6245* (2013.01); *G06F 40/169* (2020.01); *G10L 2015/223* (2013.01); *G16H 30/20* (2018.01); *H02J 7/0063* (2013.01)

(58) Field of Classification Search
CPC ........ G16H 40/63; G16H 40/67; G16H 50/20; G16H 50/70; G16H 30/20; A61B 8/06; A61B 17/00; A61B 18/1206; A61B 34/10; A61B 34/20; A61B 34/25; A61B 34/30; A61B 34/32; A61B 90/08; A61B 90/37; A61B 2017/00221; A61B 2018/007; A61B 2018/00994; A61B 2034/2072; A61B 2034/254; A61B 2090/364; A61B 2090/365; A61B 2090/373; G05B 13/0265; G06F 3/14; G06F 3/1423; G06F 3/167; G06F 9/4881; G06F 9/542; G06F 13/4068; G06F 16/211; G06F 16/284; G06F 16/285; G06F 21/6245; G06F 40/169; G06N 20/00; G06Q 10/30; G06T 11/60; G08B 5/22; G10L 15/22; G10L 2015/223; H04L 1/22; H04L 41/12; H04L 65/80; H04L 67/12; H04L 67/125; H04N 5/272; H04N 7/15; H02J 7/0063
See application file for complete search history.

(56) References Cited

U.S. PATENT DOCUMENTS

| | | | |
|---|---|---|---|
| 8,908,678 | B1 | 12/2014 | Mcgonigal et al. |
| 9,011,427 | B2 | 4/2015 | Price et al. |
| 9,283,054 | B2 | 3/2016 | Morgan et al. |
| 9,345,481 | B2 | 5/2016 | Hall et al. |
| 11,146,690 | B2 | 10/2021 | Minert |
| 11,232,868 | B1 | 1/2022 | Sutherland et al. |
| 11,564,573 | B2 | 1/2023 | Hirst |
| 2002/0000464 | A1 | 1/2002 | Ramberg et al. |
| 2005/0210070 | A1 | 9/2005 | Macneil |
| 2011/0276340 | A1 | 11/2011 | Deboer et al. |
| 2013/0051220 | A1 | 2/2013 | Ryshakov |
| 2013/0149967 | A1 | 6/2013 | Ma et al. |
| 2014/0160259 | A1 | 6/2014 | Blanquart et al. |
| 2014/0160260 | A1 | 6/2014 | Blanquart et al. |
| 2014/0163927 | A1 | 6/2014 | Molettiere et al. |
| 2014/0263552 | A1 | 9/2014 | Hall et al. |
| 2014/0267655 | A1 | 9/2014 | Richardson et al. |
| 2015/0119035 | A1 | 4/2015 | Ganu et al. |
| 2015/0128274 | A1 | 5/2015 | Giokas |
| 2015/0182118 | A1 | 7/2015 | Bradbury et al. |
| 2015/0215159 | A1 | 7/2015 | Liao et al. |
| 2017/0006135 | A1 | 1/2017 | Siebel et al. |
| 2017/0085627 | A1 | 3/2017 | Goldstein et al. |
| 2017/0296213 | A1 | 10/2017 | Swensgard et al. |
| 2018/0122506 | A1* | 5/2018 | Grantcharov ....... H04L 63/0421 |
| 2018/0344308 | A1 | 12/2018 | Nawana et al. |
| 2018/0360452 | A1 | 12/2018 | Shelton, IV et al. |
| 2019/0125455 | A1 | 5/2019 | Shelton, IV et al. |
| 2019/0191963 | A1 | 6/2019 | Kuhn et al. |
| 2019/0200844 | A1 | 7/2019 | Shelton, IV et al. |
| 2019/0200906 | A1 | 7/2019 | Shelton, IV et al. |
| 2019/0200980 | A1 | 7/2019 | Shelton, IV et al. |
| 2019/0200988 | A1 | 7/2019 | Shelton, IV |
| 2019/0201033 | A1 | 7/2019 | Yates et al. |
| 2019/0201102 | A1 | 7/2019 | Shelton, IV et al. |
| 2019/0201104 | A1 | 7/2019 | Shelton, IV et al. |

(56) References Cited

U.S. PATENT DOCUMENTS

| | | | |
|---|---|---|---|
| 2019/0201115 A1 | 7/2019 | Shelton, IV et al. | |
| 2019/0201123 A1 | 7/2019 | Shelton, IV et al. | |
| 2019/0201124 A1 | 7/2019 | Shelton, IV et al. | |
| 2019/0201125 A1 | 7/2019 | Shelton, IV et al. | |
| 2019/0201126 A1 | 7/2019 | Shelton, IV et al. | |
| 2019/0201127 A1 | 7/2019 | Shelton, IV et al. | |
| 2019/0201129 A1 | 7/2019 | Shelton, IV et al. | |
| 2019/0201137 A1 | 7/2019 | Shelton, IV et al. | |
| 2019/0201140 A1 | 7/2019 | Yates et al. | |
| 2019/0204201 A1 | 7/2019 | Shelton, IV et al. | |
| 2019/0205441 A1 | 7/2019 | Shelton, IV et al. | |
| 2019/0205566 A1 | 7/2019 | Shelton, IV et al. | |
| 2019/0205567 A1 | 7/2019 | Shelton, IV et al. | |
| 2019/0206216 A1 | 7/2019 | Shelton, IV et al. | |
| 2019/0206542 A1 | 7/2019 | Shelton, IV et al. | |
| 2019/0206551 A1 | 7/2019 | Yates et al. | |
| 2019/0206556 A1 | 7/2019 | Shelton, IV et al. | |
| 2019/0206562 A1 | 7/2019 | Shelton, IV et al. | |
| 2019/0206569 A1 | 7/2019 | Shelton, IV et al. | |
| 2019/0206576 A1 | 7/2019 | Shelton, IV et al. | |
| 2019/0207773 A1 | 7/2019 | Shelton, IV et al. | |
| 2019/0207857 A1 | 7/2019 | Shelton, IV et al. | |
| 2019/0207911 A1 | 7/2019 | Wiener et al. | |
| 2019/0333626 A1* | 10/2019 | Mansi | A61B 5/7267 |
| 2020/0244734 A1 | 7/2020 | Mendiola et al. | |
| 2020/0405403 A1 | 12/2020 | Shelton, IV et al. | |
| 2021/0145523 A1 | 5/2021 | Xing et al. | |
| 2021/0205030 A1 | 7/2021 | Shelton, IV et al. | |
| 2021/0205031 A1 | 7/2021 | Shelton, IV | |
| 2021/0212717 A1* | 7/2021 | Yates | A61B 17/3211 |
| 2021/0290046 A1 | 9/2021 | Nazareth et al. | |
| 2021/0313051 A1 | 10/2021 | Asselmann et al. | |
| 2021/0319894 A1 | 10/2021 | Sobol et al. | |
| 2021/0346094 A1 | 11/2021 | Fuerst et al. | |
| 2022/0020476 A1 | 1/2022 | Souissi | |
| 2022/0020486 A1 | 1/2022 | Giataganas et al. | |
| 2022/0046292 A1 | 2/2022 | Nair et al. | |
| 2022/0104713 A1 | 4/2022 | Shelton, IV | |
| 2022/0104807 A1 | 4/2022 | Shelton, IV et al. | |
| 2022/0104896 A1 | 4/2022 | Shelton, IV et al. | |
| 2022/0104910 A1 | 4/2022 | Shelton, IV et al. | |
| 2022/0108789 A1 | 4/2022 | Shelton, IV et al. | |
| 2022/0233119 A1 | 7/2022 | Shelton, IV et al. | |
| 2022/0233135 A1 | 7/2022 | Shelton, IV et al. | |
| 2022/0233136 A1 | 7/2022 | Shelton, IV et al. | |
| 2022/0233151 A1 | 7/2022 | Shelton, IV et al. | |
| 2022/0233191 A1 | 7/2022 | Shelton, IV et al. | |
| 2022/0233252 A1 | 7/2022 | Shelton, IV et al. | |
| 2022/0233254 A1 | 7/2022 | Shelton, IV et al. | |
| 2022/0238216 A1 | 7/2022 | Shelton, IV et al. | |
| 2022/0240869 A1 | 8/2022 | Shelton, IV et al. | |
| 2022/0241028 A1 | 8/2022 | Shelton, IV et al. | |
| 2022/0241474 A1 | 8/2022 | Shelton, IV et al. | |
| 2022/0303945 A1 | 9/2022 | Tsuda | |
| 2023/0021832 A1 | 1/2023 | Shelton, IV et al. | |
| 2023/0021920 A1 | 1/2023 | Shelton, IV et al. | |
| 2023/0022604 A1 | 1/2023 | Shelton, IV | |
| 2023/0023635 A1 | 1/2023 | Shelton, IV et al. | |
| 2023/0025790 A1 | 1/2023 | Shelton, IV et al. | |
| 2023/0025827 A1 | 1/2023 | Shelton, IV et al. | |
| 2023/0026893 A1 | 1/2023 | Shelton, IV et al. | |
| 2023/0027543 A1 | 1/2023 | Shelton, IV et al. | |
| 2023/0028059 A1 | 1/2023 | Shelton, IV et al. | |
| 2023/0028633 A1 | 1/2023 | Shelton, IV et al. | |
| 2023/0028677 A1 | 1/2023 | Shelton, IV et al. | |
| 2023/0035775 A1 | 2/2023 | Kohada | |
| 2023/0293236 A1 | 9/2023 | Wright et al. | |

FOREIGN PATENT DOCUMENTS

| | | | |
|---|---|---|---|
| WO | 2013/174327 A1 | 11/2013 | |
| WO | 2017/089479 A1 | 6/2017 | |
| WO | 2019/119130 A1 | 6/2019 | |
| WO | 2020/159978 A1 | 8/2020 | |
| WO | 2021/048326 A1 | 3/2021 | |
| WO | 2022195306 A1 | 9/2022 | |

OTHER PUBLICATIONS

Jagannath, et al., "An Analysis of Speech as a Modality for Activity Recognition during Complex Medical Teamwork", Pervasive Computing Technologies for Healthcare, May 2018, pp. 1-10.

Ban, Yutong et al., "Aggregating Long-Term Context for Learning Laparoscopic and Robot-Assisted Surgical Workflows", 2021 IEEE International Conference on Robotics and Automation (ICRA 2021), May 31-Jun. 4, 2021, 8 pages.

Kum, Sang-Uok , "Encoding of Multiple Depth Streams", 2008, 162 pages.

Amsterdam, et al., "Gesture Recognition in Robotic Surgery: A Review", IEEE Transactions on Biomedical Engineering, vol. 68, No. 6, Jun. 2021, pp. 2021-2035.

Cugola, et al., "Processing Flows of Information: From Data Stream to Complex Event Processing", ACM Computing Surveys, vol. 44, No. 03, Jun. 2012, 71 pages.

ISO 26262-1, "Road Vehicles—Functional Safety—Part 1: Vocabulary", International Organization for Standardization, Edition 2, Dec. 2018, 13 pages.

Khan, et al., "Zeqos: A New Energy and QoS-Aware Routing Protocol for Communication of Sensor Devices in Healthcare System", International Journal of Distributed Sensor Networks, vol. 10, No. 06, Jun. 5, 2014, 24 pages.

Namazi, et al., "Automatic Detection of Surgical Phases in Laparoscopic Videos", Proceedings on the international conference in artificial intelligence (ICAI), Aug. 2018, pp. 124-130.

International Search Report and Written Opinion, Received for PCT Application No. PCT/IB2022/056665, mailed on Oct. 31, 2022, 17 pages.

International Search Report and Written Opinion, Received for PCT Application No. PCT/IB2022/056666, mailed on Oct. 31, 2022, 11 pages.

International Search Report and Written Opinion, received for PCT Application No. PCT/IB2022/056669, mailed on Oct. 10, 2022, 16 pages.

Rahmani, et al., "Exploiting Smart E-Health Gateways at the Edge of Healthcare Internet-of-Things: A Fog Computing Approach", Future Generation Computer Systems, vol. 78, No. 02, Feb. 2017, 47 pages.

Ren, et al., "Multisensor Data Fusion in an Integrated Tracking System for Endoscopic Surgery", IEEE Transactions on Information Technology In Biomedicine, vol. 16. No. 1, Jan. 2012, pp. 106-111.

Doan, et al., "Introduction", Principles of Data Integration, Chapter 01, 2012, pp. 1-18.

Doan, et al., "Schema Matching and Mapping", Principles of Data Integration, Chapter 05, 2012, pp. 121-160.

Guibert, et al., "CC-Fog: Toward Content-Centric Fog Networks for E-Health", IEEE 19th International Conference on e-Health Networking, Applications and Services (Healthcom), Oct. 12-15, 2017, 5 pages.

"Blockchain", Wikipedia, (https://en.wikipedia.org/wiki/Blockchain), Jul. 2021, pp. 1-34.

* cited by examiner

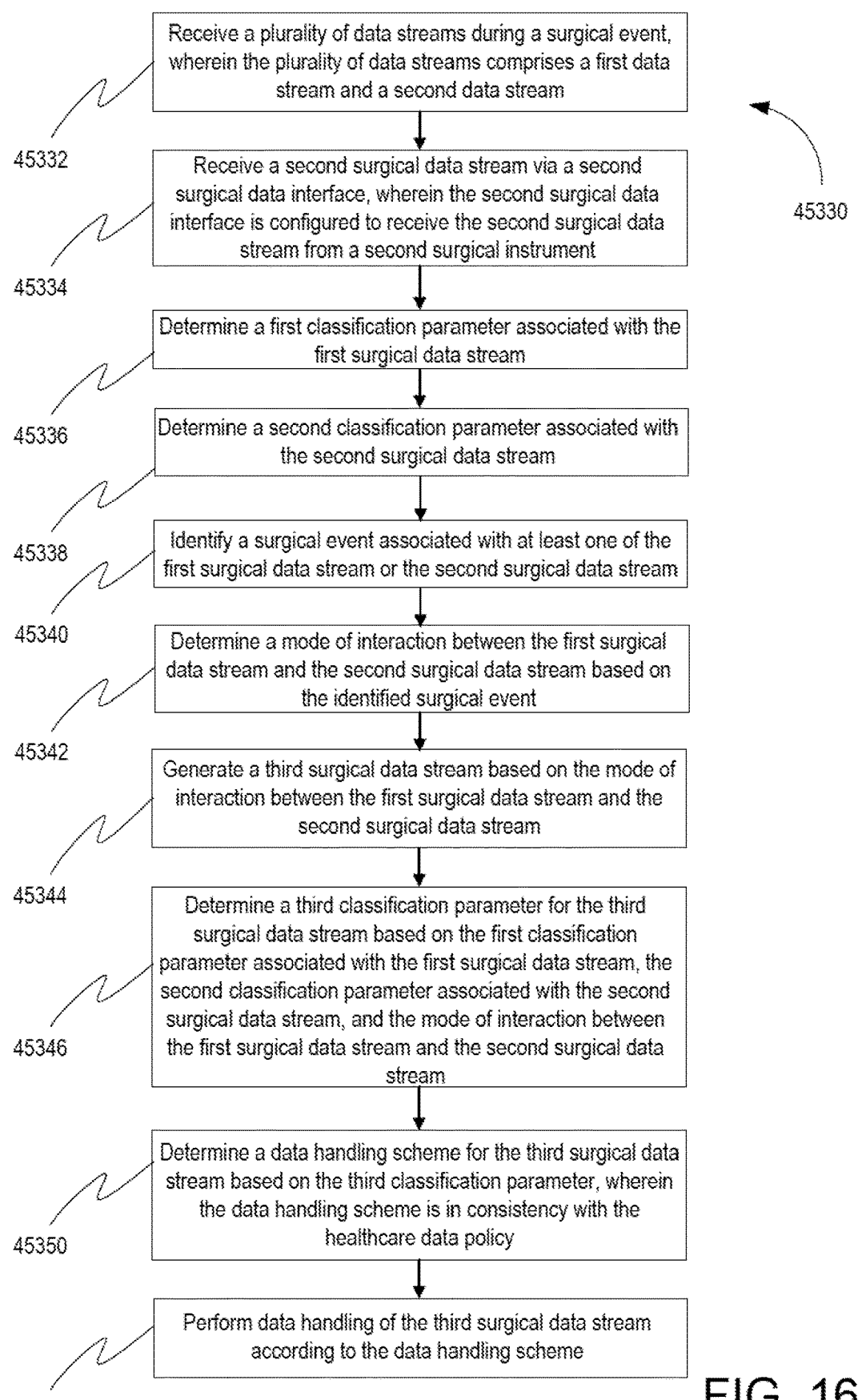

Receive a plurality of data streams during a surgical event, wherein the plurality of data streams comprises a first data stream and a second data stream

45332

Receive a second surgical data stream via a second surgical data interface, wherein the second surgical data interface is configured to receive the second surgical data stream from a second surgical instrument

45334

Determine a first classification parameter associated with the first surgical data stream

45336

Determine a second classification parameter associated with the second surgical data stream

45338

Identify a surgical event associated with at least one of the first surgical data stream or the second surgical data stream

45340

Determine a mode of interaction between the first surgical data stream and the second surgical data stream based on the identified surgical event

45342

Generate a third surgical data stream based on the mode of interaction between the first surgical data stream and the second surgical data stream

45344

Determine a third classification parameter for the third surgical data stream based on the first classification parameter associated with the first surgical data stream, the second classification parameter associated with the second surgical data stream, and the mode of interaction between the first surgical data stream and the second surgical data stream

45346

Determine a data handling scheme for the third surgical data stream based on the third classification parameter, wherein the data handling scheme is in consistency with the healthcare data policy

45350

Perform data handling of the third surgical data stream according to the data handling scheme

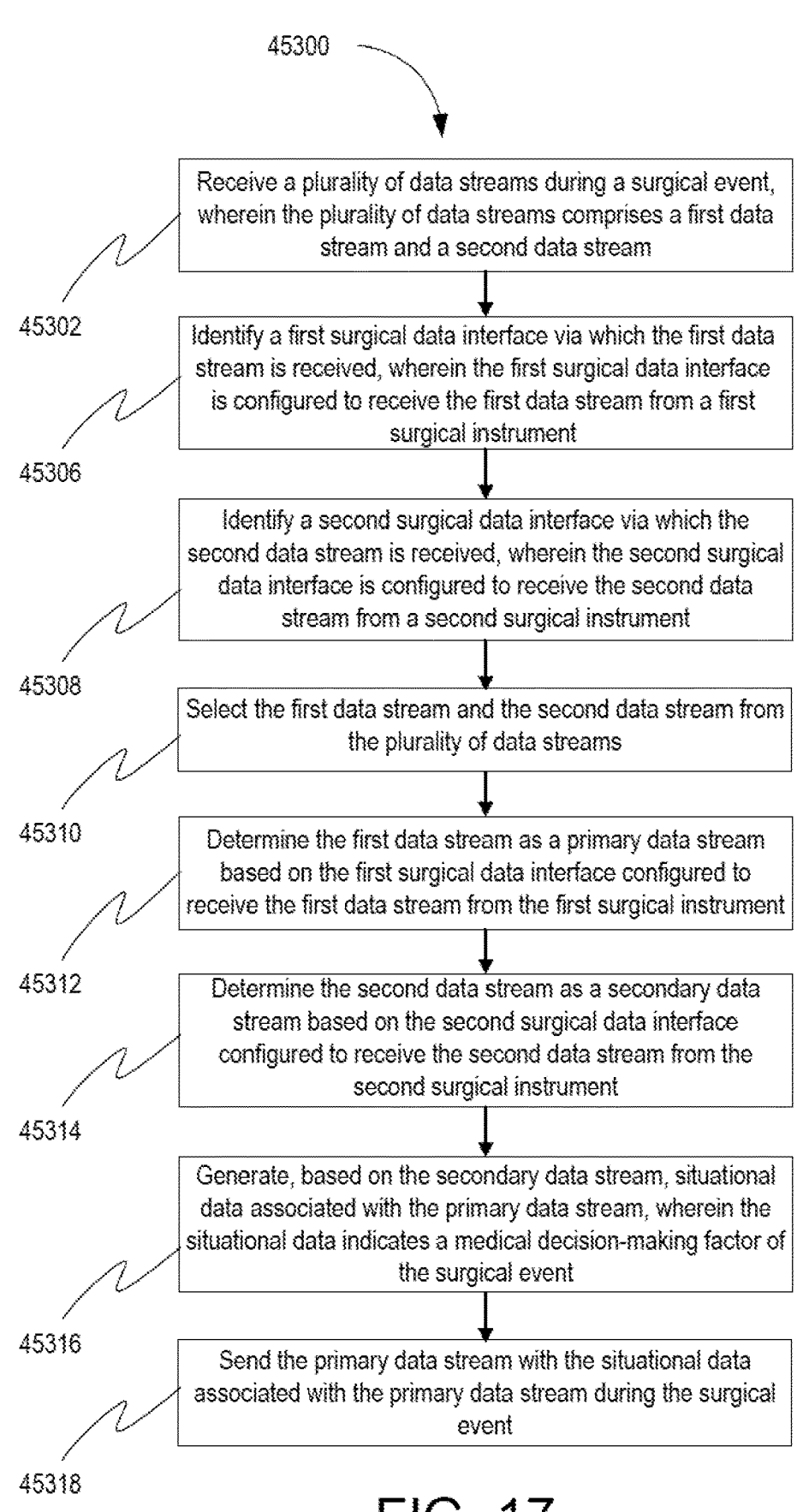

45300

Receive a plurality of data streams during a surgical event, wherein the plurality of data streams comprises a first data stream and a second data stream

45302

Identify a first surgical data interface via which the first data stream is received, wherein the first surgical data interface is configured to receive the first data stream from a first surgical instrument

45306

Identify a second surgical data interface via which the second data stream is received, wherein the second surgical data interface is configured to receive the second data stream from a second surgical instrument

45308

Select the first data stream and the second data stream from the plurality of data streams

45310

Determine the first data stream as a primary data stream based on the first surgical data interface configured to receive the first data stream from the first surgical instrument

45312

Determine the second data stream as a secondary data stream based on the second surgical data interface configured to receive the second data stream from the second surgical instrument

45314

Generate, based on the secondary data stream, situational data associated with the primary data stream, wherein the situational data indicates a medical decision-making factor of the surgical event

45316

Send the primary data stream with the situational data associated with the primary data stream during the surgical event

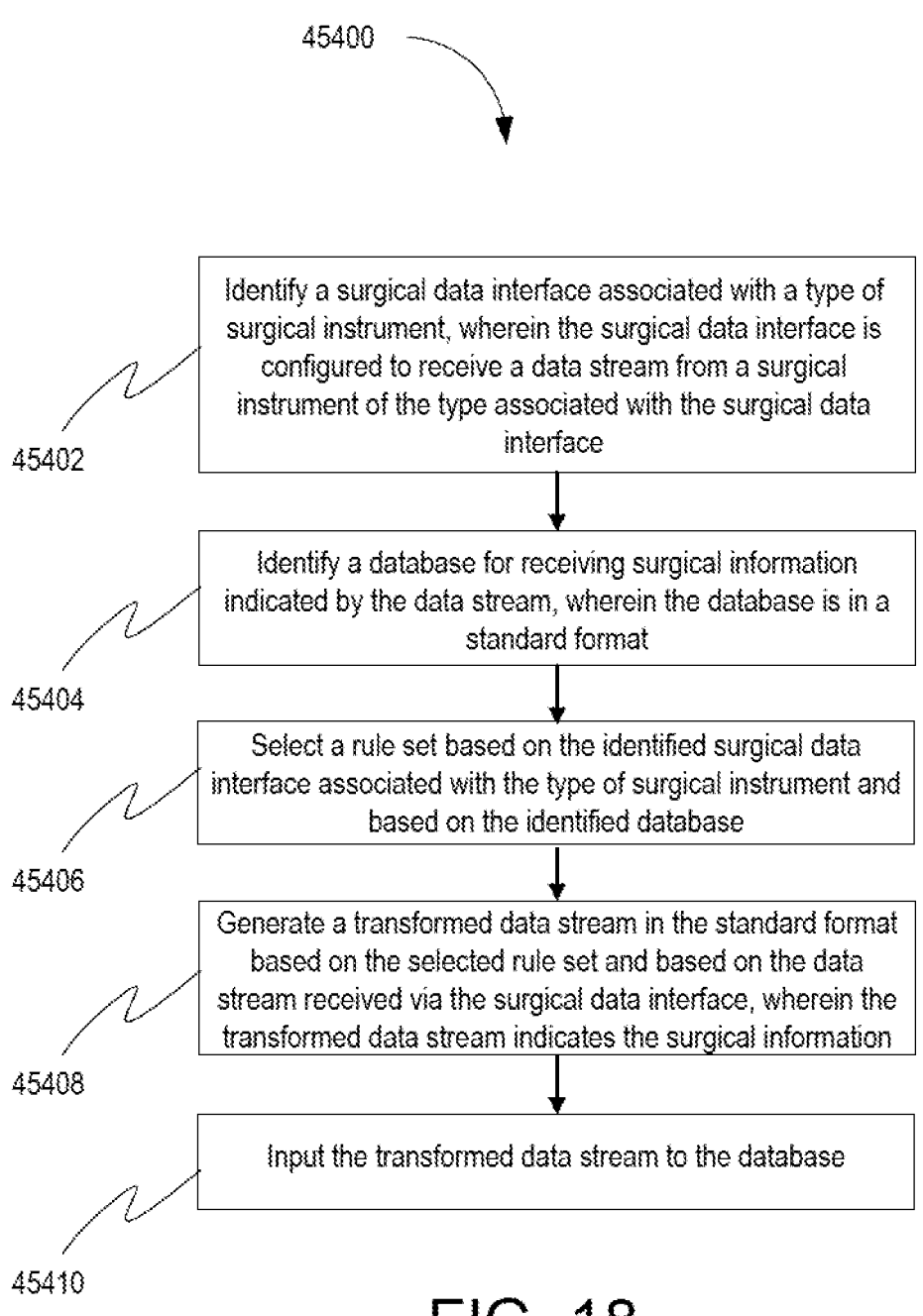

45400

45402

Identify a surgical data interface associated with a type of surgical instrument, wherein the surgical data interface is configured to receive a data stream from a surgical instrument of the type associated with the surgical data interface

45404

Identify a database for receiving surgical information indicated by the data stream, wherein the database is in a standard format

45406

Select a rule set based on the identified surgical data interface associated with the type of surgical instrument and based on the identified database

45408

Generate a transformed data stream in the standard format based on the selected rule set and based on the data stream received via the surgical data interface, wherein the transformed data stream indicates the surgical information

45410

Input the transformed data stream to the database

FIG. 18

SURGICAL DATA SYSTEM AND CONTROL

CROSS-REFERENCE TO RELATED APPLICATIONS

This application claims the benefit of Provisional U.S. Patent Application Ser. No. 63/224,813, filed Jul. 22, 2021, the disclosure of which is incorporated herein by reference in its entirety.

This application is related to the following, filed contemporaneously, the contents of each of which are incorporated by reference herein:

U.S. patent application Ser. No. 17/384,274, filed Jul. 23, 2021, titled METHOD OF SURGICAL SYSTEM POWER MANAGEMENT, COMMUNICATION, PROCESSING, STORAGE, AND DISPLAY U.S. patent application Ser. No. 17/384,348, filed Jul. 23, 2021, titled SURGICAL DATA SYSTEM AND CLASSIFICATION U.S. patent application Ser. No. 17/384,354, filed Jul. 23, 2021, tided SURGICAL DATA SYSTEM AND MANAGEMENT

BACKGROUND

Surgical procedures may be performed in surgical operating theaters or rooms in a healthcare facility such as, for example, a hospital. Various surgical devices and systems may be utilized in performance of a surgical procedure. In the digital and information age, medical systems and facilities may implement systems or procedures utilizing digital technologies while maintaining patient safety.

SUMMARY

Examples described herein may include a device to process and/or classify data associated with a surgical event of a surgery. The device may include a processor.

The processor may be configured to process the data associated with the surgical event based on another data. The processor may be configured to receive multiple data streams during the surgical event. The processor may be configured to select a first data stream and a second data stream from the multiple data streams. The first data stream may be selected as the primary data stream, and the second data stream may be selected as the secondary data stream. The selection of the primary data stream may be based on a surgical data interface via which the primary data stream is received. The selection of the secondary data stream may be based on a surgical data interface via which the secondary data stream is received. The processor may be configured to identify the surgical data interface that is configured to receive the primary data stream and identify the surgical data interface that is configured to receive the secondary data stream. The processor may be configured to generate situational data associated with the primary data stream based on the secondary data stream. The situational data may indicate a medical decision-making factor of the surgical event. The primary data stream and the situational data may be sent during the surgical event. The secondary data stream may include a first portion and a second portion. The processor may be configured to store the first portion of the secondary data stream and not the second portion of the secondary data stream.

The primary data stream may include a first timing element. The first timing element may indicate a first time when the first data stream is collected during the surgical event. The primary data stream and the situational data associated with the primary data stream may be sent at a second time during the surgical event, and a difference between the first time and the second time may be lower than a predetermined value. The predetermined value may be used for real-time processing. The difference that is lower than the predetermined value may indicate that the primary data stream is sent in real time, for example, as the first data stream is collected.

The primary data stream may be sent via data packets. At least one of the data packets may include a field indicative of the situational data. The situational data may be sent using at least one of an annotation for the primary data stream, a context associated with the primary data stream, or meta data that indicates the context associated with the primary data stream.

The processor may be configured to generate control instructions based on the primary data stream and the situational data associated with the primary data stream, and the processor may be configured to send the control instructions to a surgical instrument in communication with the device, for example, to change an operation of the surgical instrument.

The processor may be configured to generate a risk indicator based on the primary data stream and the situational data associated with the primary data stream. The risk indicator may include at least one of an action trigger, a notification, or a threshold. The processor may be configured to send the risk indicator, for example, to a displaying device.

The surgical event may be an ongoing surgical event. The processor may be configured to determine that the ongoing surgical event and a historical surgical event have a characteristic in common. The processor may be configured to generate the situational data further based on a data stream associated with the historical surgical event. The characteristic in common may include at least one of a same patient, a same type of surgical procedure, a same type of surgical instrument, or a same type of surgical equipment.

The processor may be configured to classify the data associated with the surgical event. The processor may be configured to receive a first surgical data stream via a first surgical data interface and receive a second surgical data stream via a second surgical data interface. The first surgical data interface may be configured to receive the first surgical data stream from a first surgical instrument. The second surgical data interface may be configured to receive the second surgical data stream from a second surgical instrument. The processor may be configured to determine a first classification parameter associated with the first surgical data stream. The processor may be configured to determine a second classification parameter associated with the second surgical data stream. The processor may be configured to identify the first surgical data interface and determine the first classification parameter based on the identified first surgical data interface. The first surgical data interface may be designated to communicate with a first type of surgical instrument. The processor may be configured to identify the second surgical data interface and determine the second classification parameter based on the identified second surgical data interface. The second surgical data interface may be designated to communicate with a second type of surgical instrument. The processor may be configured to determine the first classification parameter based on decoding the first classification parameter in the first surgical data stream. The processor may be configured to determine the second classification parameter based on decoding the second classification parameter in the second surgical data stream. In some examples, the processor may decode the first surgical data stream and infer the first classification parameter based on the decoded first surgical data stream. The processor may decode the second surgical data stream and infer the second classification parameter based on the decoded second surgical data stream. The processor may be configured to determine a mode of interaction between the first surgical data stream and the second surgical data stream. The processor may be configured to identify a surgical event associated with at least one of the first surgical data stream or the second surgical data stream and determine the mode of interaction based on the surgical event. The mode of interaction may generate situational data of the identified surgical event. The mode of interaction may include one or more of an enrichment of the first surgical data stream using the second surgical data stream, an aggregation of the first surgical data stream and the second surgical data stream, or a synthesis of the first surgical data stream and the second surgical data stream.

The processor may be configured to generate a third surgical data stream based on the mode of interaction between the first surgical data stream and the second surgical data stream. The processor may be configured to determine a third classification parameter for the third surgical data stream based on the first classification parameter associated with the first surgical data stream, the second classification parameter associated with the second surgical data stream, and the mode of interaction between the first surgical data stream and the second surgical data stream. At least one of the first classification parameter, the second classification parameter, or the third classification parameter may be multidimensional. The third classification parameter (e.g., a value of the third classification parameter) may indicate one or more of privacy of the third surgical data stream, a priority of the third surgical data stream, a content type of the third surgical data stream, a context of the third surgical data stream, a retention period associated with the third surgical data stream, or a user preference associated with the third surgical data stream.

The processor may be configured to determine a data handling scheme for the third surgical data stream based on the third classification parameter. The data handling scheme may be consistent with a healthcare data policy. The processor may be configured to perform data handling of the third surgical data stream according to the data handling scheme. The data handling scheme may include one or more of a type of storage location for the third surgical data stream or a reliability level associated with a communication path used for the third surgical data stream.

In an example, the processor may be configured to determine, based on the third classification parameter, that the third surgical data stream has the highest classification level among multiple surgical data streams that are to be transmitted. The processor may be configured to determine the communication path that has the least amount of interruption among transmission resources that are available to be used for the transmissions of the surgical data streams. The processor may be configured to send the third surgical data stream using the determined communication path. The processor may be configured to repeat the sending of the third surgical data stream based on the determination that the third surgical data stream has the highest classification level among the surgical data streams to be transmitted.

The processor may be configured to determine a data handling scheme for the second surgical data stream. The second classification parameter and the third classification parameter may be the same. The processor may be configured to determine, based on the second classification parameter, the same data handling scheme for the second surgical data stream as the data handling scheme for the third surgical data stream.

The processor may be configured to process data associated with the surgical event into a standard format. The processor may be configured to identify a surgical data interface associated with a type of surgical instrument. The surgical data interface may be configured to receive a data stream from a surgical instrument of the type associated with the surgical data interface. The processor may be configured to identify a database for receiving surgical information indicated by the data stream. The database may be in a standard format. For example, the database may be a relational database. The standard format may indicate at least one of a resolution, a sampling rate, a measurement type, a unit of measurement, or a type of data stream. The type of data stream may be a discrete data stream or a continuous data stream. The processor may be configured to select a rule set based on the identified surgical data interface associated with the type of surgical instrument and based on the identified database. The rule set may include one or more of a data cleaning rule, a data verification rule, or a data formatting rule. The processor may be configured to generate a transformed data stream in the standard format based on the selected rule set and based on the data stream received via the surgical data interface. The transformed data stream may indicate the surgical information. The processor may be configured to input the transformed data stream to the database. The processor may be configured to determine, for the first data stream, invalid data and invalid associations based on the selected rule set. The first transformed data stream may exclude the invalid data and the invalid associations. The processor may be configured to generate a second transformed data stream in the standard format based on a second data stream and generate an annotation for the first data stream based on the second data stream such that the first transformed data stream comprises the annotation.

The data stream may include visualization data, biomarker data, surgical instrument data, or surgical equipment data. In an example, the processor may be configured to receive a first data stream and generate a first transformed data stream in the standard format based on a first rule set. The processor may be configured to generate a second transformed data stream in the standard format based on a second data stream. The second data stream may include a patient data stream, a surgical instrument data stream associated with a surgical operation, or a surgical equipment data stream. The second transformed data stream and the first transformed data stream may be at a same sampling rate or a same synchronization, or linked to a same surgical event.

BRIEF DESCRIPTION OF THE DRAWINGS

FIG. 16 shows a data classification example.

FIG. 17 shows a data processing example.

FIG. 18 shows a data standardization example.

DETAILED DESCRIPTION

Figure 1A:
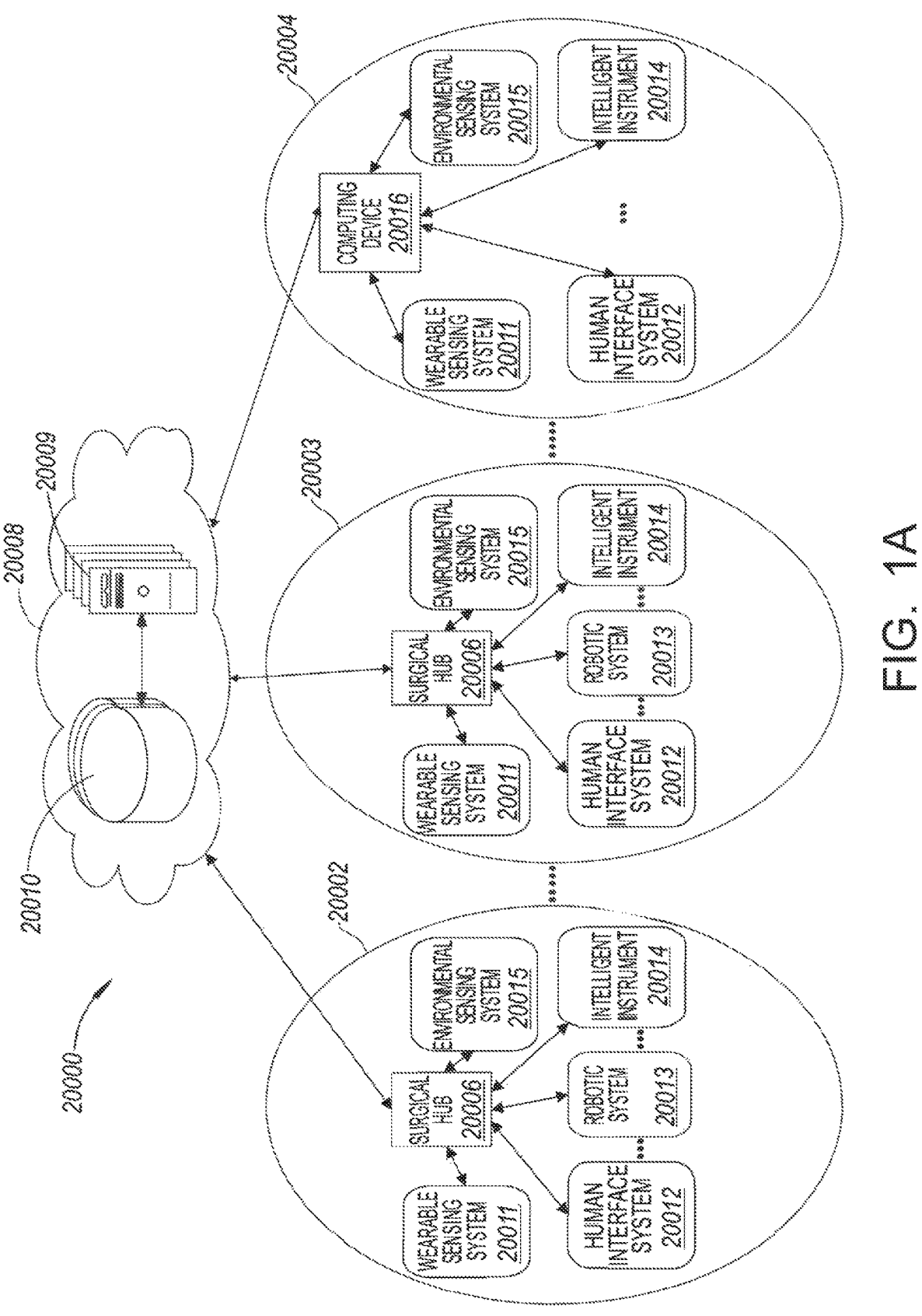
FIG. 1A is a block diagram of a computer-implemented surgical system.

FIG. 1A is a block diagram of a computer-implemented surgical system 20000. An example surgical system such as the surgical system 20000 may include one or more surgical systems (e.g., surgical sub-systems) 20002, 20003 and 20004. For example, surgical system 20002 may include a computer-implemented interactive surgical system. For example, surgical system 20002 may include a surgical hub 20006 and/or a computing device 20016 in communication with a cloud computing system 20008, for example, as described in FIG. 2. The cloud computing system 20008 may include at least one remote cloud server 20009 and at least one remote cloud storage unit 20010. Example surgical systems 20002, 20003, or 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more HCP sensing systems, and/or one or more patient sensing systems. The environmental sensing system 20015 may include one or more devices, for example, used for measuring one or more environmental attributes, for example, as further described in FIG. 2. The robotic system 20013 may include a plurality of devices used for performing a surgical procedure, for example, as further described in FIG. 2.

The surgical system 20002 may be in communication with a remote server 20009 that may be part of a cloud computing system 20008. In an example, the surgical system 20002 may be in communication with a remote server 2000) via an internet service provider's cable/FIOS networking node. In an example, a patient sensing system may be in direct communication with a remote server 20009. The surgical system 20002 and/or a component therein may communicate with the remote servers 20009 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 20011. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

For example, the sensing systems 20001 may include the wearable sensing system 20011 (which may include one or more HCP sensing systems and one or more patient sensing systems) and the environmental sensing system 20015 as discussed in FIG. 1A. The one or more sensing systems 20001 may measure data relating to various biomarkers. The one or more sensing systems 20001 may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers as described herein using one of more of the following sensing technologies: photoplethysmography, electrocardiography, electroencephalography, colorimetry, impedimentary, potentiometry, amperometry, etc.

The biomarkers measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and the surgical system 20000, for example. The information from the biomarkers may be determined and/or used by the computer-implemented patient and the surgical system 20000 to improve said systems and/or to improve patient outcomes, for example. The one or more sensing systems 20001, biomarkers 20005, and physiological systems are described in more detail in U.S. application Ser. No. 17/156,287, titled METHOD OF ADJUSTING A SURGICAL PARAMETER BASED ON BIOMARKER MEASUREMENTS, filed Jan. 22, 2021, the disclosure of which is herein incorporated by reference in its entirety.

Figure 1B:
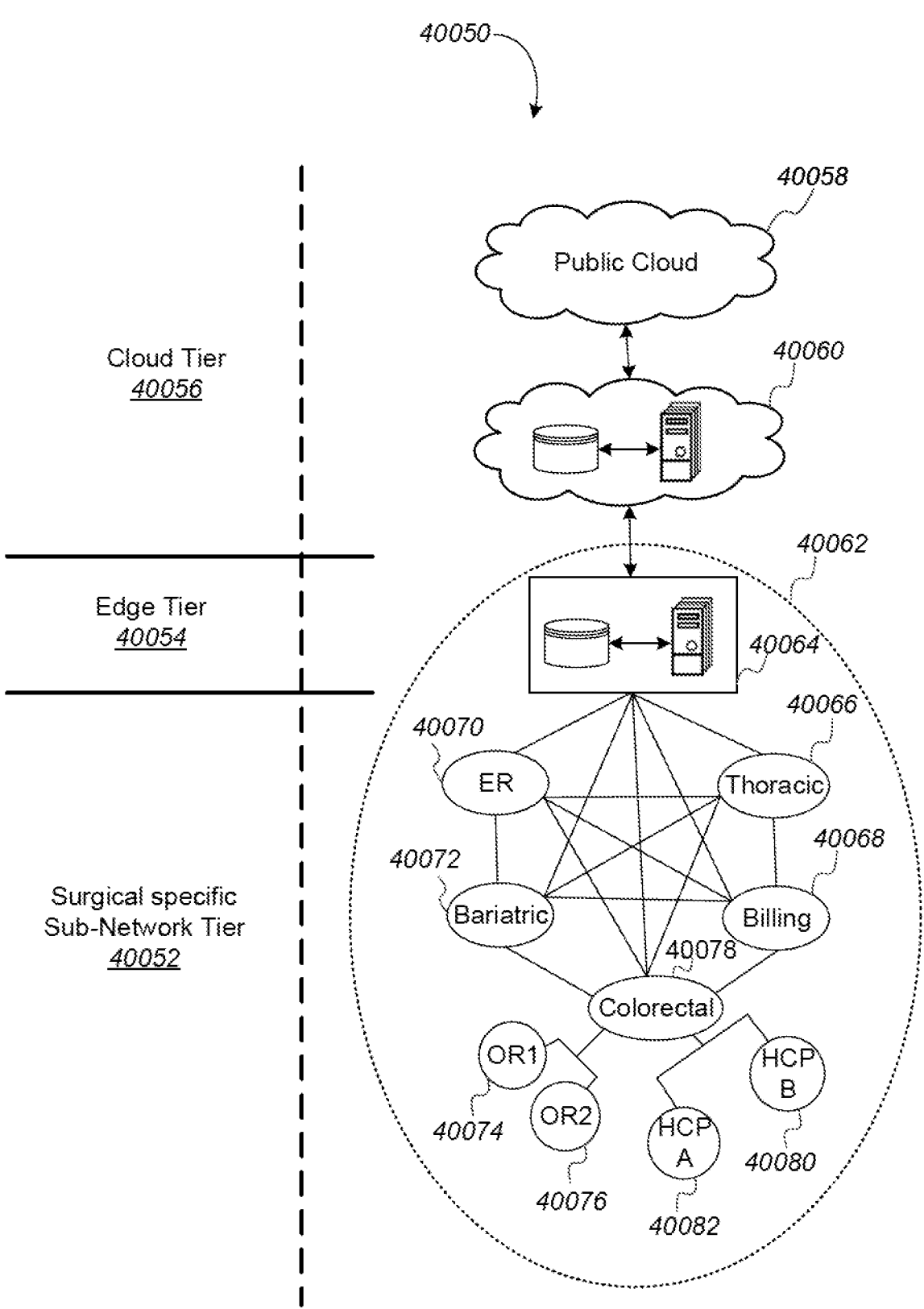
FIG. 1B is a block diagram of a computer-implemented multi-tier surgical system.

FIG. 1B is a block diagram of a computer-implemented multi-tier surgical system. As illustrated in FIG. 1B, a computer-implemented multi-tier surgical system 40050 may include multiple tiers of systems, such as a surgical specific sub-network tier system 40052, an edge tier system 40054 that is associated with the surgical specific sub-network tier system 40052, and a cloud tier system 40056.

A surgical specific sub-network tier system 40052 may include a plurality of inter-connected surgical sub-systems. For example, the surgical sub-systems may be grouped by the type of surgical procedures and/or other departments in a medical facility or a hospital. For example, a medical facility or a hospital may include a plurality of surgical procedure specific departments, such as an emergency room (ER) department 40070, colorectal department 40078, bariatric department 40072, thoracic department 40066, and billing department 40068. Each of the surgical procedure specific departments may include one or more surgical sub-systems associated with an operating room (OR) and/or a healthcare care professional (HCP). For example, the colorectal department 40078 may include a set of surgical hubs (e.g., surgical hub 20006 as described in FIG. 1A). The surgical hubs may be designated for a respective HCP, such as HCP A, 40082 and HCP B, 40080. In an example, the colorectal department may include a group of surgical hubs that may be located in respective ORs, such as OR 1, 40074 and OR 2, 40076. The medical facility or the hospital may also include a billing department subsystem 40068. The billing department subsystem 40068 may store and/or manage billing data associated with a respective department, such as the ER department 40070, colorectal department 40078, bariatric department 40072, and/or thoracic department 40006.

An edge tier system 40054 may be associated with a medical facility or a hospital and may include one or more edge computing systems 40064, for example. An edge computing system 40064 may include a storage sub-system and a server sub-system. In an example, the edge computing system comprising an edge server and/or a storage unit may provide additional processing and/or storage services to a surgical hub that is part of one of the departmental ORs (e.g., OR1 and OR2 of the colorectal department).

The surgical specific sub-network tier system 40052 and the edge tier system 40054 may be located within a Health Insurance Portability and Accountability Act (HIPAA) boundary 40062. The surgical specific sub-network system 40052 and the edge tier system 40054 may be connected to the same local data network. The local data network may be a local data network of a medical facility or a hospital. The local data network may be within the HIPAA boundary. Because the surgical specific sub-network tier system 40052 and the edge tier system 40054 are located within the HIPAA boundary 40062, patient data between an edge computing system 40064 and a device located within one of the entities of the surgical specific sub-network tier system 40052 may flow without redaction and/or encryption. For example, patient data between an edge computing system 40064 and a surgical hub located in OR1 40074 of the colorectal department 40078 may flow without redaction and/or encryption.

The cloud tier system 40056 may include an enterprise cloud system 40060 and a public cloud system 40058. For example, the enterprise cloud system 40060 may be a cloud computing system 20008 that includes a remote cloud server sub-system and/or a remote cloud storage subsystem, as described in FIG. 1A. The enterprise cloud system 40060 may be managed by an organization, such as a private company. The enterprise cloud system 40060 may be in communication with one or more entities (e.g., edge computing systems 40064, surgical hubs located in ORs (e.g., OR1 40074) of the various departments (e.g., colorectal department 40078)) that are located within the HIPAA boundary 40062.

The public cloud system 40058 may be operated by a cloud computing service provider. For example, the cloud computing service provider may provide storage services and/or computing services to a plurality of enterprise cloud systems (e.g., enterprise cloud system 40060).

Figure 1C:
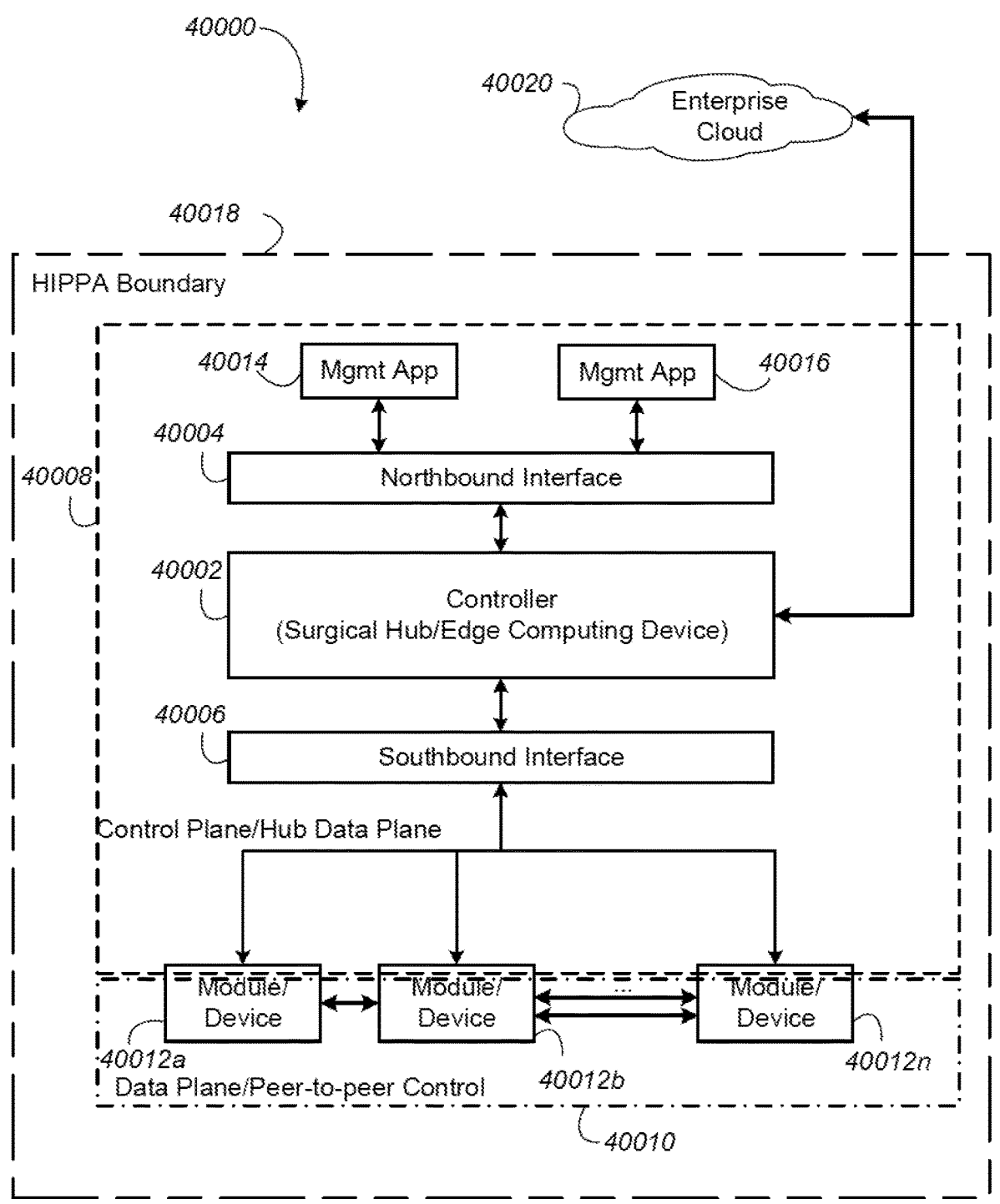
FIG. 1C is a logical diagram illustrating control plane and data plane of a surgical system.

FIG. 1C is a logical block diagram 40000 illustrating various communication planes in a surgical system. As illustrated in FIG. 1C, the communication planes between a controller 40002 and management applications 40014 and 40016 on one side and, the system modules and/or modular devices 40012*a* through 40012*n*1 on the other side, may use control plane 40008 and data plane 40010. In an example, in addition to the control plane 40008, a data plane may also exist between the system modules and/or modular devices 40012*a* through 40012*n* and the surgical hub. The data plane 40010 may provide data plane paths (e.g., redundant data plane paths) between the system modules and/or the modular devices 40012*a* through 40012*n* that are associated with one or more surgical hubs. A surgical hub or one of the surgical hubs (e.g., in case of a plurality of surgical hubs present in an operating room) may act as a controller 40002. In an example, the controller 40002 may be an edge computing system that may reside within a Health Insurance Portability and Accountability Act (HIPAA) boundary where the surgical system is located, for example, as illustrated in FIG. 1B. The controller 40002 may be in communication with an enterprise cloud system 40020. As illustrated in FIG. 1C, the enterprise cloud system 40020 may be located outside the HIPAA boundary 40018. Accordingly, the patient data flowing to and/or from the enterprise cloud system 40020 may be redacted and/or encrypted.

The controller 40002 may be configured to provide a northbound interface 40004 and a southbound interface 40006. The northbound interface 40004 may be used for providing a control plane 40008. The control plane 40008 may include one or more management applications 40014 and 40016 that may enable a user to configure and/or manage system modules and/or modular devices modular devices 40012*a* through 40012*n* associated with a surgical system. The management applications 40014 and 40016 may be used to obtain status of various system modules and/or the modular devices 40012*a* through 40012*n*.

The management applications 40014 and 40016 using the control plane may interact with the controller 40002, for example, using a set of application programming interface (APT) calls. The management applications 40014 and 40016 may interact with the controller 40002 via a management protocol or an application layer protocol to configure and/or monitor the status of a system module and/or a modular device. The management protocols or the application layer protocols used to monitor the status and/or configure a system module or a modular device associated with a surgical system may include the simple network management protocol (SNMP), TELNET protocol, secure shell (SSH) protocol, network configuration protocol (NETCONF), etc.

SNMP or a similar protocol may be used to collect status information and/or send configuration related data (e.g., configuration related control programs) associated with system modules and/or modular devices to the controller. SNMP or a similar protocol may collect information by selecting devices associated with a surgical system from a central network management console using messages (e.g., SNMP messages). The messages may be sent and/or received at fixed or random intervals. The messages may include Get messages and Set messages. The Get messages or messages similar to the Get messages may be used for obtaining information from a system module or a modular device associated with a surgical system. The Set message or messages similar to the Set message may be used for changing a configuration associated with a system module or a modular device associated with a surgical system.

For example, the Get messages or similar messages may include the SNMP messages GetRequest, GetNextRequest, or GetBulkRequest. The Set messages may include SNMP SetRequest message. The GetRequest, GetNextRequest, GetBulkRequest messages or similar messages may be used by a configuration manager (e.g., an SNMP manager) running on the controller 40002. The configuration manager may be in communication with a communication agent (e.g., an SNMP agent) that may be a part of a system module and/or a modular device in a surgical system. The SNMP message SetRequest message or similar may be used by the communication manager on the controller 40002 to set the value of a parameter or an object instance in the communication agent on a system module and/or a modular device of a surgical system. In an example, SNMP modules, for example, may be used to establish communication path between system modules and/or modular devices associated with a surgical system.

Based on the query or configuration related messages received from a management application, such as management applications 40014 and 40016, the controller 40002 may generate configuration queries and/or configuration data for querying or configuring the system modules and/or the modular devices associated with the surgical hub or the surgical system. A surgical hub (e.g., the surgical hub 20006 shown in FIG. 1A) or an edge computing system (e.g., the edge computing system 40064 shown in FIG. 1B) may manage and/or control various system modules and/or modular devices 40012a through 40012n associated with a surgical system. For example, the northbound interface 40004 of the controller 40002 may be used for changing control interactions between one or more modules associated and/or devices associated with a surgical system. In an example, the controller 40002 may be used for establishing one or more communication data paths between a plurality of modules and/or devices associated with a surgical system. The controller 40002 may use its southbound interface 40006 to send the control programs comprising queries and/or configuration changes to the system modules and/or the modular devices of the surgical system.

The system modules and/or the modular devices 40012a through 40012n of a surgical system, or the communication agents that may be a part of the system modules and/or the modular devices, may send notification messages or traps to the controller 40002. The controller may forward the notification messages or traps via its northbound interface 40004 to the management application 40014 and 40016 for displaying on a display. In an example, the controller 40002 may send the notification to other system modules and/or modular devices 40012a through 40012n that are part of the surgical system.

The system modules and/or the modular devices 40012a through 40012n of a surgical system or the communication agents that are part of the system modules and/or the modular devices may send responses to the queries received from the controller 40002. For example, a communication agent that may be part of a system module or a modular device may send a response message in response to a Get or a Set message or messages similar to the Get or the Set messages received from the controller 40002. In an example, in response to a Get message or a similar message received from the controller 4002, the response message from the system module or the modular device 40012a through 40012n may include the data requested. In an example, in response to a Set message or a similar message received from a system module or a modular device 40012a through 40012n, the response message from the controller 40002 may include the newly set value as confirmation that the value has been set.

A trap or a notification message or a message similar to the trap or the notification message may be used by a system module or a modular device 40012a through 40012n to provide information about events associated with the system modules or the modular devices. For example, a trap or a notification message may be sent from a system module or a modular device 40012a through 40012n to the controller 410002 indicating a status of a communication interface (e.g., whether it available or unavailable for communication). The controller 40002 may send a receipt of the trap message back to the system module or the modular device 40012a through 40012n (e.g., to the agent on the system module or a modular device).

In an example, TELNET protocol may be used to provide a bidirectional interactive text-oriented communication facility between system modules and/or modular devices 40012a through 40012n and the controller 40002. TELNET protocol may be used to collect status information and/or send configuration data (e.g., control programs) from/to the controller 40002. TELNET may be used by one of the management applications 40014 or 40016 to establish a connection with the controller 40002 using the transmission control protocol port number 23.

In an example, SSH, a cryptographic encrypted protocol, may be used to allow remote login and to collect status information and/or send configuration data about system modules and/or modular devices 40012a through 40012n from/to the controller 40002. SSH may be used by one of the management applications 40014 or 40016 to establish an encrypted connection with the controller 40002 using the transmission control protocol port number 22.

In an example, NETCONF may be used to perform management functions by invoking remote procedure calls using, for example, <rpc>, <rpc-reply>, or <edit-config> operations. The <rpc> and <rpc-reply> procedure calls or similar procedure calls may be used for exchanging information from a system module and/or a modular device associated with a surgical system. The NETCONF <edit-config> operation or a similar operation may be used for configuring the system modules and/or the modular devices associated with the surgical system.

The controller 40002 may configure the system modules and/or modular device 40012a through 40012n to establish a data plane 40010. The data plane 40010 (e.g., also referred to as a user plane or a forwarding plane) may enable a communication data path between a plurality of system modules and/or modular device 40012a through 40012n. The data plane 40010 may be utilized by the system modules and/or the modular device 40012a through 40012n for communicating data flows of data between the system modules and/or modular devices associated with a surgical system. The data flows may be established using one or more dedicated communication interfaces between the system modules and/or the modular devices associated with one or more surgical hubs of a surgical system. In an example, the data flows may be established over one or more local area networks (LANs) and one or more wide area networks (WANs), such as the Internet.

In an example, the data plane 40010 may provide support for establishing a first and a second independent, disjointed, concurrent, and redundant communication path for data flow between the system modules and/or modular devices 40012*b* and 40012*n*. As illustrated in FIG. 1C, redundant communication paths may be established between system modules/modular devices 40012*b* and 40012*n*. The redundant communication paths may carry same/redundant data flows between the system modules and/or modular devices. In an example, when or if some of the data packets are dropped on one of the redundant communication paths due to problems with one of the communication interfaces on the system modules/modular devices 40012*b* and 40012*n*, the system modules and/or the modular devices may continue to send/receive at least one copy of the dropped data packets over the second communication path.

Figure 2:
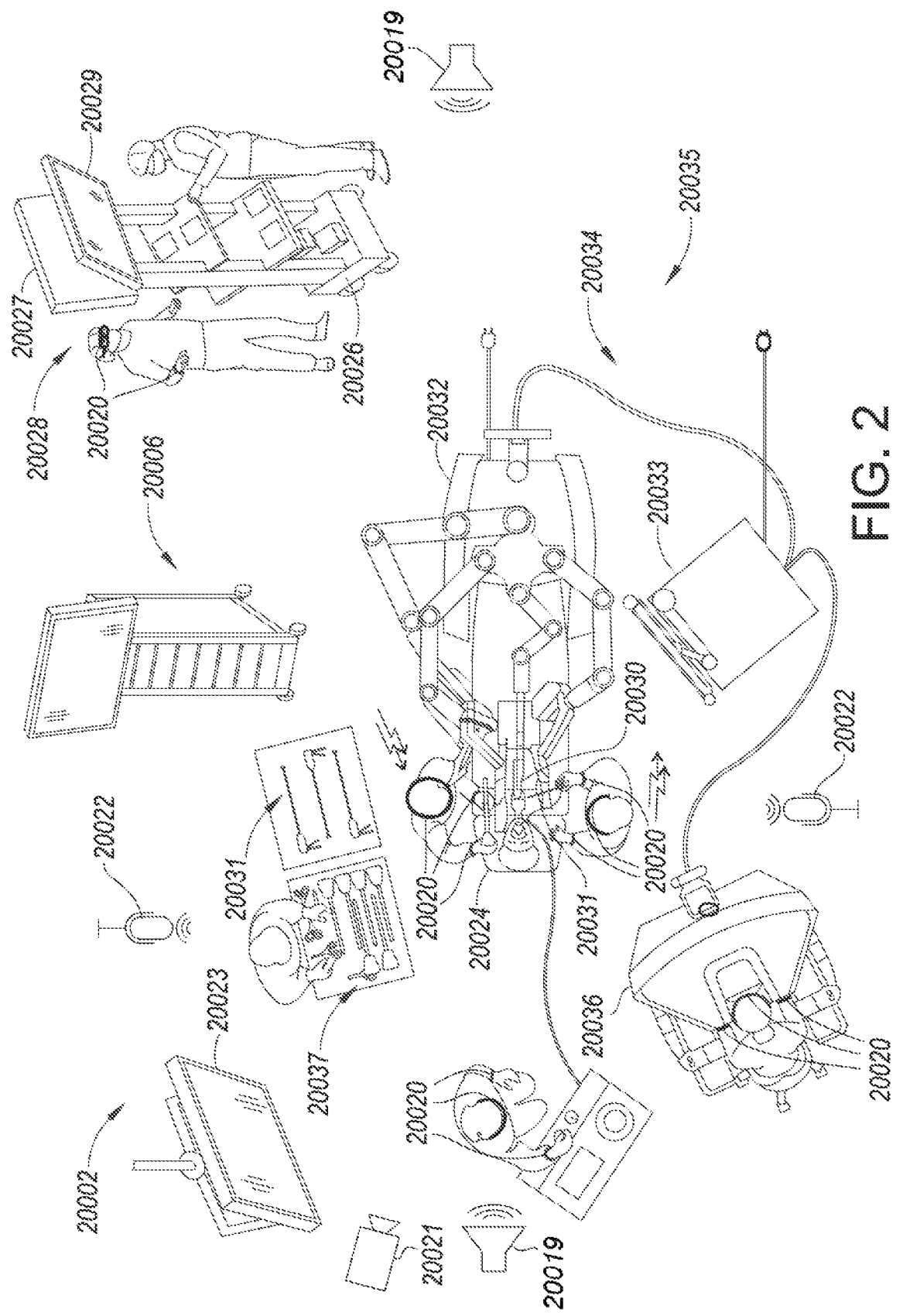
FIG. 2 shows an example surgical system in a surgical operating room.

FIG. 2 shows an example of a surgical system 20002 in a surgical operating room. As illustrated in FIG. 2, a patient is being operated on by one or more health care professionals (HCPs). The HCPs are being monitored by one or more HCP sensing systems 20020 worn by the HCPs. The HCPs and the environment surrounding the HCPs may also be monitored by one or more environmental sensing systems including, for example, a set of cameras 20021, a set of microphones 20022, and other sensors that may be deployed in the operating room. The HCP sensing systems 20020 and the environmental sensing systems may be in communication with a surgical hub 20006, which in turn may be in communication with one or more cloud servers 20009 of the cloud computing system 20008, as shown in FIG. 1A. The environmental sensing systems may be used for measuring one or more environmental attributes, for example, HCP position in the surgical theater, HCP movements, ambient noise in the surgical theater, temperature/humidity m the surgical theater, etc.

As illustrated in FIG. 2, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary HID 20023. The snapshot on the non-sterile display 20027 or 20029 can permit a non-sterile operator to perform a diagnostic step relevant to the surgical procedure, for example.

In one aspect, the surgical hub 20006 may be configured to route a diagnostic input or feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2, a surgical instrument 20031 is being used in the surgical procedure as part of the surgical system 20002. The hub 20006 may be configured to coordinate information flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the surgical system 20002 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 illustrates an example of a surgical system 20002 being used to perform a surgical procedure on a patient who is lying down on an operating table 20024 in a surgical operating room 20035. A robotic system 20034 may be used in the surgical procedure as a part of the surgical system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging device 20030, which can be manipulated by the patient side cart 20032 to orient the imaging device 20030. The robotic hub 20033 can be used to process the images of the surgical site for subsequent display to the surgeon through the surgeon's console 20036.

Other types of robotic systems can be readily adapted for use with the surgical system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is the portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is the portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), tided METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 20030 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 20011 illustrated in FIG. 1A may include one or more sensing systems, for example, HCP sensing systems 20020 as shown in FIG. 2. The HCP sensing systems 20020 may include sensing systems to monitor and detect a set of physical states and/or a set of physiological states of a healthcare personnel (HCP). An HCP may be a surgeon or one or more healthcare personnel assisting the surgeon or other healthcare service providers in general. In an example, a sensing system 20020 may measure a set of biomarkers to monitor the heart rate of an HCP. In an example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include microphones 20022 for measuring the ambient noise in the surgical theater. Other environmental sensing devices may include devices, for example, a thermometer to measure temperature and a hygrometer to measure humidity of the surroundings in the surgical theater, etc. The surgical hub 20006, alone or in communication with the cloud computing system, may use the surgeon biomarker measurement data and/or environmental sensing information to modify the control algorithms of hand-held instruments or the averaging delay of a robotic interface, for example, to minimize tremors. In an example, the HCP sensing systems 20020 may measure one or more surgeon biomarkers associated with an HCP and send the measurement data associated with the surgeon biomarkers to the surgical hub 20006. The HCP sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following-stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with an HCP to adaptively control one or more surgical instruments 20031. For example, the surgical hub 20006 may send a control program to a surgical instrument 20031 to control its actuators to limit or compensate for fatigue and use of fine motor skills. The surgical hub 2000r6 may send the control program based on situational awareness and/or the context on importance or criticality of a task. The control program may instruct the instrument to alter operation to provide more control when control is needed.

Figure 3:
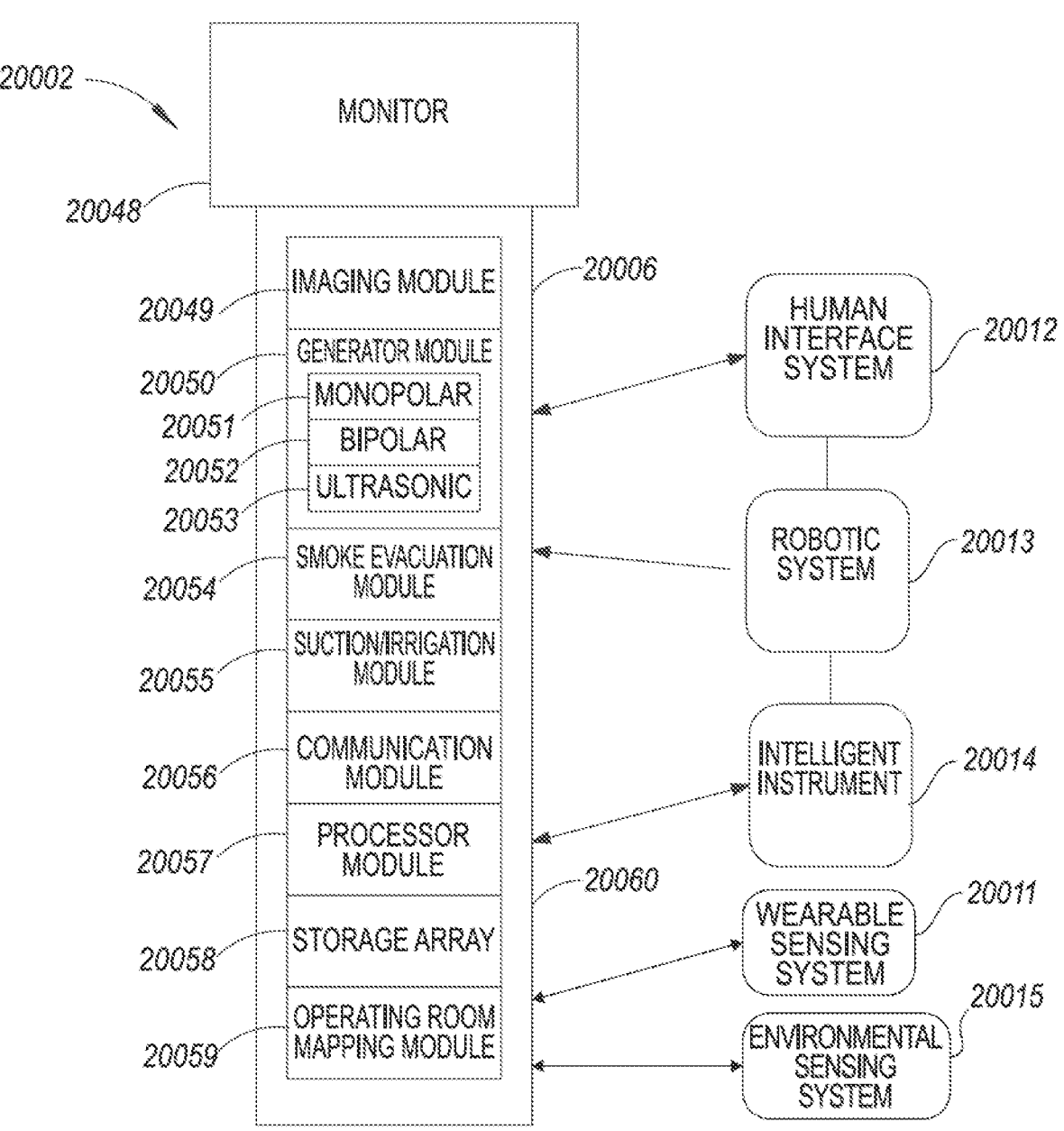
FIG. 3 illustrates an example surgical hub paired with various systems.

FIG. 3 shows an example surgical system 20002 with a surgical hub 20006 paired with a wearable sensing system 20011, an environmental sensing system 20015, a human interface system 20012, a robotic system 20013, and an intelligent instrument 20014. The hub 20006 includes a display 20048, an imaging module 20049, a generator module 20050, a communication module 20056, a processor module 20057, a storage array 20058, and an operating-room mapping module 20059. In certain aspects, as illustrated in FIG. 3, the hub 20006 further includes a smoke evacuation module 20054 and/or a suction/irrigation module 20055. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclosure 20060 and a combo generator module slidably receivable in a docking station of the hub enclosure 20060. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20060 is configured to accommodate different generators and facilitate an interactive communication therebetween. One of the advantages of the hub modular enclosure 20060 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 20060 that allows the modular integration of a generator module 20050, a smoke evacuation module 20054, and a suction/irrigation module 20055. The hub modular enclosure 20060 further facilitates interactive communication between the modules 20059, 20054, and 20055. The generator module 20050 can be with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and/or ultrasonic generator modules that interact through the hub modular enclosure 20060. The hub modular enclosure 20060 can be configured to facilitate the insertion of multiple generators and interactive communication between the generators docked into the hub modular enclosure 20060 so that the generators would act as a single generator.

Figure 4:
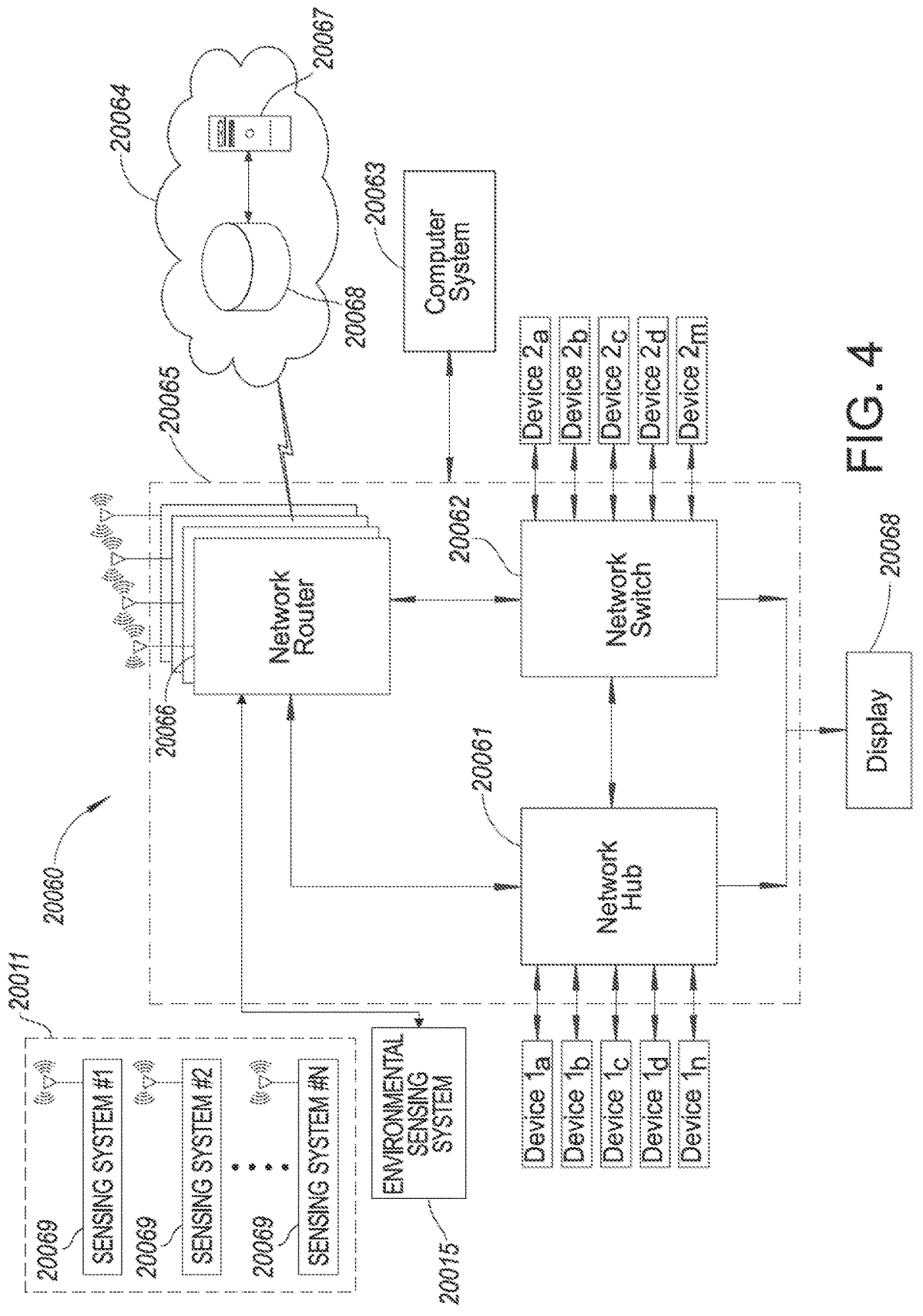
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, environment sensing system(s), and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 20060 may include a modular communication hub 20065 that is configured to connect modular devices located in a healthcare facility to a cloud-based system (e.g., a cloud computing system 20064 that may include a remote server 20067 coupled to a remote storage 20068). The modular communication hub 20065 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a local computer system 20063 to provide local computer processing and data manipulation.

The computer system 20063 may comprise a processor and a network interface 20100. The processor may be coupled to a communication module, storage, memory, non-volatile memory, and input/output (I/O) interface via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with Stellar-isWare® software, a 2 KB electrically erasable program-mable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 20063 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use some of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 20063 can operate in a networked environment using logical connections to one or more remote computers, such as cloud computer(s), or local computers. The remote cloud computer(s) can be a personal computer, server, router, network PC, workstation, micro-processor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

In various examples, the computer system 20063 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1a-1n located in the operating theater may be coupled to the modular communication hub 20065. The network hub 20061 and/or the network switch 20062 may be coupled to a network router 20066 to connect the devices 1a-1n to the cloud computing system 20064 or the local computer system 20163. Data associated with the devices 1a-1n may be transferred to cloud-based computers via the router for remote data processing and manipulation. Data associated with the devices 1a-1 may also be transferred to the local computer system 20063 for local data processing and manipulation. Modular devices 2a-2m located in the same operating theater also may be coupled to a network switch 20062. The network switch 20062 may be coupled to the network hub 20061 and/or the network router 20066 to connect the devices 2a-2m to the cloud 20064. Data associated with the devices 2a-2m may be transferred to the cloud computing system 20064 via the network router 20066 for data processing and manipulation. Data associated with the devices 2a-2m may also be transferred to the local computer system 20063 for local data processing and manipulation.

The wearable sensing system 20011 may include one or more sensing systems 20069. The sensing systems 20069 may include an HCP sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the network router 20066 to connect to the sensing systems 20069 to the local computer system 20063 and/or the cloud computing system 20064. Data associated with the sensing systems 20069 may be transferred to the cloud computing system 20064 via the network router 20066 for data processing and manipulation. Data associated with the sensing systems 20069 may also be transferred to the local computer system 20063 for local data processing and manipulation.

As illustrated in FIG. 4, the surgical hub system 20060 may be expanded by interconnecting multiple network hubs 20061 and/or multiple network switches 20062 with multiple network routers 20066. The modular communication hub 20065 may be contained in a modular control tower configured to receive multiple devices 1a-1n/2a-2m. The local computer system 20063 also may be contained in a modular control tower. The modular communication hub 20065 may be connected to a display 20068 to display images obtained by some of the devices 1a-1n/2a-2m, for example during surgical procedures. In various aspects, the devices 1a-1n/2a-2m may include, for example, various modules such as an imaging module coupled to an endoscope, a generator module coupled to an energy-based surgical device, a smoke evacuation module, a suction/irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1a-1n/2a-2m or the sensing systems 20069 to the cloud-base system 20064. One or more of the devices 1a-1n/2a-2m or the sensing systems 20069 coupled to the network hub 20061 or network switch 20062 may collect data in real-time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 20065 and/or computer system 20063 located in the surgical theater (e.g., a fixed, mobile, temporary, or field operating room or space) and to devices connected to the modular communication hub 20065 and/or computer system 20063 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, sensing systems, and other computerized devices located in the operating theater. The hub hardware enables multiple devices, sensing systems, and/or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud computing system 20064 or the local computer system 20063 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data collected by the sensing systems 20069, the surgical data network can provide improved surgical outcomes, improved recovery outcomes, reduced costs, and improved patient satisfaction. At least some of the sensing systems 20069 may be employed to assess physiological conditions of a surgeon operating on a patient or a patient being prepared for a surgical procedure or a patient recovering after a surgical procedure. The cloud-based computing system 20064 may be used to monitor biomarkers associated with a surgeon or a patient m real-time and to generate surgical plans based at least on measurement data gathered prior to a surgical procedure, provide control signals to the surgical instruments during a surgical procedure, and notify a patient of a complication during post-surgical period.

The operating theater devices 1a-1n may be connected to the modular communication hub 20065 over a wired channel or a wireless channel depending on the configuration of the devices 1a-1n to a network hub 20061. The network hub 20061 may be implemented, in one aspect, as a local network broadcast device that works on the physical layer of the Open System Interconnection (OSI) model. The network hub may provide connectivity to the devices 1a-1n located in the same operating theater network. The network hub 20061 may collect data in the form of packets and sends them to the router in half duplex mode. The network hub 20061 may not store any media access control/Internet Protocol (MAC/IP) to transfer the device data. Only one of the devices 1a-1n can send data at a time through the network hub 20061. The network hub 20061 may not have routing tables or intelligence regarding where to send information and broadcasts all network data across each connection and to a remote server 20067 of the cloud computing system 20064. The network hub 20061 can detect basic network errors such as collisions but having all information broadcast to multiple ports can be a security risk and cause bottlenecks.

The operating theater devices 2a-2m may be connected to a network switch 20062 over a wired channel or a wireless channel. The network switch 20062 works in the data link layer of the OSI model. The network switch 20062 may be a multicast device for connecting the devices 2a-2m located in the same operating theater to the network. The network switch 20062 may send data in the form of frames to the network router 20066 and may work in full duplex mode. Multiple devices 2a-2m can send data at the same time through the network switch 20062. The network switch 20062 stores and uses MAC addresses of the devices 2a-2m to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or network switch 20062 to cloud-based computer resources for further processing and manipulation of the data collected by any one of or all the devices 1a-1n/2a-2m and wearable sensing system 20011. The network router 20066 may be employed to connect two or more different networks located in different locations, such as, for example, different operating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20016 may be implemented as a USB hub, which allows multiple USB devices to be connected to a host computer. The USB hub may expand a single USB port into several tiers so that there are more ports available to connect devices to the host system computer. The network hub 20061 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m and/or the sensing systems 20069 may communicate to the modular communication hub 20065 via Bluetooth wireless technology standard for exchanging data over short distances (using short-wavelength UHF radio waves m the ISM band from 2.4 to 2.485 GHz) from fixed and mobile devices and building personal area networks (PANs). The operating theater devices 1a-1n/2a-2m and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WiMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1a-1n/2a-2m and/or the sensing systems 20069 and may handle a data type known as frames. Frames may carry the data generated by the devices 1a-1n/2a-2m and/or the sensing systems 20069. When a frame is received by the modular communication hub 20065, it may be amplified and/or sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1a-1n/2a-2m.

Figure 5:
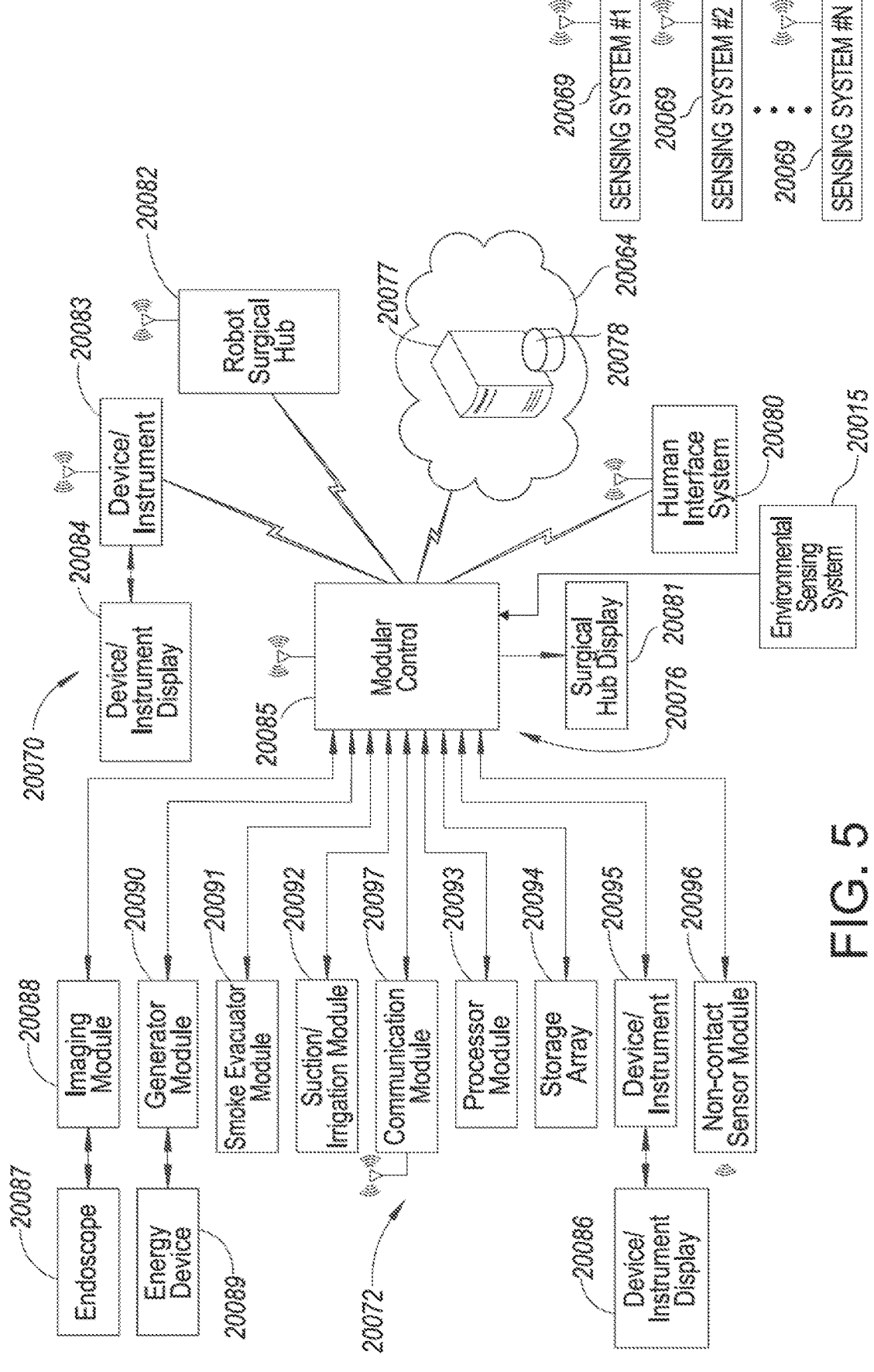
FIG. 5 illustrates an example computer-implemented interactive surgical system that may be part of a surgical system.

FIG. 5 illustrates a computer-implemented interactive surgical system 20070 that may be a part of the Surgical system 20002. The computer-implemented interactive surgical system 20070 is similar in many respects to the HCP sensing system 20002. For example, the computer-implemented interactive surgical system 20070 may include one or more surgical sub-systems 20072, which are similar in many respects to the Surgical systems 20002. Each sub-surgical system 20072 may include at least one surgical hub 20076 in communication with a cloud computing system 20064 that may include a remote server 20077 and a remote storage 20078. In one aspect, the computer-implemented interactive surgical system 20070 may include a modular control 20085 connected to multiple operating theater devices such as sensing systems 20001, intelligent surgical instruments, robots, and other computerized devices located in the operating theater.

As illustrated in the example of FIG. 5, the modular control 20085 may be coupled to an imaging module 20088 that may be coupled to an endoscope 20087, a generator module 20090 that may be coupled to an energy device 20089, a smoke evacuator module 20091, a suction/irrigation module 20092, a communication module 20097, a processor module 20093, a storage array 20094, a smart device/instrument 20095 optionally coupled to a display 20086 and 20084 respectively, and a non-contact sensor module 20096. The non-contact sensor module 20096 may measure the dimensions of the operating theater and generate a map of the surgical theater using, ultrasonic, laser-type, and/or the like, non-contact measurement devices. Other distance sensors can be employed to determine the bounds of an operating room. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The modular control 20085 may also be in communication with one or more sensing systems 20069 and an environmental sensing system 20015. The sensing systems 20069 may be connected to the modular control 20085 either directly via a router or via the communication module 20097. The operating theater devices may be coupled to cloud computing resources and data storage via the modular control 20085. A robot surgical hub 20082 also may be connected to the modular control 20085 and to the cloud computing resources. The devices/instruments 20095 or 20084, human interface system 20080, among others, may be coupled to the modular control 20085 via wired or wireless communication standards or protocols, as described herein. The human interface system 20080 may include a display sub-system and a notification sub-system. The modular control 20085 may be coupled to a hub display 20081 (e.g., monitor, screen) to display and overlay images received from the imaging module 20088, device/instrument display 20086, and/or other human interface systems 20080. The hub display 20081 also may display data received from devices connected to the modular control 20085 in conjunction with images and overlaid images.

Figure 6:
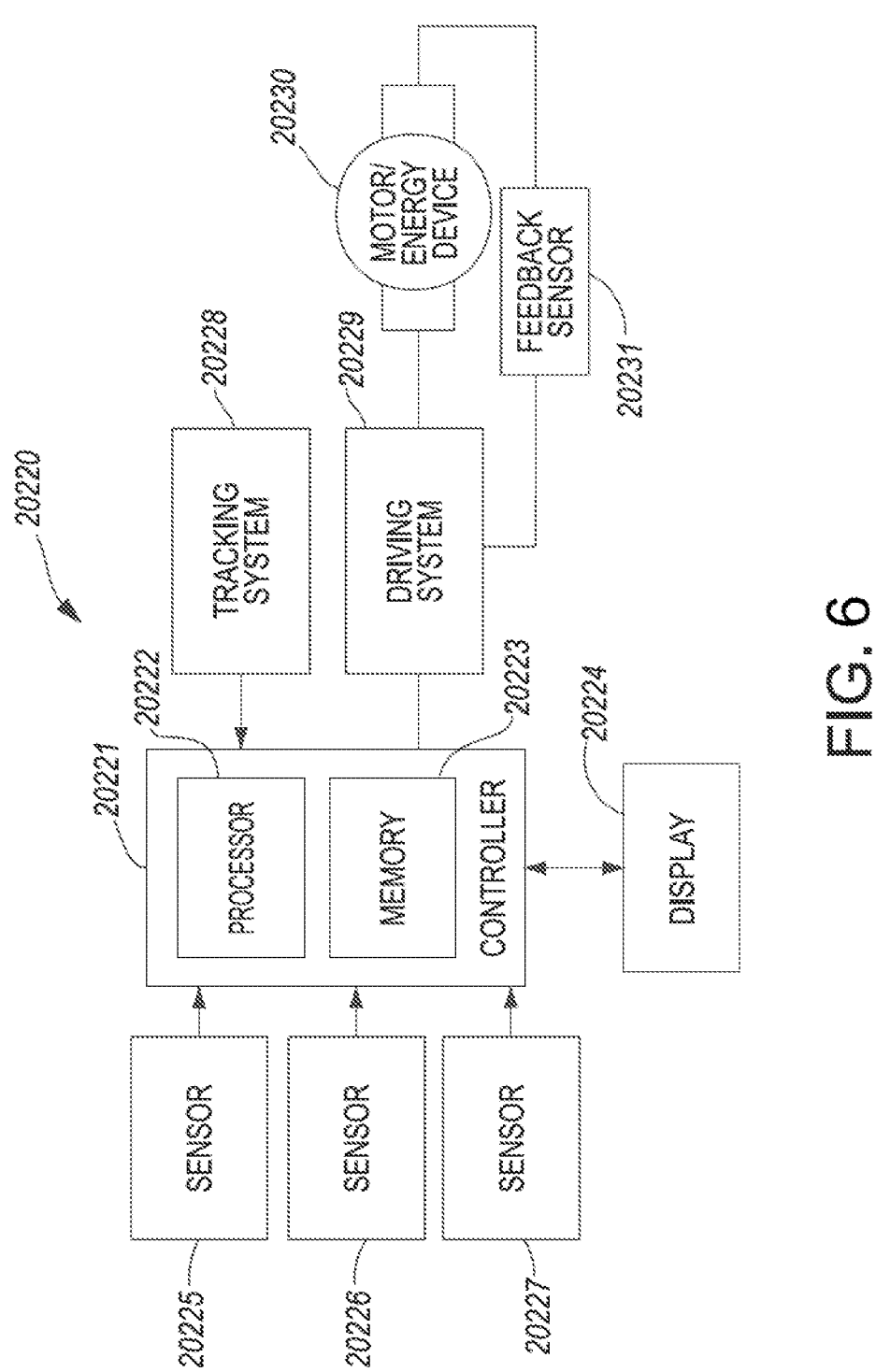
FIG. 6 illustrates a logic diagram of a control system of a surgical instrument.

FIG. 6 illustrates a logical diagram of a control system 20220 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like.

The system 20220 may comprise a control circuit. The control circuit may include a microcontroller 20221 comprising a processor 20222 and a memory 20223. One or more sensors 20225, 20226, 20227, for example, provide real-time feedback to the processor 20222. A motor 20230, driven by a motor driver 20229, operably couples a longitudinally movable displacement member to drive the I-beam knife element. A tracking system 20228 may be configured to determine the position of the longitudinally movable displacement member. The position information may be provided to the processor 20222, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 20224 may display a variety of operating conditions of the instruments and may include touch screen functionality for data input. Information displayed on the display 20224 may be overlaid with images acquired via endoscopic imaging modules.

The microcontroller 20221 may be any single-core or multicore processor such as those known under the trade name ARM Cortex by Texas Instruments. In one aspect, the main microcontroller 20221 may be an LM4F230H5QR ARM Cortex-M4F Processor Core, available from Texas Instruments, for example, comprising an on-chip memory of 256 KB single-cycle flash memory, or other non-volatile memory, up to 40N MHz, a prefetch buffer to improve performance above 40 MHz, a 32 KB single-cycle SRAM, and internal ROM loaded with StellatisWare® software, a 2 KB EEPROM, one or more PWM modules, one or more QEI analogs, and/or one or more 12-bit ADCs with 12 analog input channels, details of which are available for the product datasheet.

The microcontroller 20221 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 20221 may be programmed to perform various functions such as precise control over the speed and position of the knife and articulation systems. In one aspect, the microcontroller 20221 may include a processor 20222 and a memory 20223. The electric motor 20230 may be a brushed direct current (DC) motor with a gearbox and mechanical links to an articulation or knife system. In one aspect, a motor driver 20229 may be an A3941 available from Allegro Microsystems, Inc. Other motor drivers may be readily substituted for use in the tracking system 20228 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 20221 may be programmed to provide precise control over the speed and position of displacement members and articulation systems. The microcontroller 20221 may be configured to compute a response in the software of the microcontroller 20221. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

The motor 20230 may be controlled by the motor driver 20229 and can be employed by the firing system of the surgical instrument or tool. In various forms, the motor 20230 may be a brushed DC driving motor having a maximum rotational speed of approximately 25,000 RPM. In some examples, the motor 20230 may include a brushless motor, a cordless motor, a synchronous motor, a stepper motor, or any other suitable electric motor. The motor driver 20229 may comprise an H-bridge driver comprising field-effect transistors (FETs), for example. The motor 20230 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 20229 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 20229 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 20228 comprising an absolute positioning system.

The tracking system 20228 may comprise a controlled motor drive circuit arrangement comprising a position sensor 20225 according to one aspect of this disclosure. The position sensor 20225 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 20225 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 20230 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 20225 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 20225 may be equivalent to a longitudinal linear displacement d1 of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 20225 completing one or more revolutions for the full stroke of the displacement member. The position sensor 20225 may complete multiple revolutions for the full stroke of the displacement member.

A series of switches, where n is an integer greater than one, may be employed alone or in combination with a gear reduction to provide a unique position signal for more than one revolution of the position sensor 20225. The state of the switches may be fed back to the microcontroller 20221 that applies logic to determine a unique position signal corresponding to the longitudinal linear displacement d1+d2+ . . . dn of the displacement member. The output of the position sensor 20225 is provided to the microcontroller 20221. The position sensor 20225 of the sensor arrangement may comprise a magnetic sensor, an analog rotary sensor like a potentiometer, or an array of analog Hall-effect elements, which output a unique combination of position signals or values.

The position sensor 20225 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

The position sensor 20225 for the tracking system 20228 comprising an absolute positioning system may comprise a magnetic rotary absolute positioning system. The position sensor 20225 may be implemented as an AS5055EQFT single-chip magnetic rotary position sensor available from Austria Microsystems, AG. The position sensor 20225 is interfaced with the microcontroller 20221 to provide an absolute positioning system. The position sensor 20225 may be a low-voltage and low-power component and may include four Hall-effect elements in an area of the position sensor 20225 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 20221. The position sensor 20225 may provide 12 or 14 bits of resolution. The position sensor 20225 may be an AS5055 chip provided in a small QFN 16-pin 4×4×0.85 mm package.

The tracking system 20228 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 20225. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 20230 has taken to infer the position of a device actuator, drive bar, knife, or the like.

A sensor 20226, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 20222. Alternatively, or in addition to the sensor 20226, a sensor 20227, such as, for example, a load sensor, can measure the closure force applied by the closure drive system to the anvil. The sensor 20227, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 20231 can be employed to measure the current drawn by the motor 20230. The force required to advance the firing member can correspond to the current drawn by the motor 20230, for example. The measured force may be converted to a digital signal and provided to the processor 20222.

For example, the strain gauge sensor 20226 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 20226, such as, for example, a micro-strain gauge, that can be configured to measure one or more parameters of the end effector, for example. In one aspect, the strain gauge sensor 20226 can measure the amplitude or magnitude of the strain exerted on a jaw member of an end effector during a clamping operation, which can be indicative of the tissue compression. The measured strain can be converted to a digital signal and provided to a processor 20222 of the microcontroller 20221. A load sensor 20227 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 20222.

The measurements of the tissue compression, the tissue thickness, and/or the force required to close the end effector on the tissue, as respectively measured by the sensors 20226, 20227, can be used by the microcontroller 20221 to characterize the selected position of the firing member and/or the corresponding value of the speed of the firing member. In one instance, a memory 20223 may store a technique, an equation, and/or a lookup table which can be employed by the microcontroller 20221 in the assessment.

The control system 20220 of the surgical instrument or tool also may comprise wired or wireless communication circuits to communicate with the modular communication hub 20065 as shown in FIG. 5.

Figure 7:
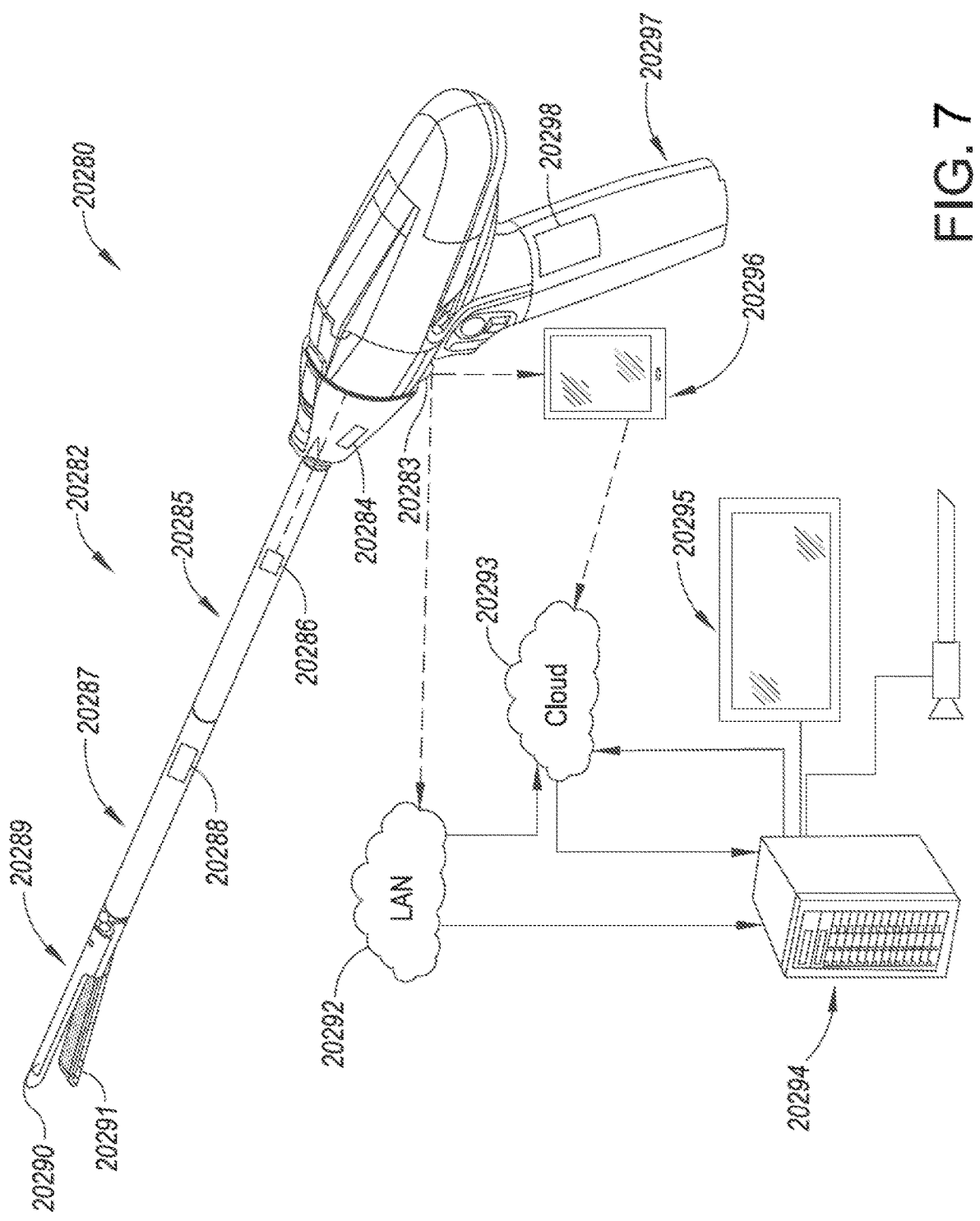
FIG. 7 shows an example surgical system that includes a handle having a controller and a motor, an adapter releasably coupled to the handle, and a loading unit releasably coupled to the adapter.

FIG. 7 illustrates an example surgical system 20280 in accordance with the present disclosure and may include a surgical instrument 20282 that can be in communication with a console 20294 or a portable device 20296 through a local area network 20292 and/or a cloud network 20293 via a wired and/or wireless connection. The console 20294 and the portable device 20296 may be any suitable computing device. The surgical instrument 20282 may include a handle 20297, an adapter 20285, and a loading unit 20287. The adapter 20285 releasably couples to the handle 20297 and the loading unit 20287 releasably couples to the adapter 20285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touchscreens, and any other suitable input mechanisms or user interfaces, which can be engaged by a clinician to activate the motor.

The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 20285 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive shafts, the strain of the drive shafts, the temperature within the adapter 20285, a number of firings of the adapter 20285, a peak force of the adapter 20285 during firing, a total amount of force applied to the adapter 20285, a peak retraction force of the adapter 20285, a number of pauses of the adapter 20285 during firing, etc.). The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during firing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit instrument data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub. The transceiver 20283 may receive data (e.g., cartridge data, loading unit data, adapter data, or other notifications) from the surgical hub 20270. The transceiver 20283 may receive data (e.g., cartridge data, loading unit data, or adapter data) from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figure 8:
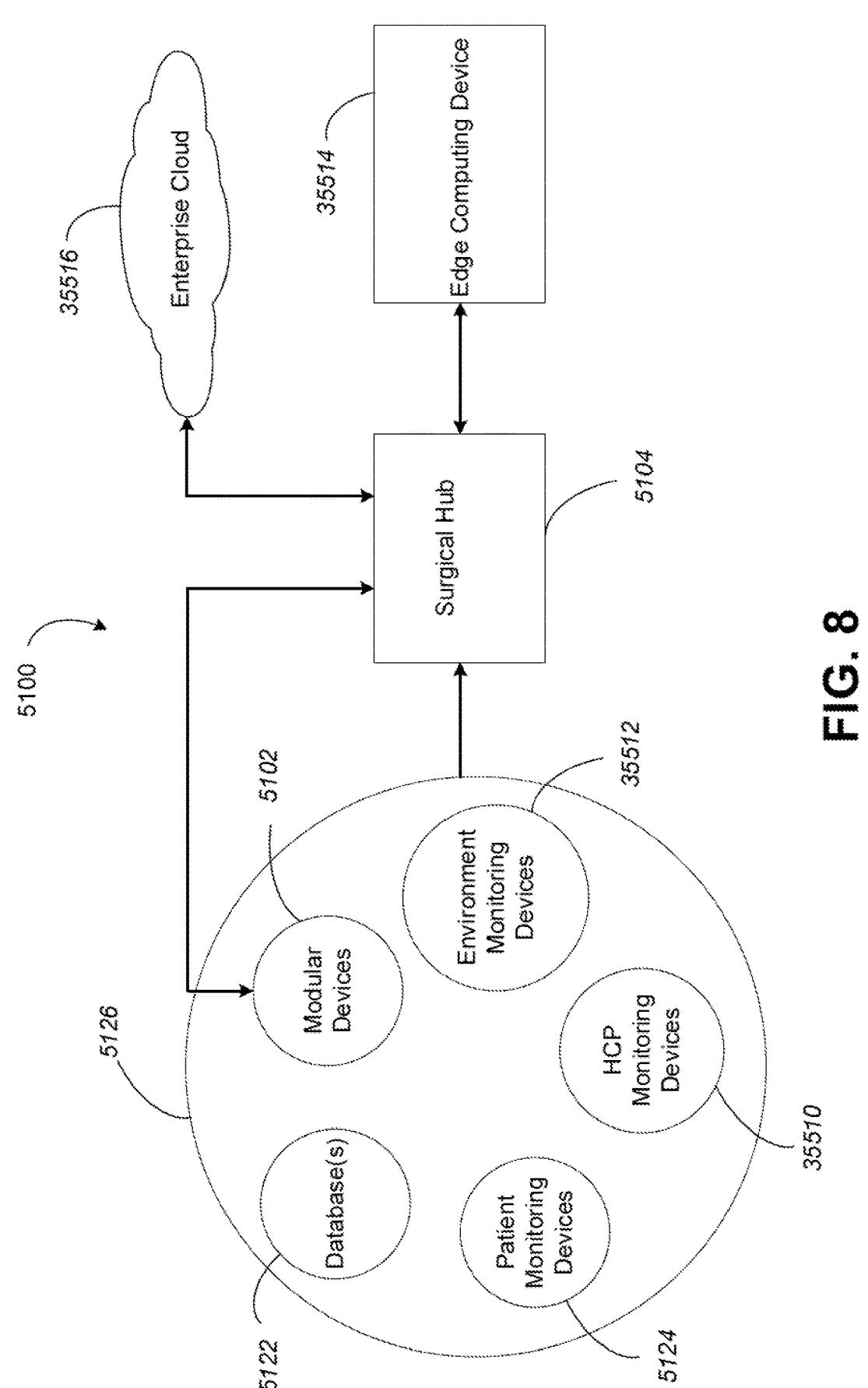
FIG. 8 shows an example situationally aware surgical system.

FIG. 8 illustrates a diagram of a situationally aware surgical system 5100, in accordance with at least one aspect of the present disclosure. The data sources 5126 may include, for example, the modular devices 5102 (which can include sensors configured to detect parameters associated with the patient, HCPs and environment and/or the modular device itself), databases 5122 (e.g., an EMR database containing patient records), patient monitoring devices 5124 (e.g., a blood pressure (BP) monitor and an electrocardiography (EKG) monitor), HCP monitoring devices 35510, and/or environment monitoring devices 35512. The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." For example, the surgical hub 5104 can incorporate a situational awareness system, which is the hardware and/or programming associated with the surgical hub 5104 that derives contextual information pertaining to the surgical procedure from the received data and/or a surgical plan information received from the edge computing system 35514 or an enterprise cloud server 35516.

The situational awareness system of the surgical hub 5104 can be configured to derive the contextual information from the data received from the data sources 5126 in a variety of different ways. For example, the situational awareness system can include a pattern recognition system, or machine learning system (e.g., an artificial neural network), that has been trained on training data to correlate various inputs (e.g., data from database(s) 5122, patient monitoring devices 5124, modular devices 5102, HCP monitoring devices 35510, and/or environment monitoring devices 35512) to corresponding contextual information regarding a surgical procedure. A machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (e.g., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (e.g., whether bleeding at a surgical site has stopped) according to video or image data received from a medical imaging device. The surgical hub 5104 can be further configured to compare a physiologic measurement (e.g., blood pressure sensed by a BP monitor communicably connected to the surgical hub 5104) with the visual or image data of hemostasis (e.g., from a medical imaging device communicably coupled to the surgical hub 5104) to make a determination on the integrity of the staple line or tissue weld. The situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use as soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could proactively change the displayed view (supplied by, e.g., a medical imaging device for the visualization system) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can compare the list of items for the procedure and/or a list of devices paired with the surgical hub 5104 to a recommended or anticipated manifest of items and/or devices for the given surgical procedure. If there are any discontinuities between the lists, the surgical hub 5104 can provide an alert indicating that a particular modular device 5102, patient monitoring device 5124, HCP monitoring devices 35510, environment monitoring devices 35512, and/or other surgical item is missing. In some examples, the surgical hub 5104 can determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other HCP(s)) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. The surgical hub 5104 can provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Figure 9:
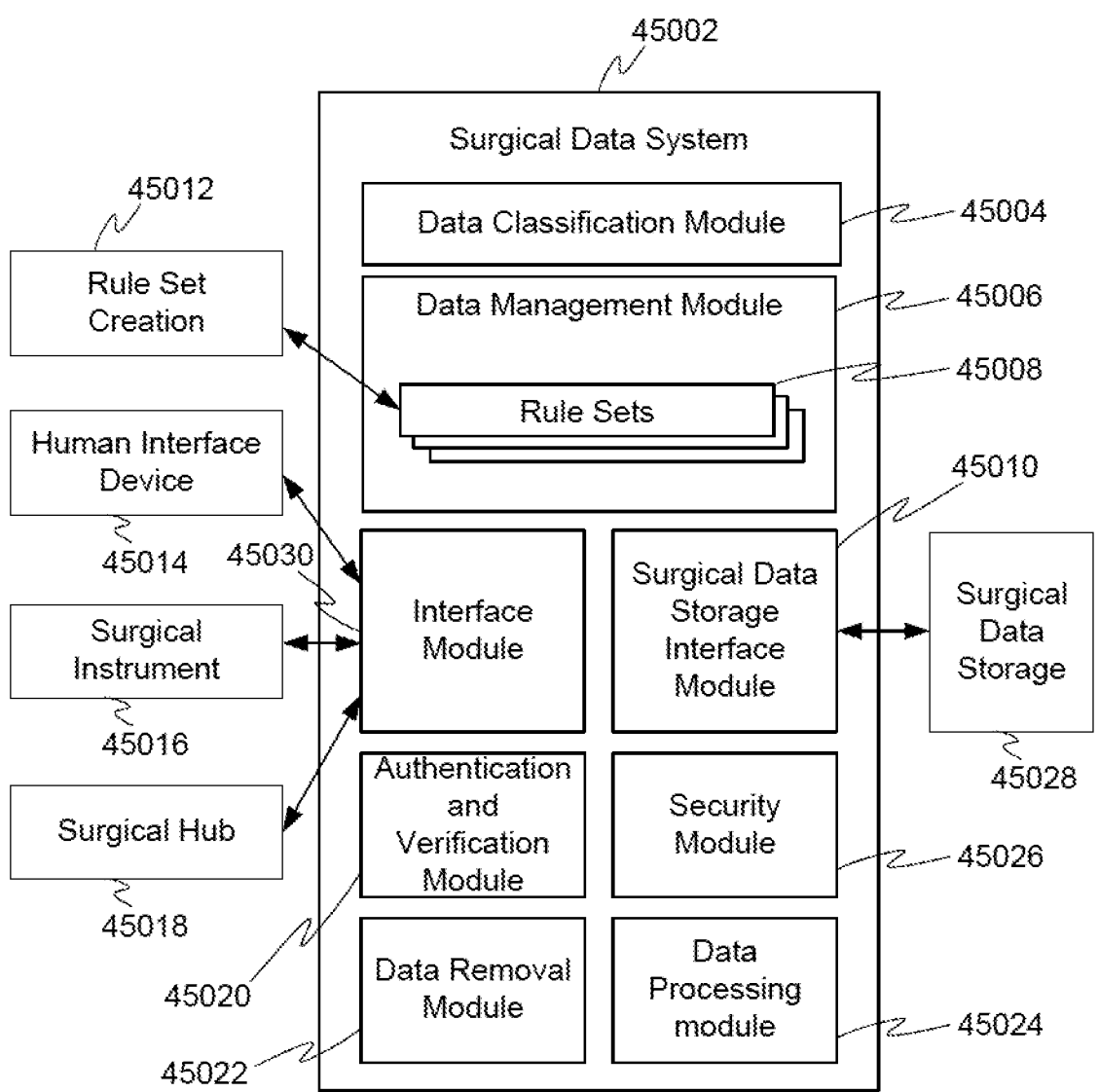
FIG. 9 shows an example surgical data system.

FIG. 9 shows an example surgical data system. The surgical data system 45002 may support functionalities of a surgical hub, for example, the surgical hub 20006 in FIG. 3. The surgical data system 45002 may support functionalities of various modules of a surgical hub, for example, the various modules in the surgical hub 20006 of FIG. 3. The surgical data system 45002 may be part of a surgical hub, for example, the surgical hub 20006 in FIG. 3. The surgical data system 45002 may be part of a processor module of a surgical hub, for example, the processor module 20057 of the surgical hub 20006. The surgical data system 45002 may be a stand-alone system.

The surgical data system 45002 may include any hardware and/or software suitable for providing functionalities of managing and processing surgical information. The surgical data system 45002 may provide functionalities to support the structure and/or functions described in connection with FIGS. 1-18 herein. For example, the surgical data system 45002 may support one or more elements of a computer-implemented interactive surgical system 20070 in FIG. 5. Examples of data processing that are suitable for use with the surgical data system 45002 are described in U.S. Patent Application Publication No. US 2019-0201033 A1 (U.S. patent application Ser. No. 15/940,663), tided SURGICAL SYSTEM DISTRIBUTED PROCESSING, filed Mar. 29, 2018, the disclosure of which is herein incorporated by reference in its entirety. In one or more of those examples, processing of data may be shared with a handheld instrument with a limited processor. The surgical data system 45002 may include a situational awareness system that is described herein. Examples that are suitable for use with the surgical data system 45002 are described in U.S. Patent Application Publication No. US 2019-0206551 A1 (U.S. patent application Ser. No. 15/940,666), titled SPATIAL AWARENESS OF SURGICAL HUBS IN OPERATING ROOMS, filed Mar. 29, 2018, the disclosure of which is herein incorporated by reference in its entirety. In one or more of those examples, a surgical hub may identify the bounds of an operating space.

The surgical data system 45002 may include one or more functional modules. Each module may include hardware, software, or a combination thereof that enable functionality of the module. One or more modules, operating in concert or otherwise, may enable authentication and verification of data, data security, database integration, data classification, data processing, data removal and big data management. The modules may include hardware elements, such as a computer processing unit, a graphics processing unit, a field-programmable gate array (FPGAs), communications hardware, memory, and the like. The modules may include software elements that when executed by a processor cause the modules to perform the functionalities of the modules.

The surgical data system 45002 may include an interface module 45030. The interface module 45030 may enable communication with one or more of a human interface device 45014, a surgical instrument 45016, or a surgical hub 45018. The human interface device 45014 may include a display. In some examples, the surgical hub 45018 may be the surgical hub 20006 that has a communication module 20056. The surgical data system 45002 may include, for example, on or more surgical data repositories. The surgical data system 45002 may interact with a surgical data storage 45028 through the surgical data storage interface module 45010. In an example, the surgical data storage 45028 may include the remote server 20067 of the cloud computing system 20064 in FIG. 4.

The surgical data system 45002, may obtain data, for example, from various OR equipment and sensing devices, as shown in FIG. 2. For example, the data may include any surgical data collected from the various OR equipment and sensing devices. For example, the surgical data system 45002 may receive data directly from any of the networked devices disclosed in FIGS. 1-8. Such data may include information about a live surgical procedure, for example. Such data may include information about a past surgical procedure. Such data may include information about future, scheduled surgical procedures. Examples of data this is suitable for use with the present disclosure are described in U.S. Patent Application Publication No. US 2019-0207773 A1 (U.S. patent application Ser. No. 15/940,645), tided SELF DESCRIBING DATA PACKETS GENERATED AT AN ISSUING INSTRUMENT, filed Mar. 29, 2018, the disclosure of which is herein incorporated by reference in its entirety. In one or more of those examples, self-describing data may allow a processor to interpret data without having been told in advance of its receipt.

Information about surgical procedures (e.g., surgical information) may include information about the patient, the staff, the procedure as planned, the procedure as experienced, and post-operative activity including patient outcomes. For example, the information received and used by the surgical data system 45002 may include patient records, patient imaging, models of patient anatomy, patient lab results, patient medical history, and the like. For example, the information received and used by the surgical data system 45002 may include a staff manifest for a procedure, details about the past procedures of the specific staff members, staff metrics, experience, recent scheduling and work-load, and historical surgical activity, such instrument use statistics, procedure duration, and the like. For example, the information received and used by the surgical data system 45002 may include procedure plans, equipment and inventory information, pull-lists, checklists, procedure plan analysis and recommendations. For example, the information received and used by the surgical data system 45002 may include any data collected or generated during a live procedure, such as procedure progress, milestones, patient information, vitals, operating theater setup, staff movement, imaging, instrument use, surgical technique, such as that captured by video, recorded manually, and/or inferred from smart-instrument reporting for example, duration, abnormal event reporting, and the like. Any data captured during a live procedure may also be stored and made available as a past procedure. For example, the information received and used by the surgical data system 45002 may include post-operative records, patient recovery information, and patient outcome information, post-operative diagnostic information, such as labs, imaging, et.

The surgical data system 45002 may include authentication and verification module 45020. The authentication and verification module 45020 may authenticate and/or verify surgical data that the device receives by employing the surgical data system 45002. Examples that are suitable for use with the authentication and verification module 45020 are described in in U.S. Patent Application Publication No. US 2019-0205441 A1 (U.S. patent application Ser. No. 16/182,224), titled SURGICAL NETWORK, INSTRUMENT, AND CLOUD RESPONSES BASED ON VALIDATION OF RECEIVED DATASET AND AUTHENTICATION OF ITS SOURCE AND INTEGRITY, filed Nov. 6, 2018, the disclosure of which is herein incorporated by reference in its entirety. In one or more of those examples, hub, instrument, and cloud responses may operate based on validation of a received dataset and authentication of its source and integrity. One or more of the responses may be a choice of reactions to either the data or metadata.

The surgical data system 45002 may include security module 45026. In an example, the security module 45026 may provide security of monitoring authenticity and sterility of manual device assisting in robotic case. Examples that are suitable for use with the security module 45026 are described in in U.S. Patent Application Publication No. US 2019-0207911 A1 (U.S. patent application Ser. No. 15/940, 641), titled INTERACTIVE SURGICAL SYSTEMS WITH ENCRYPTED COMMUNICATIONS CAPABILITIES, filed Mar. 29, 2018, the disclosure of which is herein incorporated by reference in its entirety. In one or more of those examples, mantle generator data may be encrypted and communicated through the internet. Examples that are suitable for use with the security module 45026 are described in in U.S. Patent Application Publication No. US 2019-0206216 A1 (U.S. patent application Ser. No. 16/182,248), titled DETECTION AND ESCALATION OF SECURITY RESPONSES OF SURGICAL INSTRUMENTS TO INCREASING SEVERITY THREATS, filed Nov. 6, 2018, the disclosure of which is herein incorporated by reference in its entirety. In one or more of those examples, a wireless pair surgical instrument may detect and escalate security responses to numerous or increasing severity threats.

The surgical data system 45002 may include a data management module 45006. The data management module 45006 may provide management of a data stream, and/or an organization and structure of the data stream, for example, to facilitate an integration of the data stream into a databases or multiple databases. The data management module 45006 may provide management of a data stream, and/or an organization and structure of the data stream, for example, by selecting one or more rule sets from rule sets 45008. The rule sets 45008 may be generated via rule set creation 45012. Examples that are suitable for use with the data management module 45006 are described in in U.S. Patent Application Publication No. 2019-0200988 A1 (U.S. patent application Ser. No. 16/024,162), titled SURGICAL SYSTEMS WITH PRIORITIZED DATA TRANSMISSION CAPABILITIES, filed lune 29, 2018, the disclosure of which is herein incorporated by reference in its entirety. In one or more of those examples, same data from two different sources may be prioritized. Examples that are suitable for use with the security module 45026 are described in in U.S. Patent Application Publication No. US 2019-0205567 A1 (U.S. patent application Ser. No. 15/940,649), titled DATA PAIR-ING TO INTERCONNECT A DEVICE MEASURED PARAMETER WITH AN OUTCOME, filed Mar. 29, 2018, the disclosure of which is herein incorporated by reference in its entirety. In one or more of those examples, data pairing method may allow a surgical hub to interconnect a device measured parameter with an outcome.

Data standardization (e.g., data structure standardization) may include one or more of parsing, merging, or processing within a device. For example, the device may include the surgical data system 45002. The device may be a surgical hub, for example, the surgical hub 20006. The device may include a data management module, for example, the data management module 45006 in FIG. 9. Data standardization may enable database integration. Data streams from multiple sources may differ in resolution, sampling rate, measure-ment type, unit type, communication path, importance, data stream type (e.g., discrete or continuous), ee. Data streams (e.g., each data point of each data stream) and the associated metadata may be formatted and/or organized into a standard format such that the formatted data streams can be input into a data base that is in the standard format. For example, the device may adjust the format (e.g., the structure and orga-nization) of a data stream into a standard format to enable annotation or contextual attachment to other data streams. The standard format may be a standardized and organized form.

The device may cooperate with various OR equipment and sensing devices, for example, the various OR equipment and sensing devices as shown in FIG. 2. An OR equipment (or sensing device) may provide a data stream. For example, each of the various OR equipment and sensing devices may provide a respective data stream, and each of the various OR equipment and sensing devices may function as a data source for the respective data stream. The respective data streams may include one or more surgical data streams. The respective data streams may be assimilated, displayed and recorded, for example, in the surgical system shown in FIG. 2. Examples that are suitable for use with the present disclosure are described in in U.S. Patent Application Pub-lication No. US 2019-0206576 A1 (U.S. patent application Ser. No. 16/182,260), tided AUTOMATED DATA SCAL-ING, ALIGNMENT, AND ORGANIZING BASED ON PREDEFINED PARAMETERS WITHIN SURGICAL NETWORKS, filed Nov. 6, 2018, the disclosure of which is herein incorporated by reference in its entirety. In one or more of those examples, automated data scaling, alignment, and organizing may be based on predefined parameters within a surgical hub before transmission.

The respective data streams from the various OR equip-ment and sensing devices may be in different forms and/or frequencies. For example, at least one of a resolution, a sampling rate, a measurement type, a unit of measurement, or a data stream type of a data stream may be different from that of another data stream. A data stream type may be a discrete data stream type or a continuous data stream type. For example, the device may receive data streams from two different patient monitoring devices of the patient monitor-ing devices 5124 in FIG. 8. One of the patient monitoring devices may be a BP monitor, and the other of the patient monitoring devices may be an EKG monitor. Depending on a patient's profile, the BP monitor may be set up to take a measurement every x minutes, and the sampling rate of EKG monitor may be set at y kHz. The data stream received from the BP monitor (the BP data stream) and the data stream received from the EKG monitor (the EKG data stream) may be transformed into a standard format, and the transformed BP data stream and the transformed EKG data stream may be input to a data base that is in the standard format.

The device may organize data streams into standardized formats and associations, for example, to allow for display of relational data with respect to an instrument, a task, and/or the device. For example, the device may process and/or organize data streams into standardized formats and/or asso-ciations using algorithms and/or transformations. The device may be a data standardization device.

Figure 10:
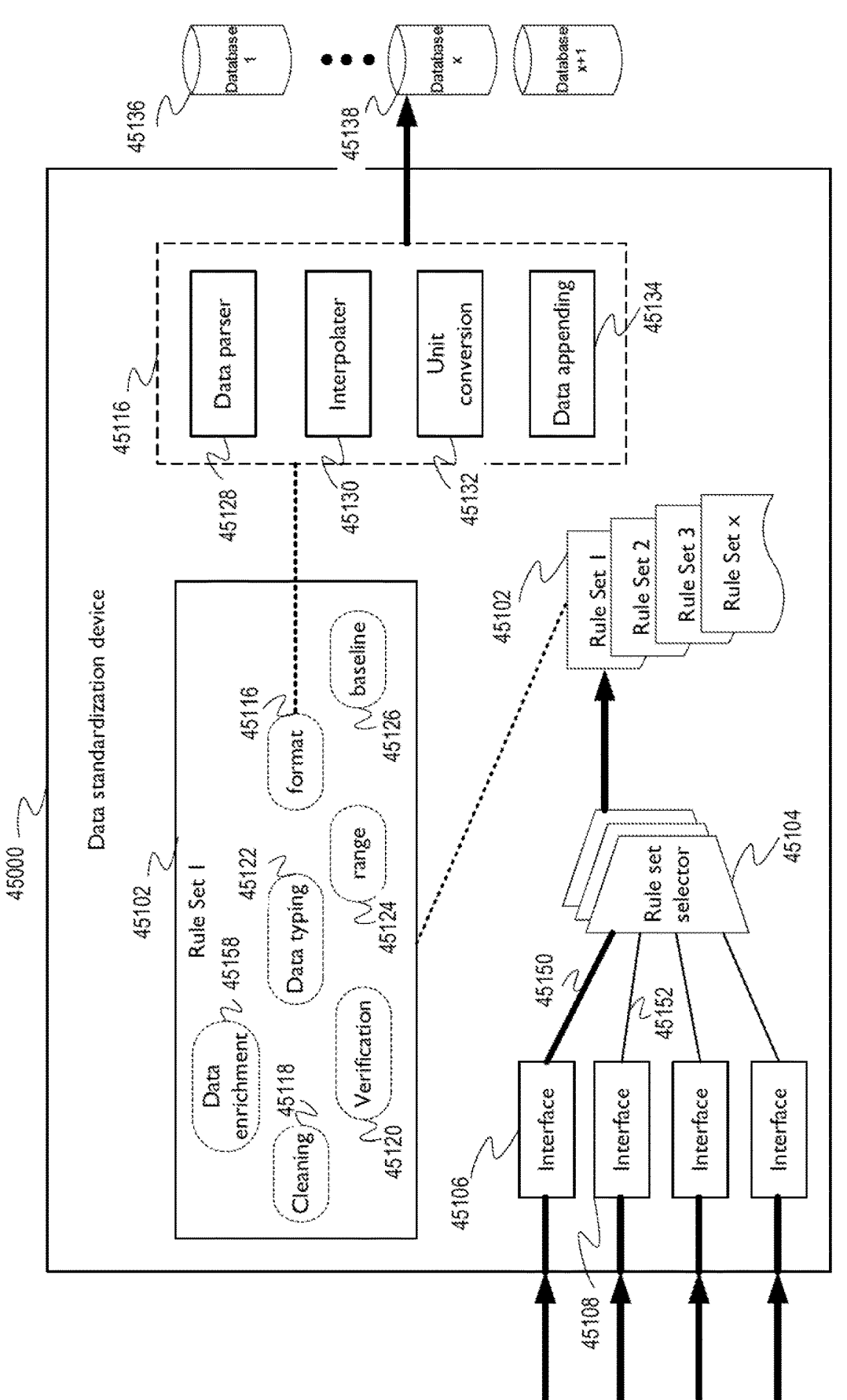
FIG. 10 shows an example data standardization device.

FIG. 10 shows an example data standardization device 450). The data standardization device 45000 may receive surgical data stream 45150 via surgical data interface 45106. The data standardization device 45000 may receive surgical data stream 45152 via surgical data interface 45108. An interface, for example, the surgical data interfaces 45106, 45108, and 44540-44546, may include a logical entity that interfaces with a certain type of surgical instrument. The interface may be configured to receive a data stream from a surgical instrument of that type. In an example, a certain type of surgical instruments may communicate with the surgical data system 45002 via a designated surgical data interface. The designated surgical data interface used to receive a surgical data stream may indicate the surgical instrument of the type, from which the surgical data stream is received. The interface, for example, one or more of the surgical data interfaces 45106, 45108, and 44540-44546, may be provided by an interface engine or an interface module, for example, the interface module 45030 in FIG. 9. The surgical data stream 45150 may indicate surgical infor-mation (e.g., a patient's symbolic and diabolic BP are in normal ranges).

The data standardization device 45000 may include a rule set selector 45104. The rule set selector 45104 may select a rule set for a data stream based on the interface that is configured to receive the data stream. In FIG. 10, the rule set selector 45104 may select rule set 1, referred as 45102, for example, among multiple rule sets including rule set 2 to rule set x, for the surgical data stream 45150. The rule set selector 45104 may identify the surgical data interface 45106. The rule set selector 45104 may select rule set 1 based on the identified surgical data interface 45106. The surgical data stream 45150 may be transformed into the standard format using rule set 1. The transformed surgical data stream may then be input to a database. The trans-formed surgical data stream may include the surgical infor-mation that is indicated by the surgical data stream 45150 (e.g., a patient's symbolic and diabolic BP are in normal ranges).

The selection of rule set 1 may be further based on the database into which the transformed surgical data stream is to be input. For example, database x, referred as 45138 may be input. Database x may be in a standard format. The data standardization device 45000 may be operatively coupled to one or more databases, for example, database 45136 and the database 45138. The database 45136 and the database 45138 may be in the same standard format or different standard formats. A standard format may be a format having one or more of a certain resolution, a certain sampling rate, a certain measurement type, a certain unit of measurement, a certain priority, or a certain type of data stream such as whether a data stream is a discrete data stream or a continuous data stream. The one or more databases may use different architectures. The different database architectures may include a hierarchical Database, a flat files database, an object database, or a relational database.

The selected rule set 1 may include, for example, data cleaning rules 45118, data verification rules 45120, rules for data typing 45122, rules 45124 for setting a data range, rules 45126 for setting a baseline, and data formatting rules 45116. The data formatting rules 45116 may include, for example, data parser rules 45128, interpolator rules 45130, unit conversion rules 45132, and data appending rules 45134. Depending on the surgical data stream which the selected rule set 1 is to be applied, rule set 1 may include some or all of the rules herein.

The selected rule set 1 may include the data cleaning rules 45118. Based on the data cleaning rules 45118, the data standardization device 45000 may detect and correct (or remove) corrupt or inaccurate records from a data stream, a record set, a table, or a database. The data standardization device 45000 may identify incomplete, inaccurate or irrelevant parts of the surgical data stream 45150. The data standardization device 45000 may replace, modify, or delete incomplete, inaccurate or irrelevant parts (e.g., dirty or coarse data) of the surgical data stream 45150. The data standardization device 45000 may determine a reference data set (e.g., similar but clean data sets). The data standardization device 45000 may determine a data cleaning target (e.g., what the data should appear like) based on the reference data set. The reference data set may be used for comparison and adaptation of the surgical data stream 45150. The data standardization device 45000 may determine how to clean the surgical data stream 45150 in consistency with the reference data set. The data standardization device 45000 may replace or supplement partial data sets (e.g., partial mating data sets) based on correlated records. The data standardization device 45000 may perform harmonization or normalization of data streams, for example, to convert varying data formats into a cohesive database.

The selected rule set 1 may include the data verification rules 45120. The data verification rules 45120 may be used to improve data integrity. The data verification rules 45120 may define which data sets or data streams a data set or a data stream is permitted to be related to. For example, a patient record or a procedure record may be permitted to link to products that are used or applied to the patient or to the procedure; the patient record or the procedure record may not be permitted to link to unrelated data such as OR equipment used.

The data verification rules 45120 may include checks for invalid data and correction for the invalid data, for example, based on a fixed schema or a predefined set of rules. Data verification rules may be used to control data integrity, produce database stability, improve database performance, improve data re-usability, improve database maintainability, improve data or transformation traceability. Data verification rules may include rules that improve one or more of entity integrity, referential integrity, domain integrity, customized parameters integrity.

The selected rule set 1 may include the data enrichment rules 45158. The data enrichment rules 45158 may include merging third-source data from related systems or merging semi-parity data from sources within an OR, OR equipment, or OR measurement systems. The data enrichment rules 45158 may be used to enhance data streams to make more informed decisions. Data enrichment rules may include data appending rules.

The selected rule set 1 may include the data formatting rules 45116. The data formatting rules 45116 may include the data parser rules 45128 for organization. To generate the transformed data stream, the data standardization device 45000 may parse a received data stream according to the organization of the database in a standard format. In FIG. 10, parsing the received data stream according to the organization of the database in the standard format may be performed according to the data parser rules 45128.

The data formatting rules 45116 may include the interpolator rules 45130. The interpolator rules 45130 may include adding and/or calculating intermediate average data points, for example, to create a complete even cadence of data points. For example, the surgical data stream 45150 may have a sampling rate that is lower than the sampling rate of the standard format. The data standardization device 45000 may determine intermediate average data points for the surgical data stream 45150 based on the data points of the surgical data stream 45150. The data standardization device 45000 may generate the transformed data stream by adding the intermediate average data points to the surgical data stream 45150. In FIG. 10, the determination of the intermediate average data points and the addition of the intermediate average data points may be performed according to the interpolator rules 45130.

The data formatting rules 45116 may include the unit conversion rules 45132. The unit conversion rules 45132 may include processing the units into common unit measures (e.g., inches to millimeters). In FIG. 10, processing the units into common unit measures may be performed according to the unit conversion rules 45132.

The data formatting rules 45116 may include the data appending rules 45134. The data appending rules 45134 may include adding tags to the data stream for one or more of integration, organization, searching, annotating, or highlighting. In FIG. 10, adding tags for integration may be performed according to the data appending rules 45134.

In an example, the data standardization device 45000 may receive patient sensor data, for example, in a patient sensor data stream. The data standardization device 45000 may select a rule set for the patient sensor data based on the surgical data interface configured to receive the patient sensor data from a wearable patient sensor system, and a relational data base to store the patient sensor data. The data standardization device 45000 may generate transformed patient sensor data based on the selected rule set such that the patient sensor data can be input into the relational data base.

The rule set selector 45104 may select a different rule set (e.g., rule set 2) for the surgical data stream 45152. For example, rule set 2 may include one or more of the data cleaning rules 45118, the data verification rules 45120, the rules for data typing 45122, the rules 45124 for setting a data range, the rules 45126 for setting a baseline, or the data formatting rules 45116. The data formatting rules of rule set 2 may include one or more of the data parser rules 45128, the interpolator rules 45130, the unit conversion rules 45132, and the data appending rules 45134.

The data standardization device 45000 may receive instrument operational data, for example, in an instrument operational data stream. The data standardization device 45000 may receive OR equipment data, for example, in an OR equipment data stream. The data standardization device 45000 may select a rule set for the instrument operational data and generate a transformed instrument operational data based on the selected rule set for the instrument operational data. The data standardization device 45000 may select a rule set for OR equipment data and generate transformed OR equipment data based on the selected rule set for the OR equipment data. The rule set selected for the patient sensor data, the rule set selected for the instrument operational data, and the rule set selected for the OR equipment data may differ. For example, the patient sensor data may need a more complex cleaning rule and a more extensive interpolation than the instrument operational data does, for example, due to irregular wearing habits of the patent that has the wearable patient sensor system. The selected rule set for the patient sensor data may include data cleaning rules that are more complex than, for example, a selected rule set for the instrument operational data. The selected rule set for the patient sensor data may include interpolation that is more extensive than, for example, the selected rule set for the instrument operational data.

By using different rule sets, the transformed patient sensor data, the transformed instrument operational data, and the transformed OR equipment data may be in a format that has common sampling, synchronization, and interactive common events linked together. The transformed patient sensor data, the transformed instrument operational data, and the transformed OR equipment data may be stored in one database. The database may Include a relational database. In some examples, the transformed patient sensor data, the transformed instrument operational data, and the transformed OR equipment data may be stored in different databases of the same or different standard formats.

Transforming a data stream into a standard format or standard formats using the selected rule set may include verifying the integrity of the patient sensor data, the instrument operational data, and the OR equipment data. For example, the data standardization device 45000 may select rule set 1 for the patient sensor data. Rule set 1 may include the data cleaning rules 45118. The data standardization device 45000 may determine invalid data and invalid associations based on the data cleaning rules 45118. Transforming the patient sensor data may include excluding the invalid data and the invalid associations from the transformed patient sensor data.

Transforming a data stream into a standard format or standard formats using the selected rule set may include enhancing one data stream using a related data stream. Transforming a data stream into a standard format or standard formats may enable annotation of other related data or enable attachment of other related data to provide a context (or syntax) for the other related data. For example, the instrument operational data and the OR equipment data may be associated with a same surgical event. The data standardization device 45000 may generate one or more annotations for the instrument operational data using the OR equipment data. The generated annotations may enable the transformation of the instrument operational data into a standard format.

A rule set may be used to maintain qualities of data streams. Transforming data streams using suitable rule sets may improve the consistency or capacity of decisions or improve transformations that can result from the data streams. The data standardization device 45000 may improve data qualities of the data streams before the data streams are inputted to the databases by monitoring the data streams, adjusting the data streams, and enhancing the data streams.

Figure 11:
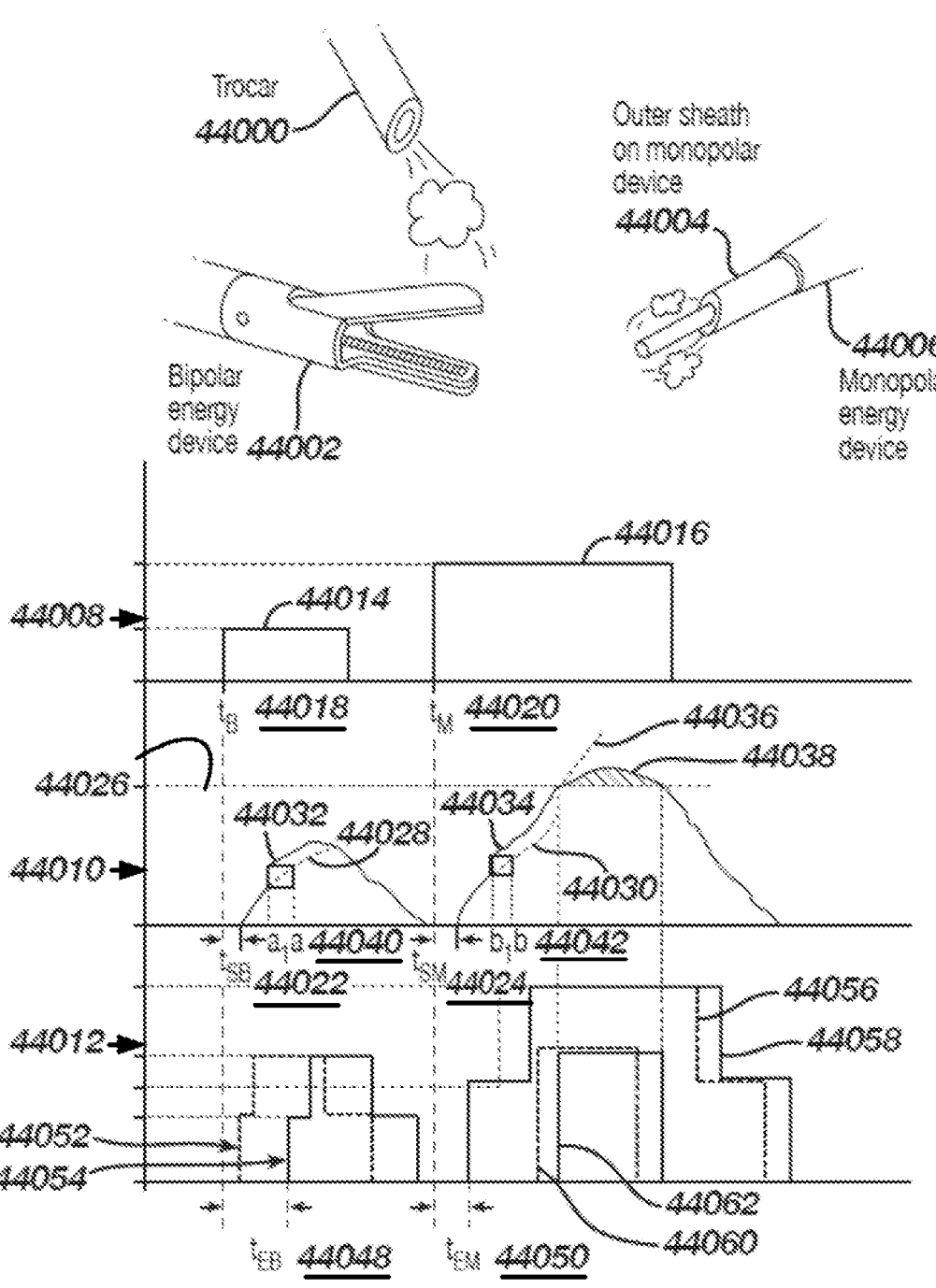
FIG. 11 shows an example data quality control.

FIG. 11 illustrates an example of data quality control. Data from an advanced energy generator may be paired with data from a monopolar generator with a tethered conventional smoke evacuator. A smoke evacuator (e.g., trocar 44000) may be used for a bipolar energy device 44002. A monopolar energy device 44006 may have an outer sheath 44004. The outer sheath 44004 may evacuate a smoke plume generated by the monopolar energy device 44006.

The graphs in FIG. 11 include a top portion 44008, a middle portion 44010, and a bottom portion 44012. The top portion 44008 shows energy activation types and amounts used by the bipolar energy device 44002 and the monopolar energy device 44006 over time. The top portion 44008 shows activation control signal. Graph 44014 shows the energy activation type and amount used by the bipolar energy device 44002 over time. Graph 44016 shows the energy activation type and amount used by the monopolar energy device 44006 over time. The middle portion 44010 shows the amounts of visual smoke plumes generated by the bipolar energy device 44002 and the monopolar energy device 44006 over time. The bottom portion 44012 shows the energy types and amounts used by the smoke evacuator for the bipolar energy device 44002 and by the smoke evacuator for the monopolar energy device 44006 over time.

The energy types and amounts used by the smoke evacuators may be plotted over time, shown in the bottom portion 44012. For example, an advanced energy generator (e.g., for the monopolar energy device 44006) may have an analog pigtail on the motor current of a smoke evacuator activation line and the power output and return path of the monopolar lines. A current monitoring device may measure the pigtail. Dotted energy graph 44052 shows the activation and energy amount used by the smoke evacuator (e.g., the trocar 44000) for the bipolar energy device 44002. Energy graph 44054 shows the activation and energy amount used for in situ smoke evacuation of the smoke plume generated by the bipolar energy device 44002. The energy graph 44054 shows a delay (e.g., 2 seconds). Dotted energy graph 44056 shows the activation and energy amount used by the smoke evacuator for the monopolar energy device 44006. Energy graph 44058 shows the activation and energy amount used for in situ smoke evacuation of the smoke plume generated by the monopolar energy device 44006. The energy graph 44058 shows a delay (e.g., 1 second). Dotted energy graph 44060 shows the activation and energy amount used by the smoke evacuator for the bipolar energy device 44002 when the smoke evacuator for the bipolar energy device 44002 is used with the smoke evacuator for the monopolar energy device 44006. Energy graph 44062 shows the activation and energy amount used for in situ smoke evacuation of the smoke plume generated by the bipolar energy device 44002 when the smoke evacuator for the bipolar energy device 44002 is used with the smoke evacuator for the monopolar energy device 44006.

The middle portion 44010 shows a resynchronized point 44032 of the amount of visual smoke plume generated by the bipolar energy device 44002 over time and lag 44028 of the amount of visual smoke plume generated by the bipolar energy device 44002 over time. The middle portion 44010 shows a resynchronized point 44034 of the amount of visual smoke plume generated by the monopolar energy device 44006 over time and lag 44030 of the amount of visual smoke plume generated by the monopolar energy device 44006 over time. (a, a1) is the estimated delay 44040. (b, b1) is the estimated delay 44042. During resynchronization of visual smoke plumes, a flag indicating a1 and b1 may be shown on a visual display. Dotted line 44036 shows the amount of visual smoke plume if only the smoke evacuator for the monopolar energy device 44006 is on. The shaded area 44038 corresponds to the amount of visual smoke plume if the smoke evacuator for the bipolar energy device 44002 and the smoke evacuator for the monopolar energy device 44006 are used together. A threshold 44026 (e.g., the maximum amount of visual smoke plume amount) may be set for visibility.

In an example, the synchronized graphs of the amount of visual smoke plume generated by the bipolar energy device 44002 over time, followed by the amount of visual smoke plume generated by the monopolar energy device 44006 over time, may show a visibility issue (e.g., caused by the smoke plume) from the scope, for example, following the activations of smoke evacuator for the monopolar energy device 44006 and the smoke evacuator for the bipolar energy device 44002. The amount of visual smoke plume generated by the monopolar energy device 44006 may be shown to be greater than the amount of visual smoke plume generated by the bipolar energy device 44002. The visual smoke plume generated by the monopolar energy device 44006 may be shown to last longer than the visual smoke plume generated by the bipolar energy device 44002. The visual smoke plume generated by the monopolar energy device 44006 may be shown to be delayed several seconds from the activation of the smoke evacuator for the monopolar energy device 44006. The visual smoke plume generated by the bipolar energy device 44002 may be shown to be delayed from the activation of the smoke evacuator for the bipolar energy device 44002.

The delays may be data artifacts because monitoring is lagging when the smoke evacuators are activated. The current monitoring device may have a low sampling rate. The current monitoring device may miss and overshoot the smoke evacuator activations and current draw levels. The delays may not be due to the application itself. Other data may be used to understand the delays, for example, using data enrichment techniques. Data cleaning techniques may be used to identify the delays and clean the data set related to the delays and/or overshooting.

The activation control signal 44008 may be used to clean the overshooting and clean the lagging data set (e.g., the lagging data set corresponding to the monitoring of the smoke evacuator motor control). The graph 44014 that shows the energy activation type and amount used by the bipolar energy device 44002 over time may be used to enrich data regarding the activation and energy amount used by the smoke evacuator for the bipolar energy device 44002, shown by the dotted energy graph 44052. The graph 44014 may be used to enrich data regarding in situ smoke evacuation of the smoke plume generated by the bipolar energy device 44002, shown in the energy graph 44054. The graph 44014 may be used to enrich data regarding the amount of visual smoke plume generated by the bipolar energy device 44002 over time and the lag 44028 of the amount of visual smoke plume generated by the bipolar energy device 44002 over time. The graph 44016 that shows the energy activation type and amount used by the monopolar energy device 44006 over time may be used to enrich the dotted energy graph 44056 that shows the activation and energy amount used by the smoke evacuator for the monopolar energy device 44006. The graph 44016 may be used to enrich the energy graph 44058 that shows in situ smoke evacuation of the smoke plume generated by the monopolar energy device 44006. The graph 44016 may be used to enrich data regarding the amount of visual smoke plume generated by the monopolar energy device 44006 over time and the lag 44030 of the amount of visual smoke plume generated by the monopolar energy device 44006 over time.

The activation timing, initiation points, deactivation points, and levels may be used to enrich the data to enhance the situational awareness of why, how and when the smoke evacuator motor control is synced or linked to the procedure and visibility data for the scope. Bipolar energy activation time point tB 44018 may be used to determine bipolar smoke plume delay tSB 44022. The bipolar energy activation time point tB 44018 may be used to determine bipolar smoke evacuation delay tEB 44048. Monopolar energy activation time point tM 44020 may be used to determine monopolar smoke plume delay tSM 44024. The monopolar energy activation time point tM 44020 may be used to determine monopolar smoke evacuation delay tEM 44050.

For example, amount of visual smoke plume generated by the monopolar energy device 44006 may be shown to be greater than the amount of visual smoke plume generated by the bipolar energy device 44002 because the monopolar energy level is higher. The visual smoke plume generated by the monopolar energy device 44006 may be shown to last longer than the visual smoke plume generated by the bipolar energy device 44002 because the on-duration for the monopolar energy is longer. The data enhancement of linking the mono-polar activation to the smoke evacuator activation corrects for the correlation and indicates that the magnitude of the motor activation may need to be changed, and the timing shifts (e.g., the delays) may be artifacts and need not be acted on.

Data streams that are in standard formats may be compared. For example, storing the transformed patient sensor data, the transformed instrument operational data, and the transformed OR equipment data in a standard format (e.g., in a cohesive database) or standard formats may enable a comparison from one surgical procedure to another surgical procedure. Surgical procedures may be compared when they share a common medical characteristic. For example, a surgical procedure for a patient may be compared with a surgical procedure for another patient, when these patients share a similar medical profile. A past surgical procedure of a patient may be compared with the current surgical procedure of the same patient. A same or similar procedures of different patients may be compared. The comparison may inform a surgeon on a likely outcome or risk of a surgical procedure.

The data standardization device 45000 may receive data streams from related equipment channeled through a primary equipment. The transformed data streams may include annotations of their relationship aspects. For example, two types of surgical instruments may both be channeled through a primary equipment such as a surgical hub. The data streams received from the two types of surgical instruments may be transformed into data streams of standard formats, and the transformed data streams may each include an annotation indicating the association with the primary equipment.

The data management module 45006 may include machine learning algorithms to adapt wearable device and/ or sensor collection, for example, to improve operability.

The surgical data system 45002 may include a data classification module 45004. The data classification module 45004 may classify a surgical data stream so that the data stream is handled in consistency with a healthcare data policy (e.g., Health Insurance Portability and Accountability Act (HIPPA)).

A device, for example, via the data classification module 45004 may determine a classification parameter for a surgical data stream. For example, the device may include the surgical data system 45002. The classification parameter may indicate a classification level for the surgical data stream. The classification parameter may indicate the classification levels for the surgical data stream if the classification parameter is multidimensional. The classification parameter may indicate a mapping between the informational content in the surgical data stream and a data handling scheme. The classification parameter may be indicated by a data tag included in the surgical data stream. The classification parameter may include a payload routing parameter and/or a payload handling parameter. The classification parameter may indicate the extent of sensitivity of the informational content in the surgical data stream. In an example, the classification level may be restricted, confidential, internal, public, or mid-classification levels, for example, a mid-classification level of the restricted classification level and the confidential classification level.

The classification parameter of the surgical data stream may be determined based on one or more of data source for the surgical data stream, a priority of the surgical data stream, a determination of whether the surgical data stream is requisite for another device's operation, a determination of whether the surgical data stream is requisite for a process, a determination of whether the surgical data stream is requisite for a task, or a determination of whether the surgical data stream is requisite for a decision making operation. A surgical data stream may be requisite when the surgical data stream is required to complete the task, process, or operation. A surgical data stream may be requisite when the surgical data stream is required to prepare the task, process, or operation. A surgical data stream may be requisite when the surgical data stream is required to follow up regarding the task, process, or operation.

The classification parameter of the surgical data stream may be determined based on the privacy of the surgical data stream. The types of data classifications, for example, the privacy-based data classifications, may include content-based classification, context-based classification, or user-based classification.

Content-based classification may include identifying sensitive information (e.g., patient specific data) by inspecting and interpreting files in the surgical data stream. The classification parameter may be determined based on whether the surgical data stream includes sensitive information. If the surgical data stream includes sensitive information, the classification parameter may be determined based on the amount of sensitive information in the surgical data stream and the nature of the sensitive information in the surgical data stream.

Context-based classification may include determining indicators (e.g., indirect indicators) of whether the surgical data stream includes sensitive information and indicators of the amount or nature of the sensitive information in the surgical data stream. The indicators of sensitive information may include one or more of an application, a location, or a creator among other variables. The classification parameter may be determined based on the indicators of sensitive information.

User-based classification may include a manual, end-user selection of surgical data or a document that includes the surgical data. The classification parameter may be determined based on user knowledge and/or discretion in creating editing, reviewing, or disseminating, for example, to flag sensitive information in the surgical data or in the document.

Two or more of content-based classification, context-based classification, and user-based classification may be combined to determine a classification parameter. Mid-classifications may be created where the surgical data stream is classified differently from a content-based-only classification, but not to the threshold of the context-based-only classification. A protected subgroup of a first group (e.g., a content-based-only classification) or a second group (e.g., context-based-only classification) may be created. The protected subgroup may share the characteristics of the first group or the second group, and may have one or more of additional limitations, protections, restrictions, or data handing requirements than the first group or the second group.

A classification parameter may be determined based on a priority of a surgical data stream. The determined classification parameter may indicate the priority of the surgical data stream. The determined classification parameter of the surgical data stream may increase in value based on importance of the surgical data stream to a specific user utilization. For example, the determined classification parameter of the surgical data stream may increase in value if part or all of the surgical data stream is used to attach or enhance another data stream that has higher priority. In an example, the priority of the surgical data stream may be the dominant factor (e.g., relative to the privacy of the surgical data stream) used to determine the classification parameter of the surgical data stream, for example, when the surgical data stream is processed relative to other surgical data streams in a system where resources are limited.

The determination of the classification parameter for a surgical data stream may be based on the content of the surgical data stream. The content of the surgical data stream may indicate other classification-related information than the privacy of the surgical data stream. The surgical data stream may be decoded, for example, when it is received by a device having a decoder. The device, for example, via the data classification module 45004, may infer the classification parameter of the surgical data stream based on the decoded surgical data stream. For example, the device may determine the nature of the content using the decoded surgical data stream. The device may infer the classification parameter based on the nature of the content. In an example, if the nature of the content indicates that the surgical data stream is useful for a mission-critical task, the device may infer that the classification parameter of the surgical data stream is at higher priority level than a surgical data stream that is not used for a mission-critical task. The device may determine the classification parameter of the surgical data stream in a look-up table. The look-up table may correspond one or more of a nature of content, a type of content, a context of content with a certain classification parameter.

The determination of the classification parameter for a surgical data stream may be based on contextual information of the surgical data stream. The contextual information may indicate the content of the surgical data stream, the type of the surgical data stream, the source of the surgical data system, the identification of the user who collected the surgical data stream. For example, for core body temperature data stream, the contextual information may indicate abnormal temperature, characteristic fluctuations, infection, menstrual cycle, climate, physical activity, and/or sleep. The device may determine a risk factor associated with the core body temperature data stream based on the contextual information. The device may determine a classification parameter for the core body temperature data stream according to the risk factor.

The determination of the classification parameter for a surgical data stream may be based on additional factors including one or more of a determination whether an error or a fault associated with the surgical data stream has occurred, an importance of the data to other interactions of other surgical data streams, whether the users (or manufactures) of the corresponding data source have highlighted data from the data source as having a special need, or whether a patient recovery related data has resulted in undesirable outcome(s).

A classification parameter for a surgical data stream may be multidimensional. The classification parameter may indicate one of more of a privacy of the surgical data stream, a priority of the surgical data stream, a content type of the surgical data stream, a context of the surgical data stream, a retention period associated with the surgical data stream, the usage of the surgical data stream, a user preference associated with the surgical data stream, or the like. For example, data received from incidental wearable devices may have a different classification parameter from that of data received from task specific devices. The data received from the task specific devices may require a different data handling scheme from that for the data received from the incidental wearable devices. The data received from the task specific devices may require data processing to be organized into the correct dataset and/or format. In an example, the classification parameter may be an index. The index may include multiple bits. A bit of the multiple bits may be given a binary value. In some examples, the index may be a combination of numbers or symbols of different numbering system, with each symbol or number indicating a level of a certain dimension (e.g., privacy, priority, etc.).

The device, for example, via the data classification module 45004, may determine the data classification parameter for a surgical data stream based on a surgical data interface used to receive the surgical data stream. The device may receive surgical data streams via the surgical data interfaces. The device may determine one or more the source, the priority, the privacy, or the like for a surgical data stream based on which surgical data interface is used to receive the surgical data stream. The device may identify the surgical data interface via which the surgical data stream is received and determine the data classification parameter for the surgical data stream based on the surgical data interface.

The surgical data interface may be designated for a type of surgical instrument. For example, endocutter devices and smoke evacuators are different types of surgical instruments. The device may receive endocutter data via an endocutter data interface and receive smoke evacuator data from a smoke evacuator data interface. The types of surgical instruments may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. In an example, each of the types of surgical instruments may have a designated surgical data interface.

A classification parameter of a surgical data stream may be determined or adjusted based on the interaction between the surgical data stream and another surgical data stream.

A surgical data stream may interact with a different surgical data steam according to a mode of interaction. The interaction of the surgical data streams may occur pre-surgery, or post-surgery, or may be intra-operative. A mode of interaction may include one or more of an enrichment of a surgical data stream using another surgical data stream, an aggregation of a surgical data stream and another surgical data stream, or a synthesis of a surgical data stream and another surgical data stream. An enrichment of a surgical data stream using another surgical data stream may include one or more of tagging one surgical data stream using another surgical data stream, generation an annotation of one surgical data stream using another surgical data stream, generating a notification regarding one surgical data stream using another surgical data stream, generating a threshold and/or baseline regarding one surgical data stream using another surgical data stream, generating contextual information regarding one surgical data stream using another surgical data stream, or the like.

A mode of interaction may be determined based on a surgical event. The surgical event may include one or more of pre-surgical, post-surgical, or intra-operative event. For example, if the surgical event is incision line leakage, data regarding staple and patient tissue thickness may be synthesized to generate insights that otherwise would not be shown using either data regarding staple or patient tissue thickness data.

A surgical event may include any identifiable unit of a surgery. The identifiable unit may have a beginning, a duration, and an end. The identifiable unit may be identified relative to a clock (e.g., at 5 mins into the surgery). The identifiable unit may be identified relative to a procedure (e.g., the initial incision). The identifiable unit may be identified relative to a patient's response (e.g., bleeding).

Figure 12:
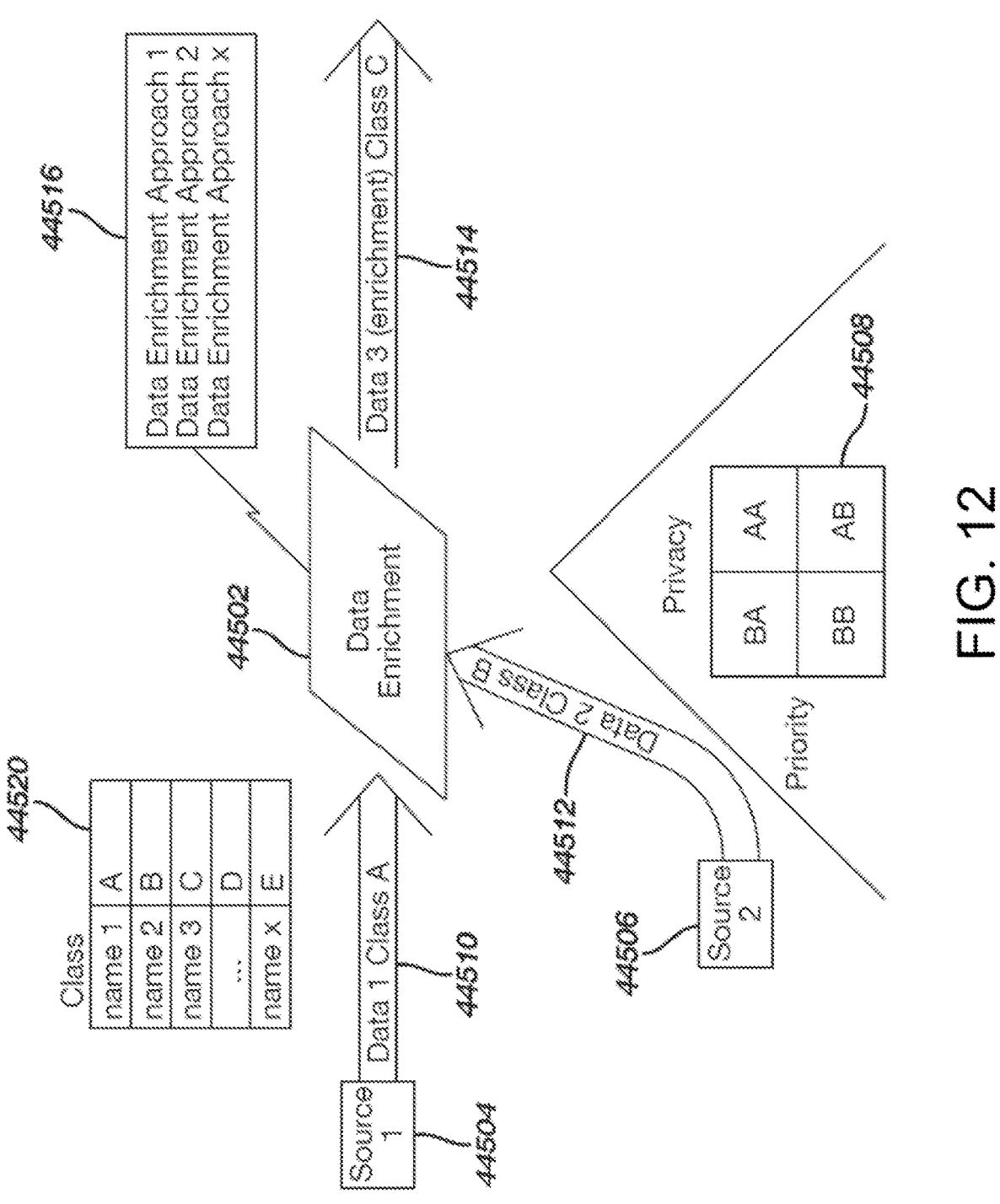
FIG. 12 shows an example data classification module.

FIG. 12 shows an example data classification module, for example, the data classification module 45004. The example data classification module may include a data enrichment function 44502. A classification for a surgical data stream may be adjusted based on an interaction of the surgical data stream with a differently classified surgical data stream. A device may receive a first surgical data stream 44510 from a data source 44504. For example, the device may include the surgical data system 45002. The device may receive a second surgical data stream 44512 from a data source 44506. The mode of interaction between the first surgical data stream 44510 and the second surgical data stream 44512 may be selected from multiple modes of interactions. The mode of interaction between the first surgical data stream 44510 and the second surgical data stream 44512 may be data enrichment. The data enrichment may be selected from multiple data enrichment approaches. For example, the data enrichment approaches may be in a list 44516 that includes multiple data enrichment rules 1, 2 . . . X. Surgical data stream 44514 may be generated by enriching the first surgical data stream 44510 using the second surgical data stream 44512.

The surgical data streams may be associated with different classification parameters. The first surgical data stream 44510 may be associated with a first classification parameter. The second surgical data stream 44512 may be associated with a second classification parameter. The first surgical data stream 44510 may be received in one or more data packets (e.g., a data packet including fields shown in FIG. 13). A data packet of the one or more data packets may include an element (e.g., a field) indicating the first classification parameter. In FIG. 12, the first classification parameter for the first surgical data stream 44510 is A, and the second classification parameter for the second surgical data stream 44512 is B. In some examples, the first surgical data stream 44510 may include a data tag indicating the first classification parameter.

A device may read the first classification parameter for the first surgical data stream 44510 or the second classification parameter for the second surgical data stream 44512 based on predetermined rules (e.g., a lookup table). In an example, table 44520 may be used for a one-dimensional classification parameter. The alphabet letters A-E may each indicate a different level of restrictions. The alphabet letters A-E may each indicate a different level of priorities. The alphabet letters A-E may each indicate a different level of privacies.

The first classification parameter for the first surgical data stream 44510 and the second classification parameter for the second surgical data stream 44512 may be multidimensional. The first classification parameter for the first surgical data stream 44510 and the second classification parameter for the second surgical data stream 44512 may have different number of dimensions, for example, depending on the nature of the respective surgical data stream. In an example, the first surgical data stream 44510 may include patient BP data, and the first classification parameter may have privacy dimension and priority dimension. The second surgical data stream 44512 may include monopolar energy data, and the second classification parameter may have a priority dimension but not a privacy dimension. When a classification parameter is multidimensional, a grid may be used to incorporate the multiple dimensions. In the example in FIG. 12, a grid 44508 may be used for a two-dimensional classification parameter. In the grid 44508, the two dimensions may be privacy and priority. "BA" may indicate low privacy and high priority, "AA" may indicate high privacy and high priority, "BB" may indicate low privacy and low priority, and "AB" may indicate high privacy and low priority. The first classification parameter for the first surgical data stream 44510 or the second classification parameter for the second surgical data stream 44512 may be any combination of numbers and symbols.

The classification parameter of the third surgical data stream 44514 may be determined based on the first classification parameter for the first surgical data stream 44510, the second classification parameter for the second surgical data stream 44512, and the data enrichment function 44502. The third surgical data stream 44514 may be generated using the data enrichment function 44502. The mode of interaction may be determined based on a surgical event. Based on the mode of interaction, the classification parameter of the third surgical data stream 44514 may be higher (e.g., AA) than both the first classification parameter (e.g., AB) for the first surgical data stream 44510 and the second classification parameter (BA) for the second surgical data stream 44512. Based on the mode of interaction, the classification parameter of the third surgical data stream 44514 may be the same (e.g., AB) as the first classification parameter (e.g., AB) for the first surgical data stream 44510 and higher than the second classification parameter (BB) for the second surgical data stream 44512. For example, if the mode of interaction is to aggregate patient BP data with endocutter data, the aggregated data stream may share the same privacy level and priority level with the patient BP data. Based on the mode of interaction, the classification parameter of the third surgical data stream 44514 may be lower (e.g., BB) than both the first classification parameter (e.g., AB) for the first surgical data stream 44510 and the second classification parameter (BA) for the second surgical data stream 44512. The classification parameter of the third surgical data stream

44514 may be determined using a surgical data classification engine tailored to solve multidimensional classification parameters.

The classification parameter of a surgical data stream may control how the surgical data stream is handled, for example, where and how the surgical data stream is stored, where and how the surgical data stream is transmitted, and how long the surgical data stream is stored locally. The communication path of the surgical data stream may be determined based on the classification parameter of the surgical data stream, for example, regarding how protected the channel used for the communication is and regarding the reliability and/or the stability of the channel used for the communication.

A device may determine a data handling scheme for a surgical data stream based on the determined classification parameter. For example, the device may include the surgical data system 45002. The data handling scheme may be consistent with the healthcare data policy (e.g., HIPPA). For example, the data handling scheme may include one or more rules that are consistent with HIPPA. The data handling scheme may specify one or more of a type of storage location for a surgical data stream, a configuration of a data storage location, a long-term treatment for a surgical data stream, a reliability level associated with a communication path used for a surgical data stream, a security level associated with the type of storage location and/or the communication path, a retention period for a surgical data stream, an environment (e.g., HIPPA protected) where a surgical data stream may be used, or the like. In an example, the classification parameter of the third surgical data stream 44514 may be AA indicating higher privacy level and higher priority level. The device may determine that the third surgical data stream 44514 may be stored locally so it can be used to prevent an urgent, life-threatening surgical event. The device may determine that the third surgical data stream 44514 may be stored in a HIPPA protected environment to ensure that patient's identifiable information is contained in the HIPPA protected environment. The device may determine that a communication path used to transmit the third surgical data stream 44514 has a reliability level and security level to the patient's identifiable information.

The transmission priority and the retention period of the surgical data stream on a local surgical hub system may be based on the classification parameter of the surgical data stream and additional variables. In an example, whether and how long the surgical data stream is to be stored locally may be based on the magnitude of the available free storage space of the appropriate type (e.g., having appropriate security level). As the free space of the appropriate type for data having a certain classification becomes less, the device may determine a transmission priority to a larger storage location or reclassification to a higher level of security, for example, to ensure required protection and adequate retention.

In an example, based on the classification parameter of a surgical data stream, the device may determine that a surgical data stream has the highest classification level among multiple surgical data streams that are to be transmitted. The device may select a communication path having the least amount of interruption among transmission resources that are available to be used for the transmission of the surgical data streams and send the surgical data stream using the selected communication path. In an example, data that is critical to procedure may be communicated through the secured or protected communication pathway, for example, to ensure that the data stream encounters the least interruption possible.

The device may communicate redundantly through the communication path having the least amount of interruption. For example, the device may, based on the determination that the third surgical data stream has the highest classification level among surgical data streams to be transmitted, repeat the sending of the third surgical data stream using the selected communication path. In an example, the device may duplicate the surgical data stream and communicate the original surgical data stream and the duplicate surgical data stream using two independent communication bus architecture or paths, for example, to ensure that the user is not deprived of receiving or displaying the surgical data stream. The device may separate the surgical data stream into less dense but useable data streams and communicate the separate data streams, for example, using multiple independent communication bus architecture or paths, for example, to ensure that the user is not deprived of receiving or displaying the surgical data stream. In some examples, being deprived of receiving or displaying the surgical data stream may result in a delay of a procedure or an interruption of a procedure or a conversation from lap to open.

In some examples, the classification of a related and coupled data stream may change the classification of another data stream such that the interaction of the data streams has the same priority, storage requirements, retention, or communication protections or the like. In FIG. 12, the classification parameter of the third surgical data stream 44514, the first classification parameter for the first surgical data stream 44510, and the second classification parameter for the second surgical data stream 44512 may be kept the same such that a same data handling scheme may be used for the third surgical data stream 44514, the first surgical data stream 44510, and the second surgical data stream 44512.

Classification of a surgical data stream may be used to determine how secure the communication link is utilized for the surgical data stream. In an example, classification of a surgical data stream may be used as the initial determination of what pathway of communication or processing is to be used. Visualization or primary control and/or response data streams that are required for key instrument operations or baseline instrument operations may be separated from the more advanced features or advanced processing, for example, to ensure at least the baseline operation is provided even if the processing or rebooting of the system is required. Examples that are suitable for use with the present disclosure are described in in U.S. Patent Application Publication No. US 2019-0201126 A1 (U.S. patent application Ser. No. 16/182,255), titled USAGE AND TECHNIQUE ANALYSIS OF SURGEON/STAFF PERFORMANCE AGAINST A BASELINE TO OPTIMIZE DEVICE UTILIZATION AND PERFORMANCE FOR BOTH CURRENT AND FUTURE PROCEDURES, filed Nov. 6, 2018, the disclosure of which is herein incorporated by reference in its entirety. In one or more of those examples, usage and technique analysis of the surgeon/staff performance against a baseline may be used to optimize device utilization and performance for both current and future procedures.

The surgical data system 45002 may include a data processing module 45024 for data stream processing. Data stream processing may provide one or more real-time analytics, streaming analytics, complex event processing, real-time streaming analytics, or event processing of surgical data streams. Examples that are suitable for use with the present disclosure are described in in U.S. Patent Application Publication No. US 2019-0206556 A1 (U.S. patent application Ser. No. 16/182,242), titled REAL-TIME ANALYSIS OF COMPREHENSIVE COST OF ALL INSTRUMENTATION USED IN SURGERY UTILIZING DATA FLUIDITY TO TRACK INSTRUMENTS THROUGH STOCKING AND IN-HOUSE PROCESSES, filed Nov. 6, 2018, the disclosure of which is herein incorporated by reference in its entirety. In one or more of those examples, real-time analysis of the comprehensive cost of instrumentation used in surgery may be performed, including the cost of reusable devices, their maintenance, cleaning, and re-sterilization by utilizing data fluidity to track instruments. Examples that are suitable for use with the present disclosure are described in in U.S. Patent Application Publication No. US 2019-0201102 A1 (U.S. patent application Ser. No. 16/182,290), titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION, filed Nov. 6, 2018, the disclosure of which is herein incorporated by reference in its entirety. In one or more of those examples, hub recommendations may be based on real-time analysis of procedure variables against a baseline highlighting differences from the optimal solution.

A device, for example, a surgical hub, may receive data streams from multiple data input feeds. For example, the device may include the surgical data system 45002. The multiple data input feeds may be interrelated. For example, multiple data input feeds may be used to generate a data stream that is more actionable or more capable of forming decisions from. The device may be configured with on-the-fly processing capabilities and real-time analytics. The device may, for example, using the real-time analytics, process data streams from one or more of the visualization, biomarker, instruments, and connected capital equipment. The device may distill the streams to a more context rich and decision able form. For example, the device may enhance a primary data stream using a secondary data stream. The primary data stream and the secondary data stream may be from separate sources. The enhanced primary data stream may be in a distilled form. In examples, the device may annotate, create meta data of, or provide context for the primary data stream using the secondary data stream.

The device may be configured to describe and/or summarize what has happened during a surgical event using real-time analytics. The surgical event may be on-going. The device may be configured to diagnose one or more reasons for what has happened during the surgical event using the real-time analytics. The device may be configured to predict what might happen based on the description of what has happened and the reasons for what has happened. The device may be configured to generate rules and recommendations for the surgical event based on the prediction what might happen. For example, the device may suggest an adjustment of an operation of an instrument. Examples that are suitable for use with the present disclosure are described in in U.S. Patent Application Publication No. US 2019-0201140 A1 (U.S. patent application Ser. No. 15/940,654), titled SURGICAL HUB SITUATIONAL AWARENESS, filed Mar. 29, 2018, the disclosure of which is herein incorporated by reference in its entirety. In one or more those examples, situational awareness of collected events may be provided. Examples that are suitable for use with the present disclosure are described in in U.S. Patent Application Publication No. US 2019-0201127 A1 (U.S. patent application Ser. No. 16/182,256), titled ADJUSTMENT OF A SURGICAL DEVICE FUNCTION BASED ON SITUATIONAL AWARENESS, filed Nov. 6, 2018, the disclosure of which is herein incorporated by reference in its entirety. In one or more those examples, a control for a hub or hub connected device may be adjusted based on a sensed situation or usage. Examples that are suitable for use with the present disclosure are described in in U.S. Patent Application Publication No. US 2019-0204201 A1 (U.S. patent application Ser. No. 16/182,246), titled ADJUSTMENTS BASED ON AIRBORNE PARTICLE PROPERTIES, filed Nov. 6, 2018, the disclosure of which is herein incorporated by reference in its entirety. In one or more those examples, airborne particulates and aerosols in insufflation gases within the abdomen may be detected and a device function may be altered based on the type, concentration, and flow of the particles. Examples that are suitable for use with the present disclosure are described in in U.S. Patent Application Publication No. US 2019-0206542 A1 (U.S. patent application Ser. No. 16/182,243), titled SURGICAL HUB AND MODULAR DEVICE RESPONSE ADJUSTMENT BASED ON SITUATIONAL AWARENESS, filed Nov. 6, 2018, the disclosure of which is herein incorporated by reference in its entirety. In one or more those examples, a hub response to a sensed parameter or event may be adjusted based on a second pre-existing sensed step, situation, or parameter.

Figure 13:
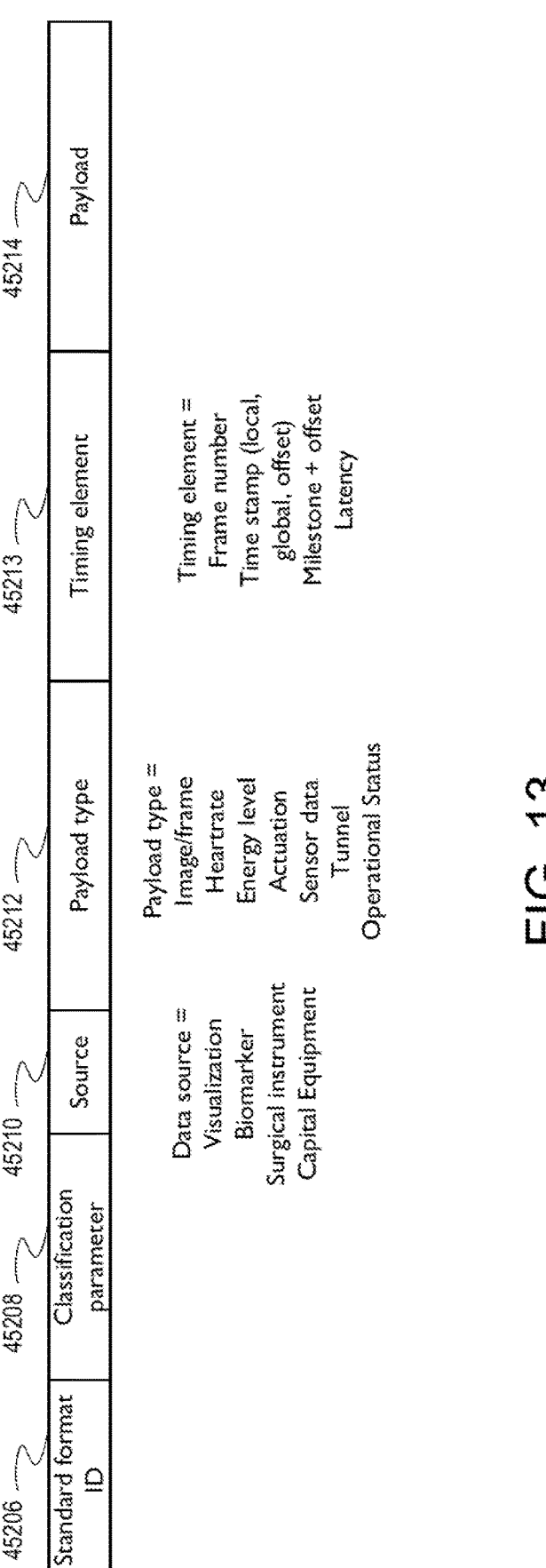
FIG. 13 shows an example data stream.

The device may receive one or more surgical data streams. For example, a surgical data stream of the one or more surgical data steams may include one or more indications. FIG. 13 shows an example data stream. The data stream may include a surgical data stream. As shown in FIG. 13, a surgical data stream may include indications of standard format ID 45206, classification parameter 45208, source 45210, payload type 45212, and timing element 45213. The surgical data stream may include the payload 45214.

The standard format ID 45206 may indicate whether the surgical data stream is in a standard format and which standard format the surgical data stream is in. For example, the surgical data stream may have been transformed based on rule set 1 in FIG. 10, and the standard format ID 45206 may indicate that the surgical data stream is in a standard format associated with the database x 45138.

The classification parameter 45208 may indicate the classification level(s) at which the surgical data stream is classified. For example, for the third surgical data stream 44514 in FIG. 12, the classification parameter 45208 may indicate that the third surgical data stream 44514 is at a high privacy level and a high priority level.

The source 45210 may indicate the data source from which the surgical data stream is received. The data source may include a surgical instrument, capital equipment, a biomarker sensing system, or a visualization device. The biomarker sensing system may include a wearable device. In FIG. 8, the data source may be a modular device 5102, a database 5122, a patient monitoring device 5124, an HCP monitoring device 35510, or an environment monitoring device 35512.

The payload type 45212 may indicate the type of the surgical data stream. For example, the type of the surgical data stream may include visualization data (e.g., an image or a frame), biomarker data (e.g., heart rate), energy level, actuation data, sensor data, tunnel, or operational status, and other type of data related to one or more surgical events.

The timing element 45213 may indicate a frame number, a time stamp (e.g., one or more of a local time, a local time offset, a global time, a global time offset, a milestone, a milestone offset, a latency, etc.). In an example, the timing element may indicate the time when the surgical data stream is collected. The timing element may indicate the time when the surgical data stream is sent. The timing element may indicate the time when the surgical data stream is used or to be used.

The indications including the standard format ID 45206, the classification parameter 45208, the source 45210, the payload type 45212, the timing element 45213 may be received via one or more data packets, for example, as elements or fields. The data packet may include the payload 45214.

The device may process the surgical data streams to generate a data stream that is more actionable or more capable of forming decisions from.

Figure 14:
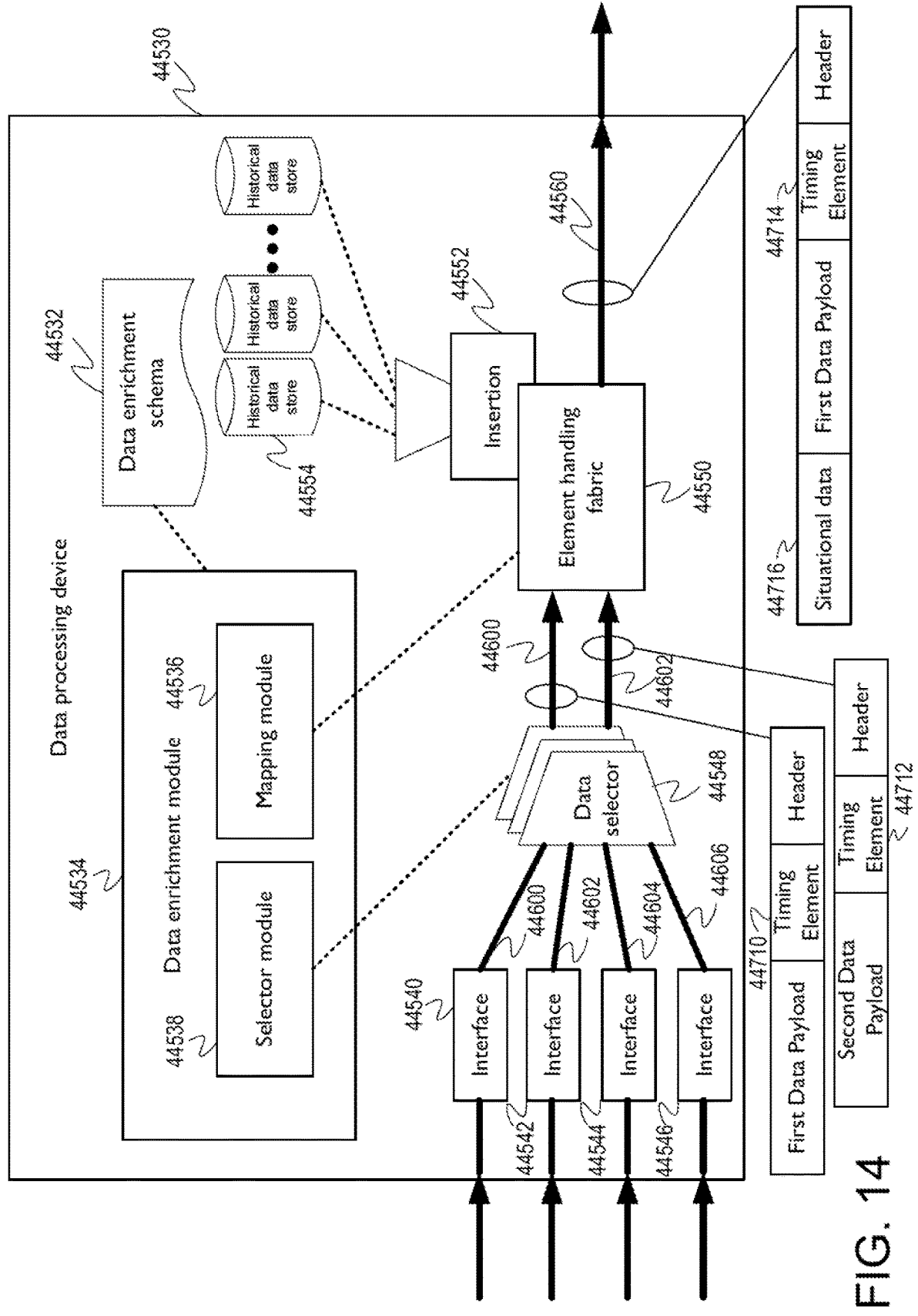
FIG. 14 shows an example data processing device.

FIG. 14 shows an example data processing device. The device in FIG. 14 may process multiple data streams. A device 44530 may include a surgical data system 45002 including the data processing module 45024. The device 44530 may be a data processing device. The device may receive surgical data streams 44600-44606 through the surgical data interfaces 44540-44546. The reception of the surgical data streams 44600-44606 may be during a surgical event (e.g., in real time while the surgical event is ongoing). The device may identify the surgical data interface from which a surgical data stream is received. In FIG. 13, the device 44530 may identify the surgical data interface 44454 via which the surgical data stream 44600 is received. The device 44530 may identify the surgical data interface 44542 via which surgical data stream 44602 is received.

Data selector 44548 may select the surgical data streams that are to be processed, based on a selector module 44538. For example, the data selector 44548 may select the surgical data stream 44600 and the surgical data stream 44602. The selection of the surgical data stream 44600 and the surgical data stream 44602 may be based on the selector module 44538. The selector module 44538 may be part of data enrichment module 44534. In an example, the data enrichment module 44534 may be part of the data processing module 45024 shown in FIG. 9. The data enrichment module 44534 may include the data enrichment function 44502. The selector module 44538 may be used to identify the surgical event and select the surgical data stream 44600 and the surgical data stream 44602 based on the surgical event. For example, the surgical data stream 44600 and the surgical data stream 44602 may include image data that needs to be inspected before an incision operation is to be performed on a patient. The selector module 44538 may identify the surgical data stream 44600 and the surgical data stream 44602 based on the incision operation. To identify the surgical data stream 44600 and the surgical data stream 44602, the selector module 44538 may identify the incision operation. The selector module 44538 may determine that the image data needs to be inspected for the incision operation. The selector module 44538 may identify the image data. The selector module 44538 may determine that surgical data stream 44600 and the surgical data stream 44602 include the image data based on the surgical data interface 44540 via which the surgical data stream 44600 is received and the surgical data interface 44542 via which the surgical data stream 44602 is received. The selector module 44538 may be used to select the surgical data stream 44600 and the surgical data stream 44602 based on the determination that the surgical data stream 44600 and the surgical data stream 44602 include the image data.

The device 44530 may include an element handing fabric 44550. The element handing fabric 44550 may include a mapping module 44536. The mapping module 44536 may be part of the data enrichment module 44534. The mapping module 44536 may be used to determine that a surgical data stream is associated with another surgical data stream. The mapping module 44536 may identify the type of association of a surgical data stream with another surgical data stream. The mapping module 44536 may select a mode of interaction between a surgical data stream and another surgical data stream based on the type of association of the surgical data stream and the other surgical data stream. For example, the mode of interaction may include data enrichment. The data enrichment may use data enrichment schema 44532. The mode of interaction may include other modes of interactions. If the mode of interaction is one other than data enrichment, other types of schemas may be used to support that mode of interaction.

The data enrichment schema 44532 may indicate a characteristic of a primary surgical data stream, a characteristic of a secondary surgical data stream, which part of the primary surgical data stream is to be enriched, in what manner the part of the primary surgical data stream is to be enriched, which part of the secondary surgical data stream is to be used to enrich the primary surgical data stream, in what manner the secondary surgical data stream is to be used to enrich the primary surgical data stream, and other rules or provisions regarding the data enrichment.

The mapping module 44536 may be used to determine that the surgical data stream 44600) is the primary surgical data stream, for example, based on the surgical data interface 44540 via which the surgical data stream 44600 is received. The mapping module 44536 may be used to determine that the surgical data stream 44602 is the secondary surgical data stream, for example, based on the surgical data interface 44542 via which the surgical data stream 44602 is received. That the surgical data stream 44600 is received via the surgical data interface 44540 may be indicative of the surgical data stream 44600 having the characteristic of the primary data stream. That the surgical data stream 44602 is received via the surgical data interface 44542 may be indicative of the surgical data stream 44602 having the characteristic of the secondary data stream. The device 44530 may determine, for example, using the mapping module 44536 and/or the data enrichment schema 44532, that the secondary surgical data stream is to be used to provide surgical information for the primary surgical data stream. For example, the data enrichment schema 44532 may provide that the secondary surgical data stream may be used to provide situational data for the primary surgical data stream.

The selector module 44538 may collaborate with the mapping module 44536 to select surgical data streams. For example, the selector module 44538 may select the surgical data streams based on the type of association of a surgical data stream with another surgical data stream, as identified by the mapping module 44536.

The primary data stream and the secondary data stream may be handled differently. The secondary surgical data stream may not be stored in its entirety, for example, after the secondary surgical data stream has been processed to provide the situational data for the primary surgical data stream. In some examples, secondary surgical data stream may not be stored locally or may be removed from storage locations after the secondary surgical data stream has been processed to provide the situational data. The device 44530 may display the primary surgical data stream and the situational data, for example, without displaying the secondary surgical data stream.

The element handing fabric 44550 may generate situational data for the primary surgical data stream based on the secondary surgical data stream and/or the data enrichment schema 44532. The situational data may include surgical information that may be used to make a medical decision about the surgical event. The medical decision may be made based on the primary surgical data stream and the surgical data for the primary surgical data stream. The situational data may indicate a medical decision-making factor of the surgical event. The medical decision-making factor may indicate the surgical information. The medical decision-making factor may indicate an interpretation of one or more of the following: a surgical procedure (e.g., a procedure step or a procedure plan), imaging data (e.g., a pre-operative scan, an intra-operative scan, a primary scope, or a flexible endoscope), patient data (e.g., co-morbidities, physiologic monitors, or anesthesia), or instrument measures (e.g., tissue impendence, seal strength, or cartridge type). The medical decision-making factor may inform a user of the primary data stream about complications or risks associated with the surgical event. One or more the following examples may illustrate the primary surgical data stream and the situational data for the primary surgical data stream: when the primary data stream includes core body temperature data, the situational data may include abnormal temperature, characteristic fluctuations, infection, menstrual cycle, climate, physical activity, and/or sleep; when the primary data stream includes behavior and psychology-related data, including sleep, circadian rhythm, physical activity, and/or mental aspects for analysis, the situational data may include behavior and psychology scores may include scores for social interaction, diet, sleep, activity, and/or psychological status; when the primary data stream is activity-related data, the situational data may include activity duration, activity intensity, activity type, activity pattern, recovery time, mental health, physical recovery, immune function, and/or inflammatory function; when the primary data stream includes lymphatic system-related data, the situational data may include fibrosis, inflammation, and/or infection; when the primary data stream includes blood vessel-related data, the situational data may include infection, anastomotic leak, septic shock and/or hypovolemic shock.

The element handing fabric 44550 may output surgical data steam 44560 during the surgical event. The surgical data stream 44560 may include the primary surgical data stream and the situational data.

One or more of the reception of the surgical data streams 44600-44606, the selections of the surgical data streams 44600 and 44602, the identification of the surgical data interfaces 44540 and 44542, the determination of the primary surgical data stream and the secondary surgical data stream, or the generation of the situational data may occur in real time (e.g., processed using real-time analytics). A predetermined value may be used to facilitate real-time processing. In FIG. 14, the surgical data stream 44600 may include a timing element 44710. The timing element 44710 may indicate a time when the surgical data stream 44600 is collected. The surgical data stream 44602 may include a timing element 44712. The timing element 44712 may indicate a time when the surgical data stream 44602 is collected.

The generation of the situation data for the primary surgical data stream may occur at a time that is the same as or similar to the time when the surgical data stream 44600 is collected, or the same as or similar to the time when the surgical data stream 44602 is collected. The primary surgical data stream and the situational data may be sent at a time that is the same as or similar to the time when the surgical data stream 44600 is collected, or the same as or similar to the time when the surgical data stream 44602 is collected. The similarity in time may be determined based on a predetermined value (e.g., a predetermined time duration value such as a threshold). In FIG. 14, the surgical data stream 44560 may include a timing element 44714. The timing element 44714 may indicate a time when the surgical data stream 44560 and situational data 44716 are sent. The timing element 44714 may indicate a time when the situational data 44716 is generated. The difference between the timing element 44714 and the timing element 44710 may be lower than a predetermined value. The difference between the timing element 44714 and the timing element 44712 may be lower than the predetermined value. The difference between the timing element 44714 and the timing element 44710, which is lower than the predetermined value, may indicate that the surgical data stream 44560 is sent in real time as the surgical data stream 4460') is collected. The difference between the timing element 44714 and the timing element 44712, which is lower than the predetermined value, may indicate that the situational data 44716 is generated in real time as the surgical data stream 44602 is collected.

A risk indicator may be generated based on the situational data and the primary surgical data stream. The risk indicator may be sent to a display device, for example, during the surgical event. The risk indicator may include one or more of actionable triggers, thresholds, or insights.

Risk assessment of patient biomarkers may be performed to determine the suitability of the surgical procedure and/or likely outcomes. A device, e.g., a surgical hub, may include an interactive hub algorithm. The device may include the surgical data system 45002. The device may analyze risk probabilities using the interactive hub algorithm. For example, the device may analyze the primary data stream and the situational data to determine risk probabilities. The device may notify users about the risk probabilities. The device may adjust coupled instrument parameters based on the risk probabilities. In an example, the device may generate control instructions based on the primary data stream and the situational data. The control instructions may be sent to adjust an operation of a surgical instrument operatively coupled to the device. The interactive hub algorithm may determine a probability of a certain surgical outcome and/or generate a notification about the probability of the surgical outcome. The notification may be sent to a wearable system. Examples that are suitable for use with the present disclosure are described in in U.S. Patent Application Publication No. US 2019-0201125 A1 (U.S. patent application Ser. No. 16/182,251), titled INTERACTIVE SURGICAL SYSTEM, filed Nov. 6, 2018, the disclosure of which is herein incorporated by reference in its entirety. In one or more those examples, interactive feedback to the user may enable adjustment of a device or display based on presence of an actionable aspect of the task at hand for the user. Examples that are suitable for use with the present disclosure are described in in U.S. Patent Application Publication No. US 2019-0201124 A1 (U.S. patent application Ser. No. 16/182, 239), titled ADJUSTMENT OF DEVICE CONTROL PROGRAMS BASED ON STRATIFIED CONTEXTUAL DATA IN ADDITION TO THE DATA, filed Nov. 6, 2018, the disclosure of which is herein incorporated by reference in its entirety. In one or more those examples, device control programs may be adjusted based on stratified contextual data in addition to the data. The contextual data may represent the circumstances around data collected or related patient, procedure, surgeon, or facility information. Examples that are suitable for use with the present disclosure are described in in U.S. Patent Application Publication No. US 2019-0201123 A1 (U.S. patent application Ser. No. 16/182,233), titled SURGICAL SYSTEMS WITH AUTONOMOUSLY ADJUSTABLE CONTROL PROGRAMS, filed Nov. 6, 2018, the disclosure of which is herein incorporated by reference in its entirety. In one or more those examples, hub or instrument control programs may be modified based on machine learning that analyzes performance and outcomes recorded over more than one procedure.

The device may include algorithms for monitoring wearable streaming data from patient(s) or OR staff. The wearable streaming data may indicate measurements taken on the patient(s) or the OR staff. The measurements may include biomarker measurements. The measurements may be associated with a procedure situation. The device may compare the measurements with biomarkers indicating the risk probabilities of a procedure situation. The device may identify a procedure step that may result in a complication or issue. The device may generate a notification of intervention. If the probability of that monitored biomarker(s) at that step is above the predefined likelihood of complication, a notification(s) may be sent to the OR staff about the possible risk or complication, or a signal may be sent to a surgical instrument operatively coupled with the device or an imaging system to request a change in the control algorithm of the surgical instrument or the imaging system.

In an example, a patient undergoes a colorectal resection of the descending sigmoid colon. The resection may require a considerable amount of colon removal and mobilization of the colon. As the surgeon mobilizes the colon, an insufficient amount of the colon may be mobilized, resulting in a high tissue tension on the remnant portion. Once the surgeon reconnects the anastomosis and is preparing to close the patient, a sensor on the patient that monitors the local pH of the surgical area exceeds a threshold. That biomarker exceeding that threshold indicates a risk probability. That biomarker exceeding that threshold indicates or implies a reasonable probability of an insufficient blood flow to the region, which may result in a $CO_2$ buildup that results in a local pH change. The surgeon may be notified (e.g., via a notification) of the possible issue or the risk probability. A request may be sent to the attached multi-spectral imaging to examine that region using a Doppler transform of the laser light through the green-red spectrums to visualize blood flow in the connective tissue and the bowel of that region. The concentrated focus area of that region along with the laser Doppler Flowmetry may show an occlusion of the blood flow, which the surgeon tracks back to the elevated macro tissue tension. The surgeon corrects the issue. If left uncorrected, the issue could have resulted in tissue necrosis and a leak forming from the colon to abdomen, which could have resulted in a hospital acquired infection or even require a re-admittance and a re-operation.

Data streams may be processed continuously to change operational tool controls and/or to change scheduling. The change of the operational tool controls and scheduling may improve outcomes.

One or more data streams (e.g., surgical data streams generated by patient sensing systems) may be processed with historical data regarding outcomes of previous surgeries. A more actionable decision point may be generated by coupling the one or more data streams with the historical data regarding the outcomes of the previous surgeries. The historical data regarding the outcomes of the previous surgeries may indicate a likelihood of a surgery operation including a surgery timing to result in a certain outcome (e.g., a desired outcome)

The element handing fabric 44550 may generate situational data for the primary surgical data stream based on historical data. An insertion operation 44552 may be performed to add historical data from a historical data store, for example, historical data store 44554. The historical data may be from a historical surgical event. The historical surgical event and the current surgical event may have a common characteristic. The common characteristic may be that the historical surgical event and the current surgical event are both for a same patient or patients with same or similar medical profiles. The common characteristic may be that the historical surgical event and the current surgical event are both for a same or similar type of surgical procedure. The common characteristic may be that the historical surgical event and the current surgical event both use a same type of surgical instrument or the same surgical instrument. The common characteristic may be that the historical surgical event and the current surgical event both use a same type of surgical equipment or same equipment. For example, if a piece of equipment has a pre-surgery history of interference or irregular sensing issues in a predictable manner, during surgery an event that could be misinterpreted as an issue may be noted as a probable equipment issue and adjusted based on pre-history data sets for that piece of equipment.

In an example, biomarker data streams may be processed over time based on comparisons with previous data sets, for example, to determine when a surgical procedure may be best run, staffed, or scheduled.

Biomarker data streams (e.g., patient biomarker data streams) and a surgical procedure (e.g., the current surgical procedure) may be processed based on historical data (e.g., historical data from the local facility's database or global network database). The local facility's database or global network database may include data collected from previous surgeries. The data collected from previous surgeries may include outcomes of surgical events that occurred during previous surgeries. An indication or notification of one or more predicted issues may be generated by processing the biomarker data streams and the historical data. The indication or notification may be sent to the surgical team. The indication or notification may indicate one or more predicted complications. The processing of the biomarker data streams and the historical data may be based on one or more patients with similar biomarkers of the same or similar procedure. The indication or notification may better prepare the surgical team if the predicted issue(s) or predicted complication(s) occurs. The staff may be prepared for the risk(s) associated with the current patient or the current surgical procedure. A more informed staff may be prepared to react rather than being caught off guard if the predicted issue(s) or predicted complication(s) occurs. Examples that are suitable for use with the present disclosure are described in in U.S. Patent Application Publication No. US 2019-0201115 A1 (U.S. patent application Ser. No. 15/940,668), tided AGGREGA-TION AND REPORTING OF SURGICAL HUB DATA, filed Mar. 29, 2018, the disclosure of which is herein incorporated by reference in its entirety. In one or more those examples, surgical tool utilization and OR event(s) may be correlated with the global outcomes and efficiencies.

Biomarker data of a patient may be compared against the patient's historical biomarker data. Biomarker data that is outside of the normal range may be identified based on the comparison. A risk of certain biomarker data and the impact of the biomarker data on a surgical procedure and/or an outcome may be determined based on the comparison.

Biomarker data of a patient may be evaluated based on database that includes the patient's historical biomarker data and the historical biomarker data of the direct relatives and/or family. Hereditary deficiencies or risk may be identified based on the comparison. Suitability of a surgical procedure or outcome may be identified based on the comparison.

In an example, a certain patient has a consistent BP reading of 128/84+/−2 points in either direction. The BP reading of 128/84+/−2 points may be considered elevated (e.g., a high BP) based on the American Heart Association guidelines. A primary care physician first places this patient on BP medicine, with quarterly check-ups. When such treatment regimen does not change this patient's BP reading, the medical history of the patient is examined. The medical history shows that the patient's BP has been 128/84+/−2 since childhood. Blood work may be done for the patient after the original treatment regimen is discontinued, which concludes all markers are normal. It is further concluded that, based on the patient's body type and genetics, the patient's normal BP is higher than the standard. Utilizing the patient's historical data may provide more insights and help develop a more unique solution with surgical procedures and outcomes. The patient's historical data is tailored to the patient. The treatment regimen may be updated based on individual patients' normal ranges and not based on a standardized approach.

Instrument event data streams may be processed with patient biomarker data to produce a data output feed that may be used to adapt the instrument control program. Biomarker feedback may be used to adjust the operational parameters of the instrument, for example, by allowing the instrument event data streams and the patient biomarker data to be coupled to identify coupled relationships in their operation and outcomes.

A surgical procedure may be compared with another surgical procedure. The outcome of a surgical procedure may be used to predict the outcome of another surgical procedure based on a comparison of the surgical procedure. The current surgical procedure (e.g., the type of procedure) may be compared with previous surgical procedures. The outcomes of the previous surgical procedures may be used to predict the outcome of the current surgical procedure. Patient biomarker data during a previous surgical procedure and/or pre-operative testing of the patient who underwent the previous surgical procedure may be stored in a local facility database or global network database. In an example, the current surgical procedure type may be compared with the previous surgical procedure type. If the current surgical procedure type is same as or similar to the previous surgical procedure type, the current patient biomarker data may be compared with the previous patent biomarker data. If the current patient biomarker data is the same as or similar to the previous patent biomarker data, a probable outcome of the current surgical procedure may be determined based on the outcomes of the previous surgical and/or based on determined risks. The comparison of the current surgical procedure with the previous surgical procedures (e.g., past data sets) may facilitate an identification of a trigger that have resulted in adverse events in the previous surgical procedure, an identification of a potential risk to the current patient, an identification of a probability of an increased time for a certain procedure, or an identification of a probability of a requirement for additional staff. The current surgical procedure, for example, if it is being considered in a surgical plan, may be delayed or rescheduled until the patent's biomarker data show results in an acceptable range and/or until a pharmaceutical intervention controls biomarkers identifiers into a safe zone prior to the procedure, or until the staffing or products that need to mitigate a predicted issue are acquired. The outcomes and cost-effectiveness of care for patients undergoing surgery may be improved.

Pre-surgery biomarker data, post-surgery biomarker data, and intra-operative biomarker data (e.g., regarding surgical occurrences) may be used to adjust post-surgery monitoring.

A device, for example, a surgical hub, may identify and set post-surgery critical thresholds (e.g., post-surgery critical thresholds for wearable devices). The device may include the surgical data system 45002.

The device may identify based on the type of procedure and patient's information, pre-operative and intra-operative biomarkers, pre-operative and intra-operative test results to determine factors that should be tracked post-operation and/or determine the thresholds that should be applied. The device may communicate and/or set other systems and/or devices to continue monitoring post-surgery. For example, the thresholds may include one of more of BP thresholds, activity thresholds, step count thresholds, thresholds related to breathing, thresholds related to sleeping, and thresholds related to dehydration.

Figure 15A:
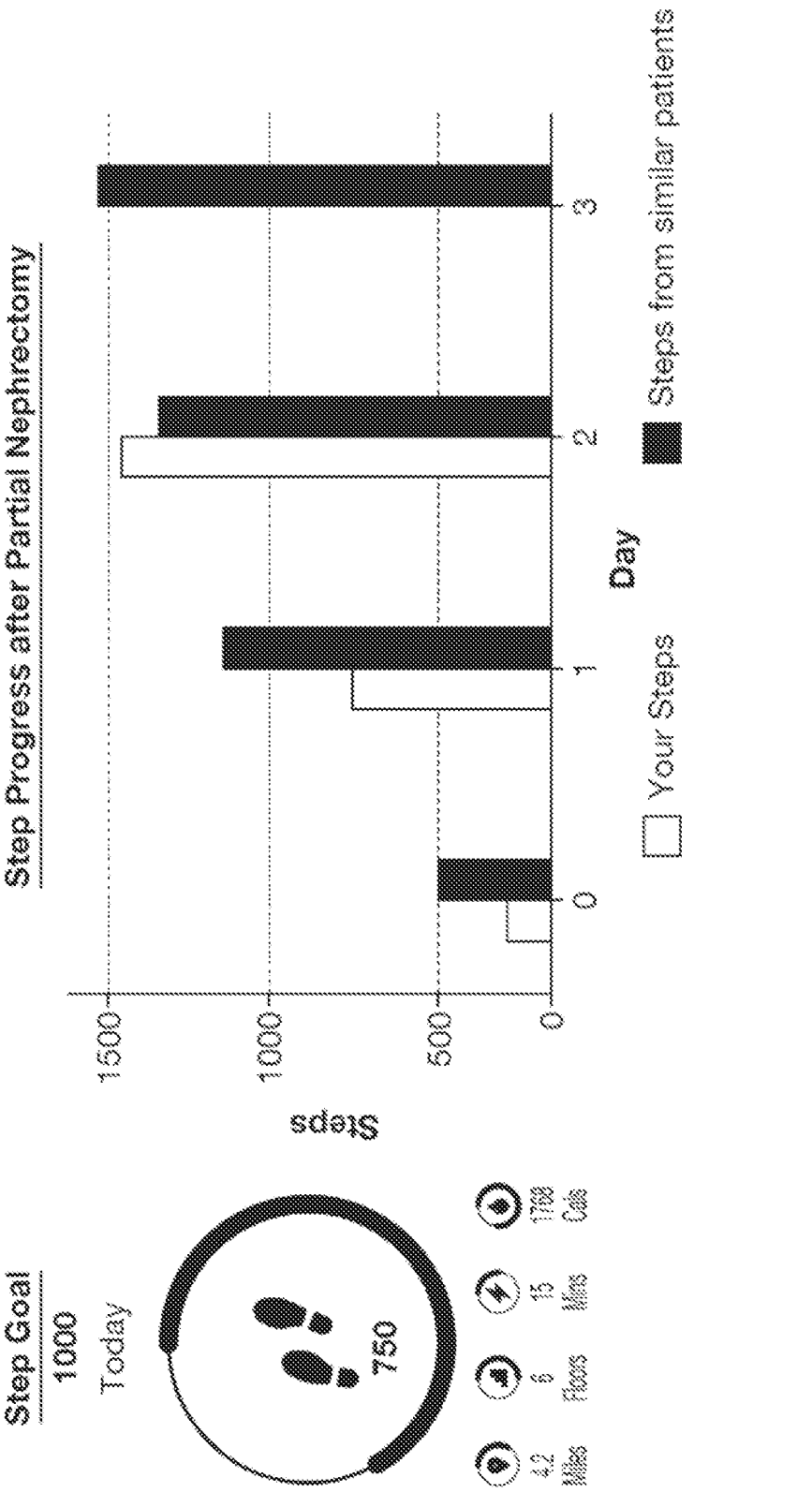
FIG. 15A shows a patient's step progress after partial nephrectomy, compared with similar patients.
Figure 15B:
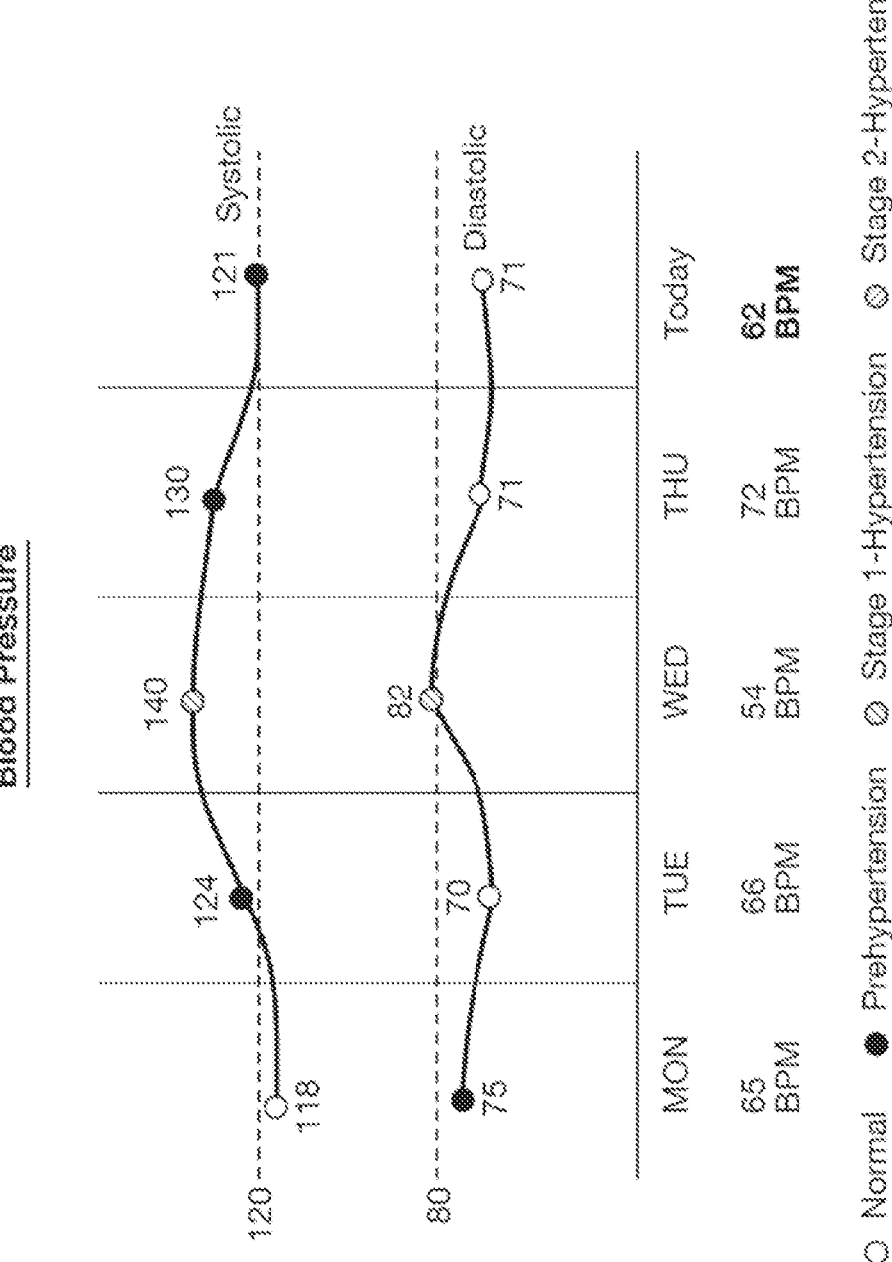
FIG. 15B shows a patient's daily systolic BP and diastolic BP over a week and assessments of a normal BP, prehypertension BP, and stage 1 hypertension BP.

The device may communicate to post-surgery room monitor(s) to provide recommended activities to the patient. The device may provide the patient's goals to achieve or compare the patient's current activity levels to the activity levels of other patients that have undergone similar procedures and share similar patient data. The device may advise the patient how the patient is doing. The comparison may motivate the patient to achieve the goals such that the patient may improve the patient's recovery and reduce the hospital stay. FIG. 15A shows a patient's step progress after partial nephrectomy, compared with similar patients. FIG. 15B shows a patient's daily systolic BP and diastolic BP over a week and assessments of a normal BP, prehypertension BP, and stage 1 hypertension BP. The device may communicate and set the required items and thresholds on the patient's wearable devices, for example, to provide notifications to the patients and/or heath care providers.

The device may communicate to a local facility data storage or a cloud storage in which other monitoring equipment (e.g., all other monitoring equipment) may be tagged to the patient and may automatically pull the data sent from the device to the local facility data storage or the cloud storage as the monitored values or thresholds for the patient. Other monitoring equipment may be adapted to the patient based on the identity of the patient that is connected to the other monitoring equipment and may automatically set which items are monitored and thresholds for that patient. Errors caused by incorrect setting by a user may be prevented. The patient may not need to be mounted to various equipment as the patient moves through the facility. When the patient moves to a room where the equipment needed for additional testing, checks, or follow-ups is located, there is no need to reset the needed equipment. Post-operative monitoring data streams may be collected and/or processed regularly, for example, to further adjust and refine the post-surgery thresholds and targets.

The device may set and control the patient's wearables, for example, enabling an early discharge and an increased willingness of patients to be discharged early. Wearable devices may change the landscape of preoperative optimization as well as postoperative monitoring of high-risk patients or patients undergoing high-risk surgeries. For example, cystectomy has 90-day readmission rates as high as 40%. The ability to identify patients at risk for or in the early stages of serious postoperative complications, such as sepsis, may improve outcomes and save millions in health care dollars. Reliable at-home monitoring may potentially enable an early discharge and an increased willingness of patients to be discharged early. A wearable device may include a heart rate monitoring feature. Heart rate monitoring may be clinically useful. Heart rate may act as a surrogate for a number of common postoperative complications such as dehydration or infection. A wearable device designed for patient monitoring may focus on heart rate monitoring capabilities. The wearable device may be configured to identify cardiac arrhythmias in addition to a patient's respiratory rate, skin temperature, steps, and fall detection.

Batch processing may be used to process data streams. Data may build up and be processed in a batch as data streams. The amount of data may be voluminous and make it difficult to store the data in an unprocessed or uncomplied state. A batch processing system may split data into time intervals. Data streams may be processed to reduce the data intro smaller more storable or communicable paired data or streams. In some examples, events that start during a time interval but end during another time interval may not be analyzed. Continuous data streams may be queried to detect conditions.

The data processing module 45024 may include a data integration module (e.g., data input/export) and/or a data collection module. The data collection module, for example, in collaborations with other modules in the surgical data system 45002, may perform one or more of dynamic form creation, monitoring and reporting, protocol design, and patient recruitment.

The surgical data system 45002 may include a data removal module 45022. Privacy data may go through selective or controlled redaction while the privacy data is used for other control processes. Videos, data streams, and annotations may go through selective data redaction. Selectivity may be based on differing portions of the collection, compilation, and recording steps of the system. Utilization of the data for annotation, metadata tagging of other data points, or verification of data quality may be followed by redaction of the data itself for privacy. Selectivity may be based on detected predefined events. Automatic data redaction during data monitoring and collection may be performed. In an example, face identification may be used to blur the face or block the entire video until the identified face is no longer displayed. Recognizable characters or symbols may be identified. The symbols for predefined acceptable symbols (e.g., bar codes, product labels, etc) may be compared with unexpected symbols which may be redacted or blurred in the recordings. Redaction of data for privacy and data control may be predefined and constant. Data may be redacted as the surgical data system compiles and assembles the data for inputting into databases for storage. Examples that are suitable for use with the present disclosure are described in in U.S. Patent Application Publication No. US 2019-0205566 A1 (U.S. patent application Ser. No. 15/940,632), titled DATA STRIPPING METHOD TO INTERROGATE PATIENT RECORDS AND CREATE ANONYMIZED RECORD, filed Mar. 29, 2018, the disclosure of which is herein incorporated by reference in its entirety. In one or more those examples, data stripping may extract the relevant portions to configure and operate a surgical hub.

Data deletion control and documentation may be enabled. A data erasure process may be implemented, for example, to ensure complete removal of the data and the notation of the removal authorization. Annotation of when and who authorized the deletion of archived data may be removed. Erasure where the removed data is over-written may be secure, for example, to ensure non-recoverability of the removed data.

The data that is selected to be erased and all linked data or metadata coupled to the selected data may be erased.

The surgical data system 45002 may include a big data storage and management module. The big data storage and management module may include one or more of containers, generation algorithms, operational parameters, analytics (e.g., algorithms, automation and real time), usage, security, privacy, compliance, data visualization, copy of raw data (e.g., cloud access to raw data and low storage costs), graphical representation of larger data sets looking for outliers, or algorithms for implementing and monitoring data flows. The generation algorithms may specify data type (e.g., structured; unstructured), data class (e.g., human; machine), and data speed (e.g., batch processing; streaming). The operational parameters may include data management and storage (e.g., store; secure; access; network), engines (e.g., visualization; cloud integration), and how to prepare data for analytics. Algorithms for implementing and monitoring data flows may include one or more of monitor version, parsing un-necessary data, quality checks or processing code.

As described herein, a device (e.g., a surgical hub) may perform one or more of a classification of a data stream (e.g., a surgical data stream), processing the data stream using at least another data stream (e.g., another surgical data stream), or generating a transformed data stream according to a rule set.

The device may determine a classification parameter for the data stream. The device may adjust the classification parameter for the data stream. The device may determine the classification parameter for the data stream based on a classification parameter for a first data stream, a classification parameter for a second data stream, and a mode of interaction between the first data stream and the second data stream, for example, if the data stream is generated using the first data stream and the second data stream. The device may select a data handling scheme for the data stream based on the determined classification parameter for the data stream.

FIG. 16 shows a data classification example 45330. In FIG. 16, a first surgical data stream may be received via a first surgical data interface at 45332. The first surgical data interface may be configured to receive the first surgical data stream from a first surgical instrument. A second surgical data stream may be received via a second surgical data interface at 45334. The second surgical data interface may be configured to receive the second surgical data stream from a second surgical instrument. A first classification parameter associated with the first surgical data stream may be determined at 45336. The first surgical data interface may be identified, and the device may determine the first classification parameter based on the identified first surgical data interface. In an example, the first surgical data interface may be designated to communicate with a first type of surgical instrument. A second classification parameter associated with the second surgical data stream may be determined at 45338. The second surgical data interface may be identified. The device may determine the second classification parameter based on the identified second surgical data interface. In an example, the second surgical data interface may be designated to communicate with a second type of surgical instrument.

The device may determine the first classification parameter based on decoding the first classification parameter in the first surgical data stream. In some examples, the device may determine the first classification parameter by decoding the first surgical data stream and inferring the first classification parameter based on the decoded first surgical data stream, for example, if the first surgical data stream does not include an indication of the first classification parameter. The device may determine the second classification parameter based on decoding the second classification parameter in the second surgical data stream. In some examples, the device may determine the second classification parameter by decoding the second surgical data stream and inferring the second classification parameter based on the decoded second surgical data stream, for example, if the second surgical data stream does not include an indication of the second classification parameter.

A surgical event associated with at least one of the first surgical data stream or the second surgical data stream may be identified at 45340. At 45342, a mode of interaction between the first surgical data stream and the second surgical data stream may be determined based on the identified surgical event. At 45344, a third surgical data stream may be generated based on the mode of interaction between the first surgical data stream and the second surgical data stream. The mode of interaction may include one or more of an enrichment of the first surgical data stream using the second surgical data stream, an aggregation of the first surgical data stream and the second surgical data stream, or a synthesis of the first surgical data stream and the second surgical data stream. In an example, situational data of the identified surgical event may be generated based on the mode of interaction.

At 45346, a third classification parameter for the third surgical data stream may be determined based on the first classification parameter associated with the first surgical data stream, the second classification parameter associated with the second surgical data stream, and the mode of interaction between the first surgical data stream and the second surgical data stream. A value of the third classification parameter may indicate one or more of privacy of the third surgical data stream, a priority of the third surgical data stream, a content type of the third surgical data stream, a context of the third surgical data stream, a retention period associated with the third surgical data stream, or a user preference associated with the third surgical data stream. As an example, the graph 44014 that shows the energy activation type and amount used by the bipolar energy device 44002 over time in FIG. 11 may be received with patient tissue thickness data stream. The graph 44014 and the patient tissue thickness data stream may be synthesized to generate a threshold energy level used for a particular patient's tissue. The graph 44014 may be associated with a classification parameter that indicates a low privacy level. The patient tissue thickness data stream may be associated with a classification parameter that indicates a high privacy level. The generated threshold energy level may be associated with a classification parameter that indicates a high privacy level or a classification parameter that indicates a privacy level that is lower than the high privacy level and higher than the low privacy level.

At least one of the first classification parameter, the second classification parameter, or the third classification parameter may be multidimensional. In an example, the third classification parameter for the third surgical data stream may be determined using a surgical data classification engine tailored to solve multidimensional classification parameters.

At 45350, a data handling scheme may be determined for the third surgical data stream based on the third classification parameter. The data handling scheme may be in consistency with the healthcare data policy. At 45352, data handling of the third surgical data stream may be performed according to the data handling scheme. The data handling scheme may include one or more of a type of storage location for the third surgical data stream or a reliability level associated with a communication path used for the third surgical data stream. The data handling scheme may include data retention guide-lines. The data retention guidelines may specify or guarantee the length of time surgical data can be retained in a particular database.

The communication path may indicate how reliable or secure the transmission resources used to communicate the third surgical data stream should be. In an example, the device may determine based on the third classification parameter, that the third surgical data stream has the highest classification level among a plurality of surgical data streams that are to be transmitted. The device may determine a communication path that is associated with the least amount of interruption among transmission resources that are available to be used for the transmission of the plurality of surgical data streams. The device may send the third surgical data stream using the determined communication path. The device may repeat the sending of the third surgical data stream based on the determination that the third surgical data stream has the highest classification level among the plurality of surgical data streams to be transmitted. The device may select a same data handling scheme for the second surgical data stream as the data handling scheme for the third surgical data stream based on the second classifi-cation parameter that is the same as the third classification parameter.

The first classification parameter, the second classification parameter, and the third classification parameter may be determined in consistency with a healthcare data policy (e.g., one or more rules that are consistent with HIIPPA).

The device may generate situational data for the data stream using another data stream. The device may select two or more data streams and use one data stream to enhance or distill another data stream. The device may select the data stream as the primary data stream and select another data stream as the secondary data stream. The device may enhance or distill the primary data stream using the second-ary data stream. FIG. 17 shows a data processing example 45300. For example, the surgical hub 5104 may be config-ured to perform one or more of 45302, 45306, 45308, 45310, 45312, 45314, 45316, or 45318 in FIG. 17. In FIG. 17, a plurality of data streams may be received during a surgical event at 45302. The plurality of data streams may comprise a first data stream and a second data stream. A first surgical data interface via which the first data stream is received may be identified at 45306. The first surgical data interface may be configured to receive the first data stream from a first surgical instrument. For example, the first surgical data interface may be designated to communicate with a first type of surgical instrument. A second surgical data interface via which the second data stream is received may be identified at 45308. The second surgical data interface may be con-figured to receive the second data stream from a second surgical instrument. For example, the second surgical data interface may be designated to communicate with a second type of surgical instrument. The first data stream and the second data stream may be selected from the plurality of data streams at 45310. At 45312, the first data stream may be determined as a primary data stream based on the first surgical data interface configured to receive the first data stream from the first surgical instrument. At 45314, the second data stream may be determined as a secondary data stream based on the second surgical data interface config-ured to receive the second data stream from the second surgical instrument. The secondary data stream may include a first portion and a second portion. The device may store the first portion of the secondary data stream and not the second portion of the secondary data stream.

Situational data associated with the primary data stream may be generated based on the secondary data stream at 45316. The situational data may indicate a medical decision-making factor of the surgical event. At 45318, the primary data stream with the situational data associated with the primary data stream may be sent during the surgical event. The situational data may be sent using at least one of an annotation for the primary data stream, a context associated with the primary data stream, or meta data that indicates the context associated with the primary data stream. For example, the graph 44014 that shows the energy activation type and amount used by the bipolar energy device 44002 over time in FIG. 11 may be used to generate situational data about the activation and energy amount used by the smoke evacuator for the bipolar energy device 44002, shown by the dotted energy graph 44052. The situational data about the activation and energy amount used by the smoke evacuator for the bipolar energy device 44002 may include one or more of the activation timing, initiation points, deactivation points, and levels.

In an example, the primary data stream may be sent via data packets. At least one of the data packets may include a field indicative of the situational data.

The device may generate a risk indicator based on the primary data stream and the situational data associated with the primary data stream and send the risk indicator. The risk indicator may indicate a probability of an outcome (e.g., an outcome that has a negative impact on the surgical event) associated with the primary data stream. The risk indicator may indicate at least one of an action trigger, a notification, or a threshold. The device may generate control instructions based on the primary data stream and the situational data associated with the primary data stream and send the control instructions to a surgical instrument n communication with the device to change an operation of the surgical instrument.

The first data stream may include a first timing element. The first timing element may indicate a first time when the first data stream is collected during the surgical event. The primary data stream may be sent with the situational data associated with the primary data stream at a second time during the surgical event. A difference between the first time and the second time may be lower than a predetermined value.

The predetermined value may be associated with real-time processing. The difference lower than the predeter-mined value may indicate that the collection of the first data stream and the sending of the third data stream occur in real time. The difference between the first time and the second time may be minimized to correspond with surgical prac-tices. For example, the difference between the first time and the second time may be minimized to represent real-time processing (e.g., on-the-fly processing) or near real-time processing to enable information exchange in a timely manner for purposes of being displayed during the surgical event.

The surgical event may be an ongoing surgical event. The plurality of data streams may include a data stream associ-ated with a historical surgical event, and the processor is further configured to determine that the ongoing surgical event and the historical surgical event have a characteristic in common. The device may generate the situational data based on the data stream associated with the historical surgical event. The characteristic in common may include at least one of a same patient, a same type of surgical procedure, a same type of surgical instrument, or a same type of surgical equipment. For example, the ongoing surgical event and the historical surgical event may use surgical equipment that has the same model number.

Temporally different data streams may be used to provide context to intra-op data streams. Aspects of multiple pre-surgery data sources may be combined to provide contextual aspects of surgical biomarkers or procedure plans, which, for example, may reduce pre-operative biomarker data streams. Reduced pre-operative biomarker data streams may be used to annotate or provide contexts to intra-operative events or biomarker stream processing. In an example, if a biomarker monitor within the OR suddenly plummets or rises outside of the normal acceptable level coincidently with another surgical event, but the pre-operative baseline shows similar events, then the correlation between the event and the biomarker may be noted as not causational. If the same event occurs and there was not history of these similar issues, the annotation may indicate a probable causational link between the event and the biomarker.

Pre-processing of data streams may enable a data stream to be combined with another data stream to provide contexts or annotations. Contextual algorithmic transformations of data streams may be used to create actionable data feeds. The transformed data may be displayed, or it may be displayed with respect to another transformed data stream, for example, to enable the surgeon to monitor the critical aspects and variables and make decisions from them. A first data stream may be combined with an understanding of a surgical procedure, imaging data, patient data, or instrument measures, etc., for example, to transform the data stream into a data stream that is more capable of making decisions from. Contextual transformation of data may be used to aggregate displayed feeds. Examples that are suitable for use with the present disclosure are described in in U.S. Patent Application Publication No. US 2019-0200980 A1 (U.S. patent application Ser. No. 16/182,230), titled SURGICAL SYSTEM FOR PRESENTING INFORMATION INTERPRETED FROM EXTERNAL DATA, filed Nov. 6, 2018, the disclosure of which is herein incorporated by reference in its entirety. In one or more those examples, interpreted information may be displayed to the user based on at least one function of a device including at least one data source not originating within the device.

The device may transform the data stream into a standardized data stream. The device may select a data base in a standard format for inputting the transformed data stream. The device may determine a rule set for transforming the data stream. FIG. 18 shows a data standardization example 45400.

In FIG. 18, a surgical data interface associated with a type of surgical instrument may be identified at 45402. The surgical data interface may be configured to receive a data stream from a surgical instrument of the type associated with the surgical data interface. The data stream may include visualization data, biomarker data, surgical instrument data, or surgical equipment data.

A database may be identified for receiving surgical information indicated by the data stream at 45404. The database may be in a standard format. The standard format may indicate at least one of a resolution, a sampling rate, a measurement type, a unit of measurement, or a type of data stream. The type of data stream may include a discrete data stream or a continuous data stream. In an example, the database may be a relational database.

At 45406, a rule set may be selected based on the identified surgical data interface associated with the type of surgical instrument and based on the identified database. The rule set may include one or more of a data cleaning rule, a data verification rule, or a data formatting rule. In an example, the device may determine, for a first data stream, invalid data and invalid associations based on the selected rule set. A first transformed data stream may exclude the invalid data and the invalid associations. For example, the activation control signal 44008 may be used to clean the overshooting and clean the lagging data set in FIG. 11.

The device may generate a second transformed data stream in the standard format based on a second data stream. The second transformed data stream and the first transformed data stream may be associated with a same sampling rate, a same synchronization, and a same surgical event. The second data stream may include a patient data stream, a surgical instrument data stream associated with a surgical operation, or a surgical equipment data stream. The device may generate an annotation for the first data stream based on the second data stream. The first transformed data stream may include the annotation. In an example, the device may receive a plurality of data streams from a plurality of data sources. Each data stream of the plurality of data streams may be received from a respective data source of the plurality of data sources and comprises an annotation. The annotation may indicate that the respective data source is operatively coupled with a primary surgical equipment.

At 45408, a transformed data stream in the standard format may be generated based on the selected rule set and based on the data stream received via the surgical data interface. The transformed data stream may indicate the surgical information. For example, the device may parse the data stream based on the standard format. The device may determine that a sampling rate associated with standard format is greater than a sampling rate associated with the data stream. The device may determine intermediate average data points based on the data stream and based on the sampling rate associated with the standard format. The transformed data stream may include the intermediate average data points. The transformed data stream may be input to the database at 45410.

Using the database, related surgical procedures may be compared. For example, the device may identify a first surgical data interface associated with a first type of surgical instrument. The first surgical data interface may be configured to receive a first data stream from a first surgical instrument of the first type associated with the first surgical data interface. The device may identify a second surgical data interface associated with a second type of surgical instrument. The second surgical data interface may be configured to receive a second data stream from a second surgical instrument of the second type associated with the second surgical data interface. The device may determine that the first data stream is collected from a first surgical procedure, that the second data stream is collected from a second surgical procedure, and that the first surgical procedure and the second surgical procedure are associated with a common medical characteristic (e.g., a same medical characteristic). The device may determine that a format of the first data stream and a format of the second data stream are different. The device may identify a database that is in a standard format. The device may select a first rule set based on the first surgical data interface associated with the first type of surgical instrument and based on the identified database. The device may select a second rule set based on the second surgical data interface associated with the second type of surgical instrument and based on the identified database. The device may generate a first transformed data stream in the standard format based on the first rule set and based on the first data stream received via the first surgical data interface. The device may generate a second transformed data stream in the standard format based on the second rule set and based on the second data stream received via the second surgical data interface. The device may input the first transformed data stream and the second transformed data stream to the database. The device may compare the first surgical procedure and the second surgical procedure using the database.

Challenges of data stream processing may have implications specific to medical applications. Smart patient care and monitoring may be used. Some data architectures may have a high latency. For example, results may be computed after a significant delay. Data may be received as a continuous stream. Challenges of data stream processing may include scalability, consistency and durability, fault tolerance and data guarantees. In stream computing environments, the data processors may include tens of thousands of diverse sets of computing nodes with different capabilities and interconnected with arbitrary network architectures. Failures may occur due to the inherently unreliable nature of the computing nodes and communication links. Different types of failures may be correlated with each other and have adverse effects on applications running in such environments. Algorithms for connected instruments in the OR may compile data regarding surgical instrument operations in acute outcomes and compile data regarding long term outcomes of the patient. Long streams of data may be collected although such data may not have an immediate effect on the treatment or action of a device. These long steams may include an enormous amount of data in an uncomplied state. The collection of the long streams of data may take days. Data storage may not be freed up until days of the long streams of data have been collected and the outcome has been determined and tied to the collected data.

Complied data may use less data storage. For example, an advanced energy device may record the tissue impendence over a weld, the time to accomplish the weld, the power usage, and the tissue type and combine it with advanced imaging of the tissue or an annotation of a good or bad weld based on bleeding or weeping post transection local to the event. This way, the stream of impendence data may be compiled into a series of key data points or events, a couple key parameters such as a power level, and a resulting micro-outcome of the integrity of the weld. This compiled data may be a smaller data stream than the raw data. This compiled data may need less data storage or communication bandwidth than the raw data does.

Micro-outcomes (e.g., outcomes of s single step, single task, single event, or single job) may be used to provide context and results local to a recorded data stream. The overall outcomes regarding a surgery may not be used to provide context and results. Certain surgical instruments may not have enough processing overhead (e.g., the processing overhead required to process the signals of all the inputs). A powered stapler may have a smart device running an ARM processor. The ARM processor may be linked to a communication array and may have limited storage for its own control programs and some recording of its usage profiles. A certain amount of data regarding the motor current (e.g., a proxy for a force in the end-effector), closure load, internal accelerometers, and control parameters may need to be discarded, for example, after an immediate action is taken. The force-to-fire data may be prescient to the performance of the staple line. The powered stapler may not have access of micro-outcomes and may not continually store the force-to-fire data. A compiled data stream may include identified key maximums, identified key minimums and identified key timing, for example, if events that may be identified by micro-outcomes include what portion of the staple line has an issue and what key data point that issue correlates to. This compiled stream may be tagged with metadata around the tissue thickness, tissue type, and access issues from the scope of advanced imaging system, which may then be more easily transformed to identify overarching trends and/or outcomes.

One or more of the examples shown in FIG. 16, FIG. 17, or FIG. 18 may be performed in association with a method, a process, an apparatus (e.g., an apparatus comprising one or more of antenna, a band limiter, or a display, or apparatus comprising an access unit and/or a transmitter), non-transitory computer readable medium, computer readable medium, computer program product, medium storing instructions, medium storing data, or a signal, for example, to compile surgical data and generate micro-outcomes.

The invention claimed is:

1. A device comprising:
a processor configured to:
receive a plurality of data streams during a surgical event, wherein the plurality of data streams comprises a first data stream and a second data stream;
identify a first surgical data interface via which the first data stream is received, wherein the first surgical data interface is configured to receive the first data stream from a first surgical instrument;
identify a second surgical data interface via which the second data stream is received, wherein the second surgical data interface is configured to receive the second data stream from a second surgical instrument;
select the first data stream and the second data stream from the plurality of data streams;
determine the first data stream as a primary data stream based on the first surgical data interface configured to receive the first data stream from the first surgical instrument;
determine the second data stream as a secondary data stream based on the second surgical data interface configured to receive the second data stream from the second surgical instrument;
generate, based on the secondary data stream, situational data associated with the primary data stream, wherein the situational data indicates a medical decision-making factor of the surgical event;
send the primary data stream with the situational data associated with the primary data stream during the surgical event;
generate control instructions based on the primary data stream and the situational data associated with the primary data stream; and
send the control instructions to a third surgical instrument in communication with the device, wherein the generated control instructions change an operation of the third surgical instrument.

2. The device of claim 1, wherein the first data stream comprises a first timing element, the first timing element indicates a first time when the first data stream is collected during the surgical event, the primary data stream is sent with the situational data associated with the primary data stream at a second time during the surgical event, and a difference between the first time and the second time is lower than a predetermined value.

3. The device of claim 2, wherein the predetermined value is associated with real-time processing, and the difference being lower than the predetermined value indicates that the collection of the first data stream and the sending of the primary data stream occur in real time.

4. The device of claim 1, wherein the primary data stream is sent via data packets, and wherein at least one of the data packets comprises a field indicative of the situational data.

5. The device of claim 1, wherein the first surgical data interface is designated to communicate with a first type of surgical instrument, and wherein the second surgical data interface is designated to communicate with a second type of surgical instrument.

6. The device of claim 1, wherein the situational data is sent using at least one of an annotation for the primary data stream, a context associated with the primary data stream, or meta data that indicates the context associated with the primary data stream.

7. The device of claim 1, wherein the processor is further configured to:

generate a risk indicator based on the primary data stream and the situational data associated with the primary data stream; and send the risk indicator.

8. The device of claim 7, wherein the risk indicator comprises at least one of an action trigger, a notification, or a threshold.

9. The device of claim 1, wherein the secondary data stream of the plurality of data streams comprises a first portion and a second portion, and the processor is further configured to store one of the first portion or the second portion of the secondary data stream.

10. The device of claim 1, wherein the surgical event comprises an ongoing surgical event, the plurality of data streams comprises a third data stream associated with a historical surgical event, and the processor is further configured to determine that the ongoing surgical event and the historical surgical event have a characteristic in common, and wherein the situational data is generated further based on the third data stream associated with the historical surgical event.

11. The device of claim 10, wherein the characteristic in common comprises at least one of a same patient, a same type of surgical procedure, a same type of surgical instrument, or a same type of surgical equipment.

12. A method performed by a device with a processor, the method comprising:

receiving, via the processor, a plurality of data streams during a surgical event, wherein the plurality of data streams comprises a first data stream and a second data stream;

identifying, via the processor, a first surgical data interface via which the first data stream is received, wherein the first surgical data interface is configured to receive the first data stream from a first surgical instrument;

identifying, via the processor, a second surgical data interface via which the second data stream is received, wherein the second surgical data interface is configured to receive the second data stream from a second surgical instrument;

selecting, via the processor, the first data stream and the second data stream from the plurality of data streams;

determining, via the processor, the first data stream as a primary data stream based on the first surgical data interface configured to receive the first data stream from the first surgical instrument;

determining, via the processor, the second data stream as a secondary data stream based on the second surgical data interface configured to receive the second data stream from the second surgical instrument;

generating, via the processor, based on the secondary data stream, situational data associated with the primary data stream, wherein the situational data indicates a medical decision-making factor of the surgical event;

sending, via the processor, the primary data stream with the situational data associated with the primary data stream during the surgical event;

generating, via the processor, control instructions based on the primary data stream and the situational data associated with the primary data stream; and sending, via the processor, the control instructions to a third surgical instrument in communication with the device, wherein the generated control instructions change an operation of the third surgical instrument.

13. The method of claim 12, wherein the first data stream comprises a first timing element, the first timing element indicates a first time when the first data stream is collected during the surgical event, the primary data stream is sent with the situational data associated with the primary data stream at a second time during the surgical event, and a difference between the first time and the second time is lower than a predetermined value.

14. The method of claim 13, wherein the predetermined value is associated with real-time processing, and the difference being lower than the predetermined value indicates that the collection of the first data stream and the sending of the primary data stream occur in real time.

15. The method of claim 12, further comprising:

generating a risk indicator based on the primary data stream and the situational data associated with the primary data stream; and sending the risk indicator.

16. The method of claim 12, wherein the secondary data stream of the plurality of data streams comprises a first portion and a second portion, and the method further comprising storing one of the first portion or the second portion of the secondary data stream.

17. The method of claim 12, wherein the surgical event comprises an ongoing surgical event, the plurality of data streams comprises a third data stream associated with a historical surgical event, and the method further comprises determining that the ongoing surgical event and the historical surgical event have a characteristic in common, and wherein the situational data is generated further based on the third data stream associated with the historical surgical event.

18. The method of claim 17, wherein the characteristic in common comprises at least one of a same patient, a same surgical procedure, a same surgical instrument, or a same surgical equipment.

* * * * *